US 8,906,344 B2

(12) United States Patent
Kasina et al.

(10) Patent No.: US 8,906,344 B2
(45) Date of Patent: Dec. 9, 2014

(54) F-18 RADIOLABELED COMPOUNDS FOR DIAGNOSING AND MONITORING KIDNEY FUNCTION

(71) Applicant: Kasina Laila Innova Pharmaceuticals Private Limited, Vijayawada (IN)

(72) Inventors: Sudhakar Kasina, Mercer Island, WA (US); Venkateswarlu Somepalli, Vijayawada (IN); Paul G. Abrams, Seattle, WA (US); Rama Raju Gokaraju, Vijayawada (IN)

(73) Assignee: Kasina Laila Innova Pharmaceuticals Private Limited, Vijayawada (IN)

( * ) Notice: Subject to any disclaimer, the term of this patent is extended or adjusted under 35 U.S.C. 154(b) by 0 days.

(21) Appl. No.: 14/031,973

(22) Filed: Sep. 19, 2013

(65) Prior Publication Data

US 2014/0086837 A1   Mar. 27, 2014

(30) Foreign Application Priority Data

Sep. 21, 2012   (IN) .......................... 3932/CHE/2012

(51) Int. Cl.
*A61K 51/00*   (2006.01)
*A61K 51/04*   (2006.01)
*C07C 237/36*   (2006.01)
*C07B 59/00*   (2006.01)

(52) U.S. Cl.
CPC .......... *A61K 51/0402* (2013.01); *C07C 237/36* (2013.01); *C07B 59/001* (2013.01)
USPC ........................................ 424/1.89; 562/450

(58) Field of Classification Search
CPC . A61K 51/0402; C07C 237/36; C07B 59/001
USPC ...................................................... 424/1.89
See application file for complete search history.

(56) References Cited

U.S. PATENT DOCUMENTS

| 4,980,147 A | 12/1990 | Fritzberg et al. |
| 2004/0259878 A1 | 12/2004 | Koutcher et al. |
| 2010/0015058 A1 | 1/2010 | Li et al. |
| 2010/0056533 A1 | 3/2010 | Ametamey |
| 2011/0178302 A1 | 7/2011 | Satyamurthy et al. |

OTHER PUBLICATIONS

Tse et al. Int. J. Nucl. Med. 1978, 77-82.*
Williams et al. Ann. NY Acad. Sci. 1965, 110-124.*
Smith et al. J. Clinic. Invest. 24 (1945): 388-404.*
Alauddin, , "Positron emission tomography (PET) imaging with 18F-based radio tracers", Am J Nucl Med Mol Imaging 2012; 2(1): 55-76.
Ametarney, et al., "Molecular Imaging with PET", Chem Rev. 2008, 108, 1501-1516.
Awashti, et al., "Carbon-Flourine Bond Formation for the Synthesis of Aryl Flourides", Synthesis 2010, No. 11. pp. 1804-1821.
Blaufox, et al., "Measurement of renal function in the rat with single injection clearances", Am J Physiol, 1967, 629-632.
Cai, et al., "Chemistry with [18F]Flouride Ion", Eur. J. Org Chem. 2008, 2853-2873.
Fritzberg, et al., "Synthesis and Biological Evaluation of Technetium-99m MAG3 as a HIppuran Replacement", J Nucl Med 27:111-116, 1986.
Isidro-Llobet, et al., "Amino Acid-Protecting Groups", Chem Rev. 2009, 109, 2455-2504.
Li, at al., "Radiopharmaceutical Chemistry for positron emission tomography", Advanced Drug Delivery Reviews 62(2010) 1031-1051.
Taylor, et al., "99mTc(CO)3(NTA): A 99mTc Renal Tracer with Pharmacokinetic Properties Comparable to Those of 131I-OIH in Healthy Volunteers", J Nucl Med 2010; 51:391-396.
Valeur, et al., "Amide bond formation: beyond the myth of coupling reagents", Chem. Soc. Rev., 2009, 38, 606-631.
"International Search Report for PCT/IN2013/000567 dated Jun. 13, 2014".
Xu, et al., "18F-labeled Pyrazolo[1,5-a]pyrimidine Derivatives: Synthesis from 2,4-Dinitrobenzamide and Tosylate Precursors and Comparative Biological Evaluation for Tumor Imaging with Positron Emission Tomography.", Molecules 17(4):3774-3793, 2012 [retrieved on Jul. 24, 2014] Retrieved from the internet <http://www.mdpi.com/1420-3049/17/4/3774>.

* cited by examiner

*Primary Examiner* — Michael G Hartley
*Assistant Examiner* — Sean R Donohue
(74) *Attorney, Agent, or Firm* — Kramer Amado, P.C.

(57) ABSTRACT

The invention relates to $^{18}$F-labeled compounds of formula (I), hydrates, isomers, or pharmaceutically acceptable salts thereof, process for their preparation and pharmaceutical compositions. The invention relates to the methods of diagnosing kidney function in humans by PET imaging.

30 Claims, 2 Drawing Sheets

F-18 RADIOLABELED COMPOUNDS FOR DIAGNOSING AND MONITORING KIDNEY FUNCTION

FIELD OF THE INVENTION

The invention relates to $^{18}$F-labeled aminohippurates; processes for their preparation; their pharmaceutical compositions for diagnosing and monitoring kidney function with good resolution, high sensitivity, and accurate quantification.

BACKGROUND OF THE INVENTION

Kidneys are two bean-shaped organs, each about the size of your fists. They are located near the middle of your back, just below the rib cage. Inside each kidney about a million tiny structures called nephrons filter blood. They remove waste products and extra water, which become urine. The kidneys function on body fluid by filtering a substantial volume of blood (about one-fifth of the total cardiac output is pumped directly to the kidneys). This specific volume of blood is known as the "renal fraction". Approximately, 1.2 liters of blood flows through the kidneys in adult males. As the blood passes through the kidneys, the nephrons clear the blood plasma of unwanted substances such as urea, creatinine, uric acid etc. Most kidney diseases attack the nephrons and this damage may lead to inability in the removal of wastes. Thus, a kidney will become damaged and thus diminish or even cease its function of clearing the blood. The prevalence of kidney diseases is increasing dramatically. Various renal function tests have been devised to assist a physician to evaluate the extent and type of kidney damage that has occurred.

Also, these renal function tests are useful in evaluating whether a kidney is operating properly following a kidney transplant operation. Imaging techniques such as magnetic resonance imaging (MRI), X-rays, or ultrasound (US) provide valuable information on anatomy (namely, anatomical structural imaging), but give limited information on metabolic, biochemical or molecular events.

Nuclear medicine products such as diagnostic radiopharmaceuticals have been in use in very small concentrations at a tracer level in which pharmacological effects are ruled out. Nuclear medicine has been used for more than five decades, and there are no unknown long-term adverse effects from such low-dose exposure. One such renal function testing procedure is known as intravenous scintigraphic urography (this procedure is also commonly known as a dynamic renal function imaging study). Historically, I-131-ortho iodohippuran ($^{131}$I-OIH) has been used for more than 45 years in the nuclear medicine for kidney function determination studies as a Renal Tubular Secretion agent. Due to the high energy of 364 KeV photon flux, one would experience a significant scatter of the images makes it un-suitable for proper diagnoses in the diseased state of the organ. In addition, an 8 day half-life of I-131 radioisotope coupled with the high energy makes $^{131}$I-OIH inadequate for kidney function determination for pediatric usage solely due to high radiation dose to the children. Furthermore, I-131 emits beta particle during radioactive decay which can cause damage to surrounding tissue.

There are several Tc-99m labeled organic molecule based radiopharmaceuticals existed in the literature for renal function both as tubular secretion agents and Glomerular Filtration Rate (GFR) marker agents (Fritzberg et al., U.S. Pat. No. 4,980,147; Fritzberg, et al., J. Nucl. Med. 1986, 27, 111-116). These radiopharmaceuticals include, Tc-99m (Diethylene Triamine Penta Acetic acid (Tc-99mDTPA), Tc-99m Di Mercapto Succinic Acid (Tc-99mDMS A), Tc-99m Mercapto AcetylGlycylGlycylGlycine (Technescan MAG$_3$) and Tc-99m-EC (Technetium labeled di-cysteine, Tc-99m-EC). Currently an estimated 70% of all the renal scans in the United States are performed with Tc-99 mMAG$_3$ and $^{131}$I-OIH has been withdrawn from the market even though it had a higher extraction fraction than Tc-99 mMAG$_3$, solely due to high radiation dose and scatter of the images. Nevertheless, despite of improved image quality and diagnostic superiority to Tc-99 mMAG$_3$ still it has limitations. A small percentage of Tc-99 mMAG$_3$ is eliminated via the hepatobiliary pathway, and this percentage increases in patients with impaired renal function; the resulting activity in the gallbladder has been mistaken for activity in the kidney. A larger issue is the fact that the clearance of Tc-99 mMAG$_3$ is suboptimal and is only 50%-60% of the clearance of $^{131}$I-OIH. Another reported problem is the reproducibility of the Tc-99 mMAG$_3$ clearance based on plasma sample measurements (Andrew T. Taylor et al., J. Nucl. Med. 2010, 51, 391-396).

Hence, these radiopharmaceutical agents are suboptimal in determining the kidney function, because of high radiation, low resolution and low sensitivity due to re-absorption and this would in turn lead to false positives and false negatives making it difficult for correct diagnoses. At present there is no ideal agent for diagnosing and monitoring kidney function with quantitative extraction efficiency measuring effective Renal Plasma Flow (eRPF) solely by tubular secretion.

Thus, there is an urgent unmet medical diagnostic need to design and develop new unequivocally MAG-3 replacement agents for kidney function determination solely by renal tubular secretion alone.

The technical problem to be solved according to the present invention may therefore be seen in providing novel $^{18}$F-labeled pharmaceutical compounds for diagnosing and monitoring kidney function accurately.

SUMMARY OF THE INVENTION

The present invention provides $^{18}$F-labeled pharmaceutical compounds represented by chemical formula (I) and pharmaceutically acceptable salts thereof.

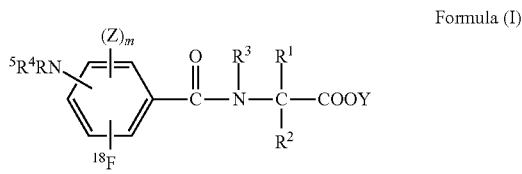

Formula (I)

In another aspect, the invention provides the geometrical isomers/optical isomers/diastereomers, hydrates of the compounds of formula (I).

In another aspect, the invention provides a process for preparing the compounds of formula (I).

In another aspect, the invention provides pharmaceutical compositions comprising at least one $^{18}$F-labeled pharmaceutical compound of formula (I) and derivatives thereof, in combination with at least one pharmaceutically acceptable excipient/carrier/diluents.

Yet another object of the present invention is to provide an imaging agent for diagnosing kidney function using $^{18}$F-compounds represented by chemical formula (I).

In another aspect, the present invention provides a method of diagnosing and monitoring kidney function in a patient in need of such treatment, comprising administering to the patient an effective amount of a compound of formula (I) or their compositions as defined above.

DETAILED DESCRIPTION OF THE INVENTION

Figure 1:
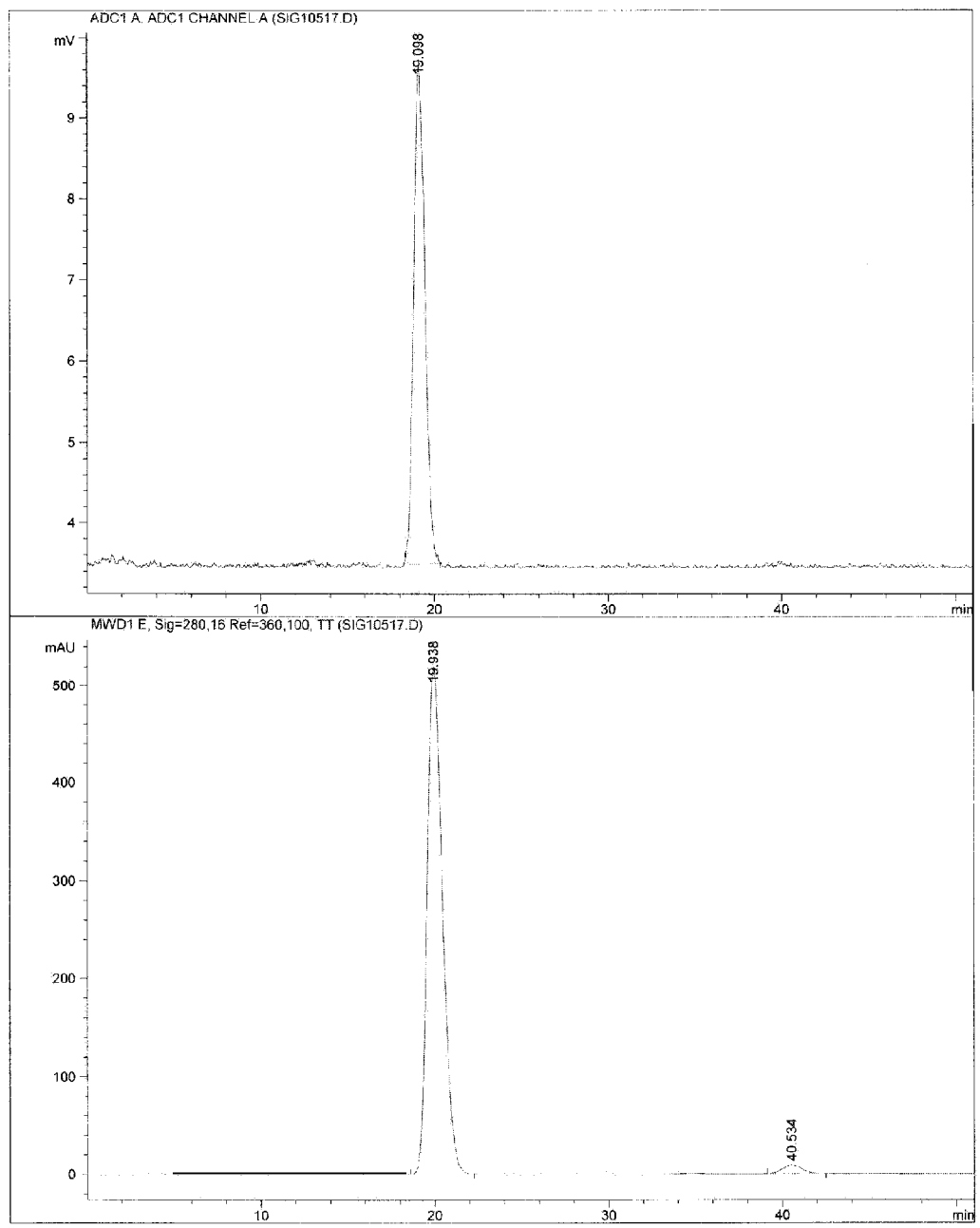
FIG. 1: Analytical HPLC analysis of the isolated compound 6 ($^{18}$F) and compound 6 ($^{19}$F). Upper chromatogram is by Gamma detection and lower chromatogram is by UV detection at 254 nm. Column: C18 semi-preparative or analytical, mobile phase; 5% or 50% CH$_3$CN-15 nM and H$_3$PO$_4$ (pH: 2); Note: Labeled and unlabeled materials co-eluted. The time difference is due to serial gamma and UV detector configuration with UV last, resulting in a short time delay.

The invention will now be described in detail in connection with certain preferred and optional embodiments, so that various aspects thereof may be more fully understood and appreciated.

Positron emission tomography (PET) is a non-invasive functional imaging technique with good resolution, high sensitivity, and accurate quantification. An important advantage of PET is that it provides quantitative information of physiological, biochemical and pharmacological processes in living subjects. Furthermore, as PET tracers are in picomolar concentration, they could measure the biological process without perturbing the biological system. The interest in PET as a clinical and medical research imaging methodology has steadily grown and be widely applied in the field of oncology, cardiology and neurology. Hence usage of PET not only renal function can be assessed but also compartmental assessment within the kidneys can be done with the greater resolution and quantification (Zibo Li et al., Advanced Drug Delivery Reviews, 2010, 62, 1031-1051). Thus, such an agent can provide more diagnostic information than currently used agents such as Single Photon Emission Computerized Tomography (SPECT) with Tc-99m MAG$_3$.

It is reported in the prior art, the use of $^{18}$F-para-fluorohippurate (PFH) for kidney function determination by PET imaging (Awasthi, V., Pathuri, G.; Agashe, H. B., Gali, H. J. Nucl. Med., 2011, 52, 147-153). However, $^{18}$F-labelled aminohippuric acid or their derivatives as truly native gold standards are not known in the literature.

The present invention is based on an organic molecule with a positron emitting radionuclide, $^{18}$F for PET imaging of the kidneys for renal studies. Since positron-emitting radio nuclides of elements such as C, N, O can replace the stable analogs in drugs and bio molecules, it is possible to synthesize PET probes with the same chemical structure as the parent unlabeled molecules without altering their biological activity, however the very short half-lifes of these radio isotopes makes them impractical and unsuitable. It is known that the p-aminohippuric acid is the gold standard tubular secreting agent for kidney function determination. The present inventors expect to have ideally the highest affinity for the receptors in the kidneys by $^{18}$F-p-aminofluorohippurate allowing it to function as a true gold standard renal agent by enhancing high affinity to kidneys as well as faster rate of elimination from the kidneys into the bladder with high efficiency. In addition, both the fluorine and hydrogen atoms attain similar Van-Der-Waal radii in space and hence a mere substitution of fluorine for hydrogen should mimic the $^{18}$F-substituted p-aminohippuric acid for native p-aminohippuric acid as an ideal renal agent through PET studies. The present inventors also expect to have quantitative renal extraction efficiency by the kidney of the $^{18}$F-aminohippurates and with the advantages of PET imaging in camera resolution and hence quantification of radioactivity concentrations within the kidney can be determined at any time point during the dynamic PET imaging.

Figure 2:
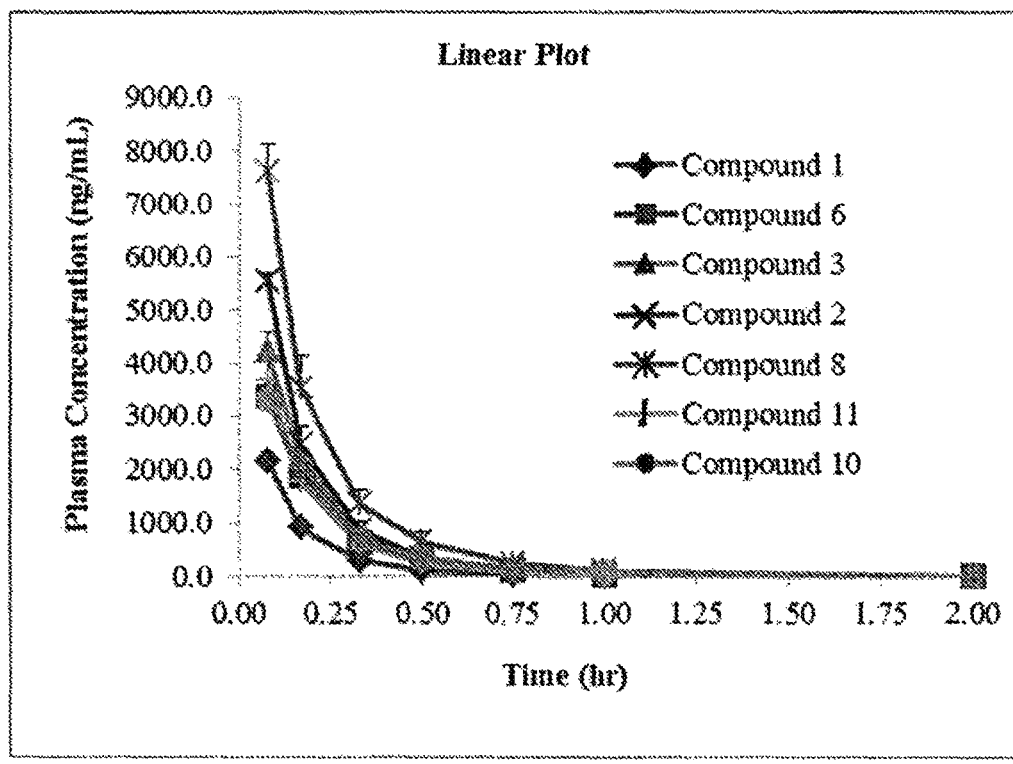
FIG. 2: Plasma clearance of compounds 1, 2, 3, 6, 8, 10 and 11 in rats at a dose of 2 mg/kg through tail vein I.V injection. Blood samples were obtained at 0.0, 0.08, 0.17, 0.25, 0.5, 0.75, 1 and 2 hr. Plasma was isolated and analyzed by LC-MS/MS.

As a part of developing novel kidney function diagnostic agents, an efficient synthetic method was developed for the synthesis of these compounds. Based on this method, thirteen novel $^{18}$F-labelled compounds of formula (I) and their $^{19}$F compounds of formula (Ia) have been prepared. The experiments involving in vitro stability of these compounds have been performed by incubating with freshly collected human plasma at 37° C. The human plasma stability of these compounds was found to be of 100% stability for 1 h as analyzed by LC-MS/MS spectrometry. Some of these compounds were tested for their plasma clearance in rats and the results are shown in FIG. 2 and Table 2. It was found that all these compounds showed excellent plasma clearance. Plasma clearance of compounds 1, 6, 11, 10, 3 and 2 are 5.86±0.50, 3.48±0.63, 3.36±0.41, 3.25±0.13, 2.78±0.19 and 2.23±0.10 (ml/min/100 g) respectively in normal rats. Surprisingly, the plasma clearance of the compounds of formula (I) is much higher than the known renal diagnostic agents, I-131 (plasma clearance is 2.17 ml/min/100 g; Blaufox M D et al., Am. J. Physiol., 1967, 212, 629-632) and Tc-99m MAG-3 (plasma clearance is 2.84 ml/min/100 g; Fritzberg, A R et al., J. Nucl. Med., 1986, 27, 111-116).

Thus, the effective plasma clearance would provide an accurate measurement of kidney function, a gold standard renal agent by definition, must be excreted exclusively via the renal-urinary pathway to be used in humans. The significantly higher plasma clearance of these compounds of formula (I) over I-131 OIH and Tc-99m MAG-3 might be due to devoid of re-absorption from the tubule lumen into plasma. It is known that, Tc-99m MAG-3 results in false positives and false negatives in a clinical setting for inaccurate diagnosis due to re-absorption. On the other hand, with no re-absorption, these new renal agents of formula (I) will not lead to false positives and false negatives resulting with 100% accuracy in clinical diagnosis.

Some of the compounds of formula (I) are screened for their limited organ bio-distribution in Swiss Albino mice and the results were shown in Table 3. Surprisingly, all these compounds showed minimum retention in liver, small intestine and kidney at 15 min after injection. Interestingly, the compounds 1, 2, 3, 6, 8, 10 and 11 showed minimum retention in liver, small intestine and kidney in mice and these results are comparable to the current diagnostic agents such as I-131 and Tc-99m MAG-3. It is also very important for an ideal renal agent not to have any hepatobiliary excretion, in order to eliminate the high background activity especially in patients with impaired renal function. In this context, the total cumulative excretion of these compounds in the intestines and liver was less at 15 min after injection and negligible activities in those organs at 60 min after injection, which is indicative of minimal to negligible clearance by hepatobiliary pathway (Table 4).

Diagnostic advantages of the present novel $^{18}$F compounds of formula (I) using PET imaging over known renal agents:
 a. Higher plasma clearance
 b. No re-absorption from renal lumen into the plasma compartments.

c. No false positives and no false negatives in the clinical diagnosis.
d. Clinical diagnosis with 100% accuracy in normal as well as diseased kidney.
e. Shorter camera usage makes PET imaging cost effective.
f. Due to no re-absorption, effective renal plasma flow (ePRF) can be measured quantitatively without software correction.
g. Absolute clear clarity of scanned images with no scatter.
h. Natural human body constituent with minimal derivatization.
i. High urinary excretion in 15 min shows high extraction efficiency.
j. No clearance by hepatobiliary pathway.
k. No toxicity concern due to native molecule.

Even though selected compounds have been used to demonstrate the present invention, the invention encompasses all compounds of the formula (I) and their derivatives.

Accordingly, the invention provides $^{18}$F-labeled pharmaceutical compounds represented by chemical formula (I);

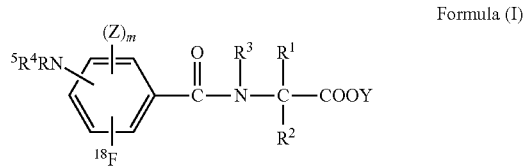

Formula (I)

wherein:

Y is independently selected from hydrogen, $C_{1-6}$alkyl, $C_{1-6}$secondaryalkyl, $C_{1-6}$tertiaryalkyl, $C_{2-6}$alkenyl, $C_{2-6}$alkynyl, haloC$_{1-6}$alkyl, hydroxyC$_{1-6}$alkyl, $C_{3-7}$cycloalkyl, $C_{1-6}$alkylaminoC$_{1-6}$alkyl, di($C_{1-6}$alkyl)aminoC$_{1-6}$ alkyl, $C_{1-6}$alkylaryl, $C_{1-6}$alkylheteroaryl, $C_{1-6}$alkylcarboxylic acid, $C_{1-6}$alkylcarboxamide and a aryl, heteroaryl, $C_{1-6}$alkylaryl, $C_{1-6}$alkylheteroaryl and heterocycloalkyl ring; aryl, heteroaryl and heterocycloalkyl ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, haloC$_{1-6}$alkyl, hydroxyC$_{1-6}$alkyl, $C_{1-6}$alkoxy, haloC$_{1-6}$alkoxy, hydroxyC$_{1-6}$alkoxy, $C_{3-7}$cycloalkyl, $C_{3-7}$cycloalkoxy, $C_{1-6}$alkylamino, di($C_{1-6}$alkyl)amino, aminoC$_{1-6}$alkyl, aminoC$_{1-6}$alkoxy, $C_{1-6}$alkylaminoC$_{1-6}$alkyl, di($C_{1-6}$alkyl)aminoC$_{1-6}$alkyl, $C_{1-6}$alkylsulfinyl, $C_{1-6}$alkylsulfonyl; wherein halogen is selected from all isotopes of F, Cl, Br and I;

Z is independently selected from hydrogen, halogen, astatine (At), hydroxy, formyl, carboxylic acid, amino, nitro, cyano, sulfonic acid, thiole, trihalomethyl, sulfonamide, $C_{1-6}$alkyl, $C_{1-6}$secondaryalkyl, $C_{1-6}$tertiaryalkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, haloC$_{1-6}$alkyl, hydroxyC$_{1-6}$alkyl, $C_{1-6}$alkoxy, haloC$_{1-6}$alkoxy, hydroxyC$_{1-6}$alkoxy, $C_{3-7}$cycloalkyl, $C_{3-7}$cycloalkoxy, $C_{1-6}$alkylamino, di($C_{1-6}$alkyl)amino, aminoC$_{1-6}$alkyl, aminoC$_{1-6}$alkoxy, $C_{1-6}$alkylaminoC$_{1-6}$alkyl, di($C_{1-6}$alkyl)aminoC$_{1-6}$alkyl, $C_{1-6}$alkylsulfinyl, $C_{1-6}$alkylsulfonyl, and a aryl, heteroaryl, $C_{1-6}$alkylaryl, $C_{1-6}$alkylheteroaryl and heterocycloalkyl ring; aryl, heteroaryl and heterocycloalkyl ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, haloC$_{1-6}$alkyl, hydroxyC$_{1-6}$alkyl, $C_{1-6}$alkoxy, haloC$_{1-6}$alkoxy, hydroxyC$_{1-6}$alkoxy, $C_{3-7}$cycloalkyl, hydroxyC$_{1-6}$alkoxy, $C_{3-7}$cycloalkyl, $C_{3-7}$cycloalkoxy, $C_{1-6}$alkylamino, di($C_{1-6}$alkyl)amino, aminoC$_{1-6}$alkyl, aminoC$_{1-6}$alkoxy, $C_{1-6}$alkylaminoC$_{1-6}$alkyl, di($C_{1-6}$alkyl)aminoC$_{1-6}$alkyl, $C_{1-6}$alkylsulfinyl, $C_{1-6}$alkylsulfonyl; wherein halogen is selected from all isotopes of F, Cl, Br and I;

m is 0, 1, 2 or 3

$R^1$ is independently selected from hydrogen, halogen, astatine (At), $C_{1-6}$alkyl, $C_{1-6}$secondaryalkyl, $C_{1-6}$tertiaryalkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$ alkyl)aminocarbonyl, haloC$_{1-6}$alkyl, hydroxyC$_{1-6}$alkyl, $C_{1-6}$alkoxy, haloC$_{1-6}$alkoxy, hydroxyC$_{1-6}$alkoxy, $C_{3-7}$cycloalkyl, $C_{3-7}$cycloalkoxy, $C_{1-6}$alkylamino, di($C_{1-6}$alkyl)amino, aminoC$_{1-6}$alkyl, aminoC$_{1-6}$alkoxy, $C_{1-6}$alkylaminoC$_{1-6}$alkyl, di($C_{1-6}$alkyl)aminoC$_{1-6}$alkyl, $C_{1-6}$alkylsulfinyl, $C_{1-6}$alkylsulfonyl, mercaptoC$_{1-6}$alkyl, $C_{1-6}$alkylmercaptoC$_{1-6}$alkyl, $C_{1-6}$alkylaryl, $C_{1-6}$alkylheteroaryl, $C_{1-6}$alkylcarboxylic acid, $C_{1-6}$alkylcarboxamide, $C_{1-6}$alkylguanidine, $C_{1-6}$alkylselenol and a aryl, heteroaryl, $C_{1-6}$alkylaryl, $C_{1-6}$alkylheteroaryl and heterocycloalkyl ring; aryl, heteroaryl and heterocycloalkyl ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, haloC$_{1-6}$alkyl, hydroxyC$_{1-6}$alkyl, $C_{1-6}$alkoxy, haloC$_{1-6}$alkoxy, hydroxyC$_{1-6}$alkoxy, $C_{3-7}$cycloalkyl, $C_{3-7}$cycloalkoxy, $C_{1-6}$alkylamino, di($C_{1-6}$alkyl)amino, aminoC$_{1-6}$alkyl, aminoC$_{1-6}$alkoxy, $C_{1-6}$alkylaminoC$_{1-6}$alkyl, di($C_{1-6}$alkyl)aminoC$_{1-6}$alkyl, $C_{1-6}$alkylsulfinyl, $C_{1-6}$alkylsulfonyl; wherein halogen is selected from all isotopes of F, Cl, Br and I;

$R^2$ is independently selected from hydrogen, halogen, astatine (At), $C_{1-6}$alkyl, $C_{1-6}$secondaryalkyl, $C_{1-6}$tertiaryalkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$ alkyl)aminocarbonyl, haloC$_{1-6}$alkyl, hydroxyC$_{1-6}$alkyl, $C_{1-6}$alkoxy, haloC$_{1-6}$alkoxy, hydroxyC$_{1-6}$alkoxy, $C_{3-7}$cycloalkyl, $C_{3-7}$cycloalkoxy, $C_{1-6}$alkylamino, di($C_{1-6}$alkyl)amino, aminoC$_{1-6}$alkyl, aminoC$_{1-6}$alkoxy, $C_{1-6}$alkylaminoC$_{1-6}$alkyl, di($C_{1-6}$alkyl)aminoC$_{1-6}$alkyl, $C_{1-6}$alkylsulfinyl, $C_{1-6}$alkylsulfonyl, mercaptoC$_{1-6}$alkyl, $C_{1-6}$alkylmercaptoC$_{1-6}$alkyl, $C_{1-6}$alkylaryl, $C_{1-6}$alkylheteroaryl, $C_{1-6}$alkylcarboxylic acid, $C_{1-6}$alkylcarboxamide, $C_{1-6}$alkylguanidine, $C_{1-6}$alkylselenol and a aryl, heteroaryl, $C_{1-6}$alkylaryl, $C_{1-6}$alkylheteroaryl and heterocycloalkyl ring; aryl, heteroaryl and heterocycloalkyl ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, haloC$_{1-6}$alkyl, hydroxyC$_{1-6}$alkyl, $C_{1-6}$alkoxy, haloC$_{1-6}$alkoxy, hydroxyC$_{1-6}$alkoxy, $C_{3-7}$cycloalkyl, $C_{3-7}$cycloalkoxy, $C_{1-6}$alkylamino, di($C_{1-6}$alkyl)amino, aminoC$_{1-6}$alkyl, aminoC$_{1-6}$alkoxy, $C_{1-6}$alkylaminoC$_{1-6}$alkyl, di($C_{1-6}$alkyl)aminoC$_{1-6}$alkyl, $C_{1-6}$alkylsulfinyl, $C_{1-6}$alkylsulfonyl; wherein halogen is selected from all isotopes of F, Cl, Br and I;

$R^3$ is independently selected from hydrogen, $C_{1-6}$alkyl, haloC$_{1-6}$alkyl, haloC$_{1-6}$alkoxy, $C_{3-7}$cycloalkyl;

R¹ and R³ optionally R¹ and R³ are joined, and taken together with the atoms to which they are attached, form a 5- to 7-membered heterocycloalkyl ring; the heteroatom is N;

R⁴ and R⁵ is independently selected from hydrogen, oxygen, formyl, amino, $C_{1-6}$alkyl, $C_{1-6}$secondaryalkyl, $C_{1-6}$tertiaryalkyl, $C_{2-6}$alkenyl, $C_{2-6}$alkynyl, $C_{1-4}$alkylcarbonyl, aminocarbonyl, $C_{1-6}$ alkylaminocarbonyl, di($C_{1-6}$alkyl)aminocarbonyl, halo$C_{1-6}$alkyl, hydroxy$C_{1-6}$alkyl, $C_{3-7}$cycloalkyl, $C_{1-6}$alkylamino, di($C_{1-6}$alkyl)amino, amino$C_{1-6}$alkyl, $C_{1-6}$alkylamino$C_{1-6}$alkyl, di($C_{1-6}$alkyl) amino$C_{1-6}$alkyl, and a aryl, heteroaryl and heterocycloalkyl ring; aryl, heteroaryl, $C_{1-6}$alkylaryl, $C_{1-6}$alkyl-heteroaryl and heterocycloalkyl ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{-1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl; wherein halogen is selected from all isotopes of F, Cl, Br and I;

In a preferred embodiment, the invention provides $^{18}$F-labeled compounds represented by the following formula (I),

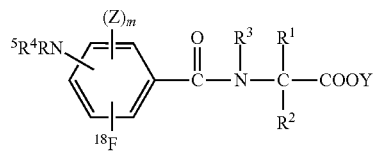

Formula (I)

wherein the Y, Z, R¹, R², R³, R⁴ and R⁵ is H; $^{18}$F is at $2^{nd}$ position of the benzene ring and is selected from the following;

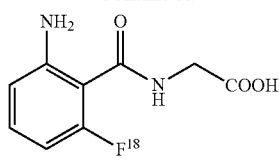

or

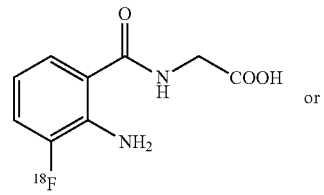

or

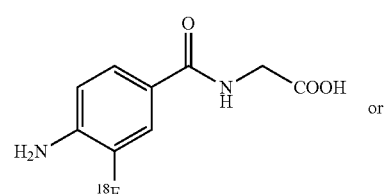

or

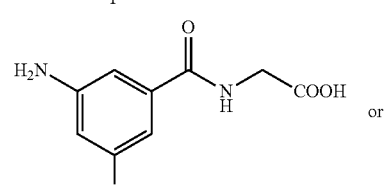

In another embodiment, the invention provides $^{18}$F-labeled compounds represented by the formula (I); wherein the Y, Z, R¹, R², R³, R⁴ and R⁵ is H; $^{18}$F is at $3^{rd}$ position of the benzene ring and is selected from the following;

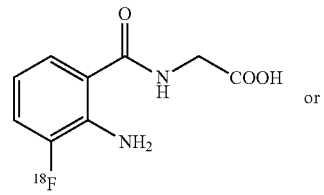

or

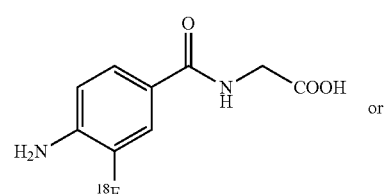

or

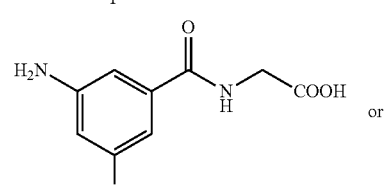

or

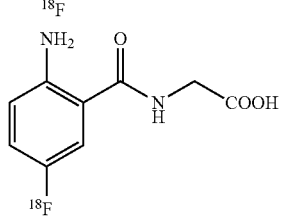

In another embodiment, the invention provides $^{18}$F-labeled compounds represented by the formula (I); wherein the Y, Z, R¹, R², R³, R⁴ and R⁵ is H; $^{18}$F is at $4^{th}$ position of the benzene ring and is selected from the following;

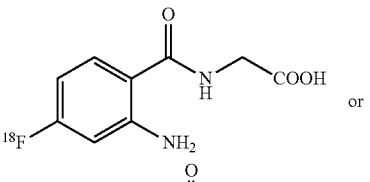

or

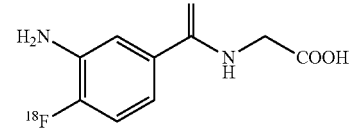

In another embodiment, the invention provides $^{18}$F-labeled compounds represented by the following formula (I),

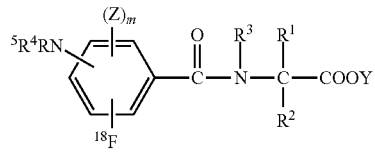

Formula (I)

wherein the Y, Z, $R^1$, $R^2$, $R^3$ is H; one of $R^4$ or $R^5$ is H and the other is $COCH_3$; $^{18}$F is at $2^{nd}$ position of the benzene ring and is selected from the following;

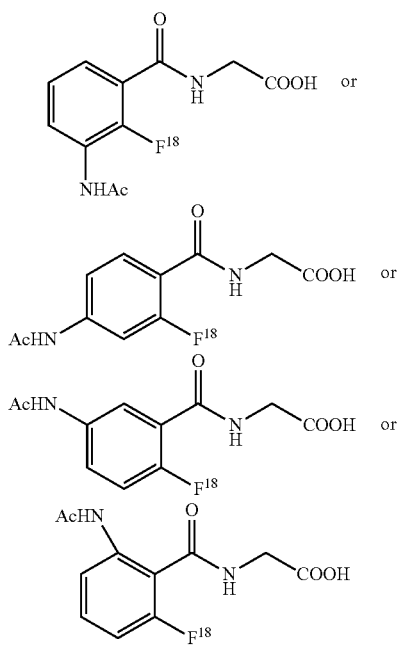

In another embodiment, the invention provides $^{18}$F-labeled compounds represented by the formula (I); wherein the Y, Z, $R^1$, $R^2$, $R^3$ is H; one of $R^4$ or $R^5$ is H and the other is $COCH_3$; $^{18}$F is at $3^{rd}$ position of the benzene ring and is selected from the following;

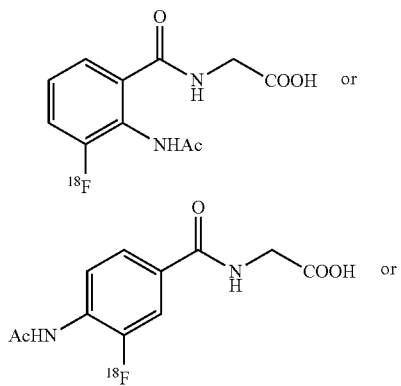

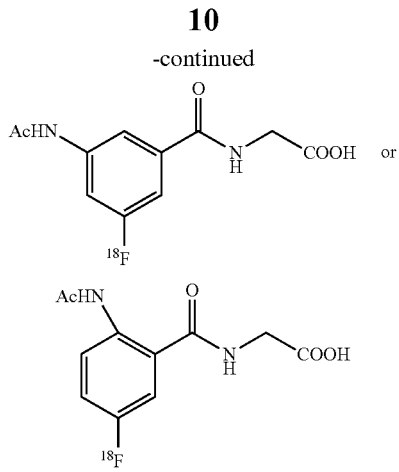

In another embodiment, the invention provides $^{18}$F-labeled compounds represented by the formula (I); wherein the Y, Z, $R^1$, $R^2$, $R^3$ is H; one of $R^4$ or $R^5$ is H and the other is $COCH_3$; $^{18}$F is at $4^{th}$ position of the benzene ring and is selected from the following;

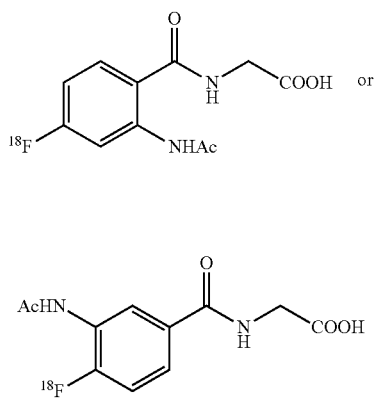

In another embodiment, the invention provides $^{18}$F-labeled compounds represented by the following formula (I),

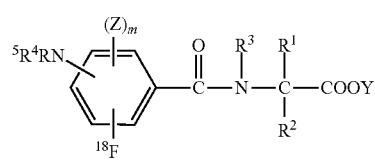

Formula (I)

wherein the Y, Z, $R^3$, $R^4$ and $R^5$ is H; one of $R^1$ and $R^2$ is $CH_3$ and other is H (which is L-alanine or D-alanine) and is selected from the following;

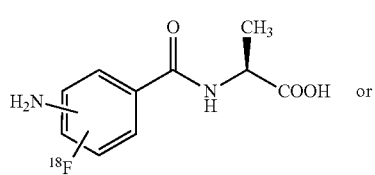

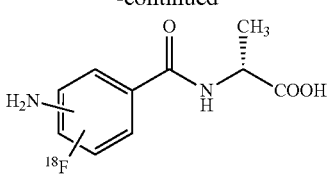

In another embodiment, the invention provides $^{18}$F-labeled compounds represented by the formula (I); wherein the Y, Z, $R^3$ and $R^4$ is H; one of $R^1$ and $R^2$ is $CH_3$ and other is H (which is L-alanine or D-alanine); $R^5$ is $COCH_3$; and is selected from the following;

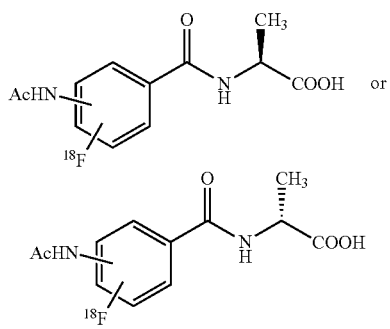

In another embodiment, the invention provides $^{18}$F-labeled compounds represented by the following formula (I),

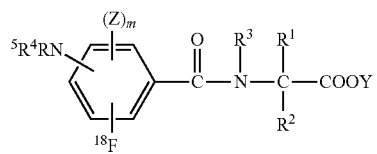

Formula (I)

wherein the Y, Z, $R^1$, $R^2$ and $R^3$ is H; $R^4$ and $R^5$ joined together as $O_2$; $^{18}$F is at $2^{nd}$ position of the benzene ring and is selected from the following;

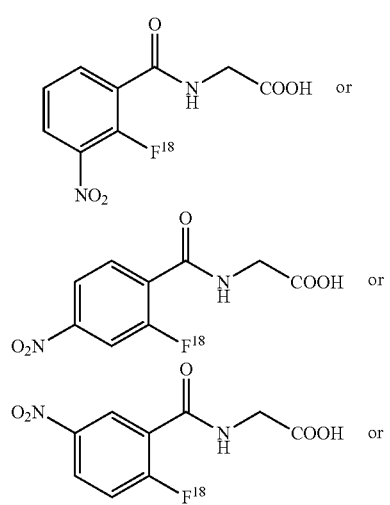

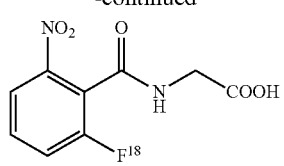

In another embodiment, the invention provides $^{18}$F-labeled compounds represented by the formula (I); wherein the Y, Z, $R^1$, $R^2$ and $R^3$ is H; $R^4$ and $R^5$ joined together as $O_2$; $^{18}$F is at $3^{rd}$ position of the benzene ring and is selected from the following;

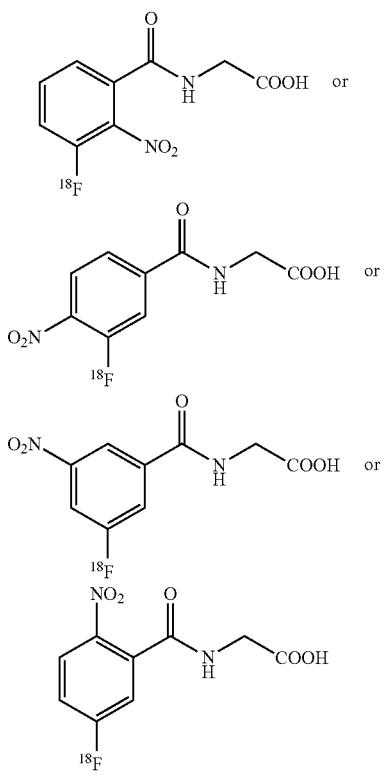

In another embodiment, the invention provides $^{18}$F-labeled compounds represented by the formula (I); wherein the Y, Z, $R^1$, $R^2$ and $R^3$ is H; $R^4$ and $R^5$ joined together as $O_2$; $^{18}$F is at $4^{th}$ position of the benzene ring and is selected from the following;

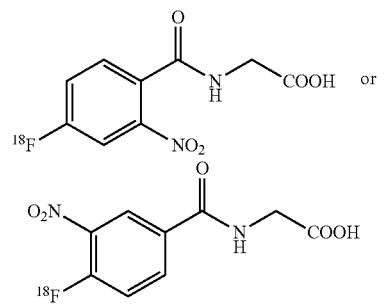

Unless otherwise stated, the following definitions apply for the substituents and residues used throughout this specification and claims:

Alkyl in general represents a normal alkyl, secondary alkyl or tertiary alkyl having 1 to 6 carbon atoms. Non-limiting examples include methyl, ethyl, n-propyl, iso-propyl, n-butyl, isobutyl, sec-butyl, tert-butyl, pentyl, isopentyl, neopentyl, hexyl, isohexyl. The same applies to radicals such as alkylcarbonyl, alkoxy, alkylamino, dialkylamino, alkylsulfonyl, haloakyl and the like.

Alkenyl in general represents a straight-chain or branch unsaturated hydrocarbon radical having 2 to 6 carbon atoms and one carbon-carbon double bond. Non-limiting examples include —CH=CH$_2$, —CH=CHCH$_3$, —C(CH$_3$)=CH$_2$, —CH$_2$CH=CH$_2$, —CH=C(CH$_3$)$_2$, —C(CH$_3$)=CHCH$_3$, —CH$_2$CH=CHCH$_3$, —CH$_2$C(CH$_3$)=CH$_2$, —CH$_2$CH$_2$CH=CH$_2$, —CH$_2$CH=CHCH$_2$CH$_3$, —CH$_2$CH$_2$CH=CHCH$_3$, —CH$_2$CH=C(CH$_3$)$_2$, —CH$_2$CH$_2$C(CH$_3$)=CH$_2$, —CH=CHCH$_2$CH$_2$CH$_3$ etc.

Alkynyl in general represents a straight-chain or branch unsaturated hydrocarbon radical having 2 to 6 carbon atoms and one carbon-carbon triple bond. Non-limiting examples include —C≡CH, —C≡CCH$_3$, —CH$_2$C≡CH, —C≡CCH$_2$CH$_3$, —CH$_2$CH$_2$C≡CH, —CH$_2$C≡CCH$_3$ etc.

Alkoxy illustratively and preferably represents methoxy, ethoxy, n-propoxy, isopropoxy, n-butoxy and tert-butoxy etc.

Alkylcarbonyl in general represents a straight-chain or branched alkyl radical having 1 to 6 carbon atoms which is bonded via a carbonyl group to the rest of the molecule. Non-limiting examples include acetyl, n-propionyl, n-butyryl, isobutyryl, pivaloyl.

Alkoxycarbonyl illustratively and preferably represents methoxycarbonyl, ethoxycarbonyl, n-propoxycarbonyl, isopropoxycarbonyl, n-butoxycarbonyl and tert-butoxycarbonyl etc.

Alkylsulfonyl in general represents a straight-chain or branched alkyl radical having 1 to 6 carbon atoms which is bonded via a sulfonyl (—SO$_2$—) group to the rest of the molecule. Non-limiting examples include methylsulfonyl, ethylsulfonyl, n-propylsulfonyl, isopropylsulfonyl, n-butylsulfonyl, tert-butylsulfonyl etc.

Monoalkylamino in general represents an amino radical having one alkyl residue attached to the nitrogen atom. Non-limiting examples include methylamino, ethylamino, n-propylamino, isopropylamino, n-butylamino, tert-butylamino. The same applies to radicals such as monoalkyl aminocarbonyl etc.

Dialkylamino in general represents an amino radical having two independently selected alkyl residues attached to the nitrogen atom. Non-limiting examples include N,N-dimethylamino, N,N-diethylamino, N,N-diisopropylamino, N-ethyl-N-methylamino, N-methyl-N-n-propylamino, N-iso-propyl-N-n-propylamino, N-tert-butyl-N-methylamino.

Monoalkylaminocarbonyl illustratively and preferably represents methylaminocarbonyl, ethylaminocarbonyl, n-propylaminocarbonyl, isopropylaminocarbonyl, n-butylaminocarbonyl and tert-butylaminocarbonyl etc.

Dialkylaminocarbonyl illustratively and preferably represents N,N-dimethylaminocarbonyl, N,N-diethylaminocarbonyl, N,N-diisopropylaminocarbonyl, N-ethyl-N-methylaminocarbonyl, N-methyl-N-n-propylaminocarbonyl, N-isopropyl-N-n-propylaminocarbonyl and N-tert-butyl-N-methyl-aminocarbonyl etc.

Alkylcarbonylamino in general represents a straight-chain or branched alkyl radical having 1 to 6 carbon atoms which is bonded via a carbonylamino (—CO—NH—) group to the rest of the molecule and which is attached to the carbon atom of that group. Non-limiting examples include acetylamino, n-propionylamino, n-butyrylamino, isobutyrylamino, pivaloylamino etc.

Alkoxycarbonylamino illustratively and preferably represents methoxycarbonylamino, ethoxycarbonylamino, n-propoxycarbonylamino, isopropoxycarbonylamino, n-butoxycarbonylamino and tert.-butoxycarbonylamino etc.

Cycloalkyl in general represents a mono-, bi- or tricyclic saturated hydrocarbon radical having 3 to 7 carbon atoms. Preference is given to monocyclic cycloalkyl radicals having 3 to 7 carbon atoms. Non-limiting examples include cyclopropyl, cyclobutyl, cyclopentyl, cyclohexyl, cycloheptyl, bicyclo[2.2.1]heptyl, adamantly etc.

Heterocycloalkyl in general represents a mono- or bicyclic, saturated heterocyclic radical having a total number of 3 to 10 carbon atoms and up to 2 heteroatoms and/or hetero-groups independently selected from the group consisting of N, O, S, SO and SO$_2$, which ring system can be bonded via a ring carbon atom or, if possible, via a ring nitrogen atom. Non-limiting examples include aziridinyl, azetidinyl, oxetanyl, thietanyl, pyrrolidinyl, pyrazolidinyl, tetrahydrofuranyl, thiolanyl, sulfolanyl, 1,3-dioxolanyl, 1,3-oxazolidinyl, 1,3-thiazolidinyl, piperidinyl, piperazinyl, tetrahydropyranyl, tetrahydrothiopyranyl, 1,3-dioxanyl, 1,4-dioxanyl, morpholinyl, thiomorpholinyl, 1,1-dioxidothiomo[phi]holinyl, perhydroazepinyl, perhydro-1,4-diazepinyl, perhydro-1,4-oxazepinyl, perhydroazocinyl, octahydropyrrolo[3,4-b]pyrrolyl, octahydroisoindolyl, octahydropyrrolo[3,4-b]pyridyl, octahydropyrrolo[1,2-a]pyrazinyl, decahydroisochinolinyl, 7-azabicyclo[2.2.1]heptyl, 3-azabicyclo[3.2.0]heptyl, 7-azabicyclo[4.1.0]heptyl, 2,5-diazabicyclo[2.2.1]heptyl, 2-oxa-5-azabicyclo[2.2.1]heptyl, 2-azabicyclo[2.2.2]octyl, 3-azabicyclo[3.2.1]octyl, 8-azabicyclo[3.2.1]octyl, 8-oxa-3-azabicyclo[3.2.1]octyl, 3-oxa-9-azabicyclo[3.3.1]nonyl.

Particular preference is given to 5- to 7-membered monocyclic heterocycloalkyl radicals having up to 2 heteroatoms selected from the group consisting of N, O and S, such as illustratively and preferably tetrahydrofuranyl, 1,3-dioxolanyl, pyrrolidinyl, tetrahydropyranyl, 1,4-dioxanyl, piperidinyl, piperazinyl, morpholinyl, thiomorpholinyl, perhydroazepinyl, perhydro-1,4-diazepinyl and perhydro-1,4-oxazepinyl.

Heteroaryl in general represents a monocyclic, aromatic heterocyclic radical having 5 or 6 ring atoms, including up to 3 heteroatoms independently selected from the group consisting of N, O, S and Se, which ring system can be bonded via a ring carbon atom or, if possible, via a ring nitrogen atom. Preference is given to 6-membered heteroaryl radicals having up to 2 nitrogen atoms, such as pyridyl, pyrimidyl, pyridazinyl and pyrazinyl, and to 5-membered heteroaryl radicals having up to 3 heteroatoms selected from the group consisting of N, O, S and Se, such as illustratively and preferably thienyl, furyl, pyrrolyl, selenophenyl, thiazolyl, oxazolyl, isothiazolyl, isoxazolyl, pyrazolyl, imidazolyl, oxadiazolyl, thiadiazolyl, triazolyl.

Heteroaryl in general represents a bicyclic, aromatic heterocyclic radical having 9 or 10 ring atoms, including up to 3 heteroatoms independently selected from the group consisting of N, O, S and Se, which ring system can be bonded via a ring carbon atom or, if possible, via a ring nitrogen atom. Non-limiting examples include indole, benzofuran, or benzothiophene.

Halogen represents fluorine, chlorine, bromine and iodine with all possible isotopes.

The compounds according to this invention can also be present in the form of their salts, hydrates and/or solvates.

Salts for the purposes of the present invention are preferably pharmaceutically acceptable salts of the compounds according to the invention.

Pharmaceutically acceptable salts include acid addition salts of mineral acids, carboxylic acids and sulfonic acids, for example salts of hydrochloric acid, hydrobromic acid, nitric acid, sulfuric acid, phosphoric acid, methanesulfonic acid, ethanesulfonic acid, toluenesulfonic acid, benzenesulfonic acid, formamidinesulfonic acid, naphthalenedisulfonic acid, formic acid, acetic acid, propionic acid, lactic acid, tartaric acid, malic acid, citric acid, fumaric acid, maleic acid and benzoic acid.

Pharmaceutically acceptable salts also include salts of customary bases, such as for example and preferably alkali metal salts (for example sodium and potassium salts), alkaline earth metal salts (for example calcium and magnesium salts), and ammonium salts derived from ammonia or organic amines, such as illustratively and preferably ethylamine, diethylamine, triethylamine, ethyldiisopropylamine, monoethanolamine, diethanolamine, triethanolamine, dicyclohexylamine, dimethylaminoethanol, dibenzylamine, N-methylmorpholine, N-methylpiperidine, dihydroabietylamine, arginine, lysine, ethylenediamine and polyamines such as putrescine and cadaverine.

Hydrates of the compounds of the invention or their salts are stoichiometric compositions of the compounds with water, such as, for example, hemi-, mono-, or dihydrates. Solvates of the compounds of the invention or their salts are stoichiometric compositions of the compounds with organic solvents.

The compounds of this invention may, either by nature of asymmetric centers or by restricted rotation, be present in the form of isomers (enantiomers, diastereomers). Any isomer may be present in which the asymmetric center is in the (R)—, (S)—, or (R, S) configuration.

It will also be appreciated that when two or more asymmetric centers are present in the compounds of the invention, several diastereomers and enantiomers of the exemplified structures will often be possible, and that pure diastereomers and pure enantiomers represent preferred embodiments. It is intended that pure stereoisomers, pure diastereomers, pure enantiomers, and mixtures thereof, are within the scope of the invention.

Geometrical isomers by nature of substituents about a double bond or a ring may be present in cis (=Z—) or trans (=E-) form, and both isomeric forms are encompassed within the scope of this invention.

All isomers, whether separated, pure, partially pure, or in racemic mixture, of the compounds of this invention are encompassed within the scope of this invention. The purification of said isomers and the separation of said isomeric mixtures may be accomplished by standard techniques known in the art. For example, diastereomeric mixtures can be separated into the individual isomers by chromatographic processes or crystallization, and racemates can be separated into the respective enantiomers either by chromatographic processes on chiral phases or by optical resolution.

In addition, all possible tautomeric forms of the compounds described above are included according to the present invention.

Some examples of compounds of formula (I) for monitoring kidney function are shown below and their preparation is described in examples 1-13:

2-(4-amino-2-(18)fluorobenzamido)acetic acid;
2-(4-acetamido-2-(18)fluorobenzamido)acetic acid;
2-(3-amino-4-(18)fluorobenzamido)acetic acid;
2-(5-amino-2-chloro-4-(18)fluorobenzamido)acetic acid;
2-(5-amino-2-(18)fluorobenzamido)acetic acid;
2-(4-amino-3-(18)fluorobenzamido)acetic acid;
2-(4-acetamido-3-(18)fluorobenzamido)acetic acid;
2-(2-amino-6-(18)fluorobenzamido)acetic acid;
2-(2-acetamido-6-(18)fluorobenzamido)acetic acid;
(S)-2-(4-amino-2-(18)fluorobenzamido)propanoic acid;
(R)-2-(4-amino-2-(18)fluorobenzamido)propanoic acid;
(S)-2-(2-amino-6-(18)fluorobenzamido)propanoic acid;
(R)-2-(2-amino-6-(18)fluorobenzamido)propanoic acid.

Synthesis of $^{18}$F-Labeled Compounds of Formula (I)

The introduction of fluorine into aromatic system is often carried out in the art using electrophilic fluorine reagents (F$^+$). Examples of such electrophilic reagents include $F_2$, $XeF_2$, AcOF, $CF_3COOF$, Selectfluor™ and N-fluorosulfonamides. Synthesis of these radiolabelled reagents is problematic due to the production of these reagents and these electrophilic fluorination reactions can only provide products with low specific radio activities because of the unavoidable addition of non-radioactive elemental fluorine (often called carrier fluorine). $^{18}$F fluoride [K$^{18}$F] is obtained in much higher amounts and in much higher specific radioactivity and is therefore the preferred reagent for the introduction of fluorine-18 by nucleophilic substitution on aromatic ring.

Several techniques or methods are known in the literature for nucleophilic fluorination onto benzene ring (Ametamey, S. M. et al., Chem. Rev., 2008, 108, 1501-1516; Cai, L. et al., Eur. J. Org. Chem., 2008, 2853-2873; Furuya, T. et al., Synthesis, 2010, 1804-1821; Alauddin, M. M., Am. J. Nucl. Med. Mol. Imaging, 2012, 2, 55-76). For example, Halex (i.e. halogen exchange) fluorination and fluorine exchange with the groups such as nitro, trialkylamine, diazonium, triazine and diaryliodonium.

It is known that the naturally occurring fluorine with the isotopic number 19 ($^{19}$F) in potassium fluoride form (K$^{19}$F) mimics the cyclotron produced radio fluorine isotope with the isotopic number 18 ($^{18}$F) as K$^{18}$F in chemistry reactions as well as their biological behavior. To verify their behavior in vivo, just like potassium fluoride (K$^{19}$F) taken up by the skeletal system indicated by Femur uptake, the potassium fluoride (K$^{18}$F) was also taken up by the skeletal system as determined by Positron Emission Tomography (PET) scan. Hence, it can be assumed with certainty that the compounds of formula (I) with stable isotope $^{19}$F as well as radio isotope $^{18}$F both will have identical pharmacokinetic, pharmaco-dynamic and bio-distribution properties in vivo due to their isotopic similarities.

Given the $^{18}$F half-life (110 min), an efficient synthetic methodology is required. Initially, the inventors have tried nucleophilic substitution by stable $^{19}$F fluorine with KF reagent using known Halex conditions and with other displaceable groups such as nitro, trialkylamine and diazonium salt. However, the reaction failed to give the designed compounds of the invention and is shown below.

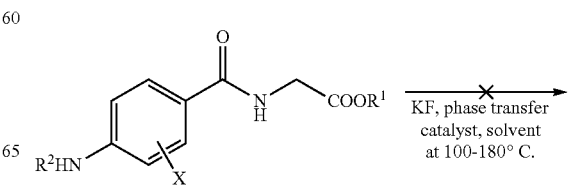

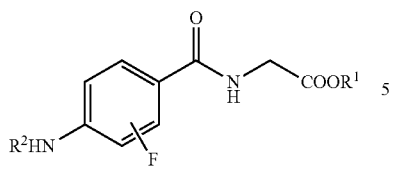

X = Cl or Br or I or NO$_2$ or N$^+$(CH$_3$)$_3$, N$_2$Cl; R$^1$ = H or Bn; R$^2$ = H or COCH$_3$

Recently, nucleophilic fluorination by displacement of iodyl group (IO$_2$) is known in the prior art (Satyamurthy et al., US20110178302). However, our attempts to synthesize the present designed compounds by the prior art knowledge have been failed and is shown below.

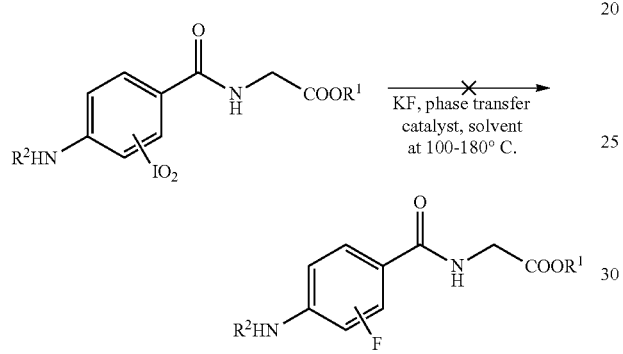

After several attempts, nucleophilic substitution of fluorine by displacing the halogen or nitro group with KF reagent using phase transfer catalyst at ambient temperature with nitro substitution in place of amine or its derivatives on benzene ring has been developed and the nitro group is further reduced to give the present designed compounds and is shown below.

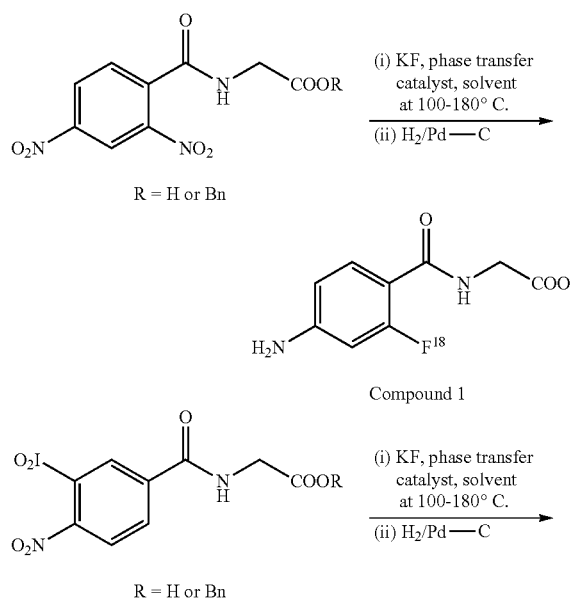

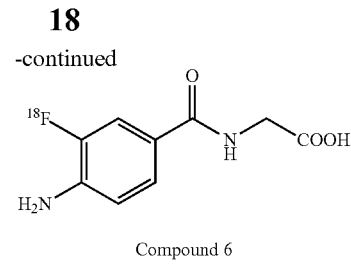

Compound 6

The detailed description of synthesis of all the compounds of formula (I) are described in later part by way of schematic representation (schemes B-I).

Thus, the present invention also relates to a process for preparing the compounds of formula (I), wherein all the groups are as defined earlier.

The compounds of formula (I) may be synthesized as shown in scheme A:

Scheme A

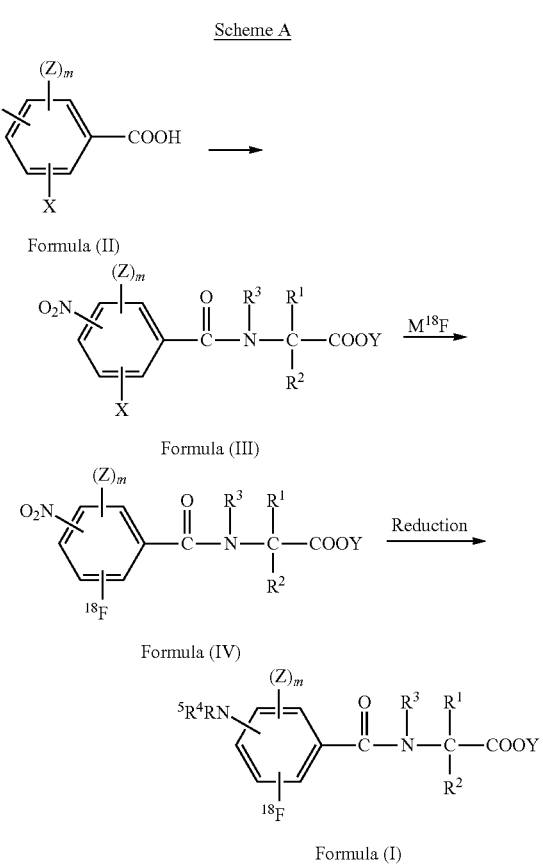

Process A:

Treatment of formula (II), where in X is Cl, Br, I, F, NO$_2$, either with acid protected aminoacid or derivatives thereof using a coupling agent in the presence of a base to give formula (III), where in Y is C$_{1-6}$alkyl, Bn, PMB, t-butyl, CH$_2$CCl$_3$, trimethylsilyl or trityl. Alternatively, formula (II) is treated with chlorinating agent and is further treated either with an aminoacid or acid protected aminoacid or derivatives thereof in the presence of a base to give formula (III), where in Y is H, K, Na, C$_{1-6}$alkyl, Bn, PMB, t-butyl, CH$_2$CCl$_3$, trimethylsilyl or trityl. Reaction of formula (III) with M$^{18}$F, wherein M is an alkali metal, alkaline earth metal, or ammonium compound in the presence of a phase transfer catalyst and a solvent gave formula (IV), which on reduction with a reducing agent and optionally in the presence of acid or organic acid anhydride or mixtures thereof gave formula (I).
Process B:

Treatment of formula (II), where in X is iodine, with acid protected aminoacid or derivatives thereof using coupling agent in the presence of a base and further oxidation with an oxidizing agent gave formula (III), where in X is $IO_2$. Alternatively, formula (II) is treated with chlorinating agent and is further treated with an amino acid or acid protected aminoacid or derivatives thereof in the presence of a base and further oxidation with an oxidizing agent gave formula (III), wherein X is $IO_2$. Reaction of formula (III) with $M^{18}F$, wherein M is an alkali metal, alkaline earth metal, or ammonium compound in the presence of a phase transfer catalyst and a solvent gave formula (IV), which on reduction with a reducing agent and optionally in the presence of acid or organic acid anhydride or mixtures thereof gave formula (I).

In order to make the fluoride ion a reactive nucleophile, several simple but very important manipulations are necessary. Usually $^{18}F^-$ from the target is trapped on an ion exchange column, which is then eluted from the column using potassium carbonate in a water/acetonitrile solution. As the aqueous fluoride is a poor nucleophile because of the solvation, the phase transfer catalyst kryptofix-222 (K222) is added, followed by the removal of water. The potassium cation forms a strong complex with K222 and leaves the fluoride ion exposed and highly nucleophilic in polar non-protic solvent.

A process to make the compounds of formula (I), wherein the chemical reactions may be conducted at ambient temperature under thermal or microwave or ultrasonic conditions.

Aminoacid is selected from the group consisting of glycine, L-alanine, D-alanine, arginine, aspargine, asparitic acid, cysteine, glutamic acid, glutamine, histidine, isoleucine, leucine, lysine, methionine, ornithine, proline, phenylalanine, selenocysteine, serine, tyrosine, threonine, tryptophan, taurine or valine.

Chlorinating reagent is selected from the group consisting of thionyl chloride, phosphorous oxychloride, oxalyl chloride, phosphorous trichloride or phosphorous pentachloride.

Base is inorganic base or organic base; inorganic base is selected from the group consisting of sodium bicarbonate, potassium bicarbonate, sodium carbonate, potassium carbonate, sodium hydroxide or potassium hydroxide; organic base is selected from the group consisting of triethylamine, pyridine or dimethylaminopyridine.

Amide forming coupling agent is selected from all the known reagents in the prior art (Valeur, E. and Bradley, M. Chem. Soc. Rev., 2009, 38, 606-631) such as Dicyclohexylcarbodiimide (DCC), 1-ethyl-3-(3-dimethylaminopropyl) carbodiimide (EDC) and optionally additives such as 1-hydroxy-1H-benzotriazole (HOBt).

Acid protecting aminoacids are prepared by the known methods in the prior art (Albert Isidro-Llobet et al., Chem. Rev, 2009, 109, 2455-2504).

Alkali metal is selected from the group consisting of lithium, sodium, potassium, caesium, rubidium or francium; alkaline earth metal is selected from the group consisting of beryllium, magnesium, calcium, strontium, barium or radium; ammonium compounds are selected from the group consisting of tetramethylammonium, tetraethylammonium or tetrabutylammonium.

Phase transfer catalyst is selected from the group consisting of 18-crown-6, 15-crown-5, kryptofix-222, tetraphenylphosphonium bromide, tetrabutylammonium halides or polyethylene glycol (PEG); preferably kryptofix-222.

Solvent is selected from the group consisting of acetonitrile, dimethylsulfoxide, dimethylformamide, sulfolane, methylsulfone, tetraethyleneglycol dimethylether, tetrahydrofuran, ethylene glycol, hexamethylphosphoramide (HMPA) or N-methyl-2-pyrrolidone (NMP).

Reducing agent is selected from the group consisting of iron, tin, zinc, indium, stannous chloride, nickel chloride, sodium sulfide, sodium dithionite, palladium-carbon in the presence of hydrogen gas or hydrogen source; or Raney-nickel in the presence of hydrogen gas or hydrogen source; hydrogen source is selected from 1,4-cyclohexadiene, cyclohexene, ammonium formate or formic acid.

Acid is selected from the group consisting of hydrochloric acid, nitric acid, sulfuric acid, phosphoric acid, methanesulfonic acid, acetic acid, formic acid or prionic acid; organic acid anhydride is selected from formic anhydride, acetic anhydride, propionic anhydride or mixtures thereof.

Oxidizing agent is selected from the group consisting of hydrogen peroxide-acetic anhydride, sodium hypochlorite, peracetic acid, perbenzoic acid, chromium trioxide, potassium permanganate, dimethyldioxirane, sodium periodate or potassium bromate.

In a preferred embodiment, the invention provides a process for preparing $^{18}F$-labeled compounds represented by the formula (I) and is shown below;

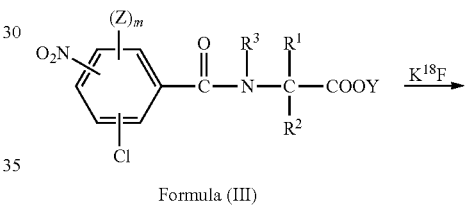

Formula (III)

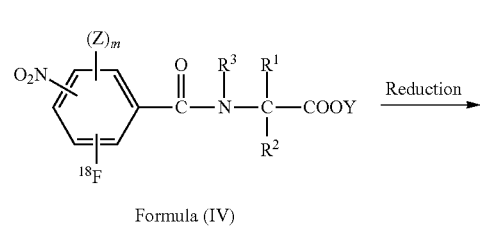

Formula (IV)

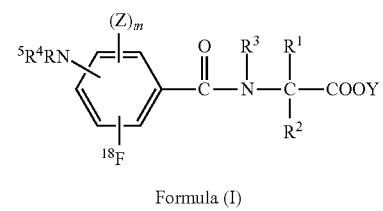

Formula (I)

Treatment of formula (III) with cyclotron generated $K^{18}F$ in the presence of a catalyst gave formula (IV), which on reduction with a reducing agent to give formula (I).

In another embodiment, the invention provides a process for preparing $^{18}F$-labeled compounds represented by the formula (I) and is shown below;

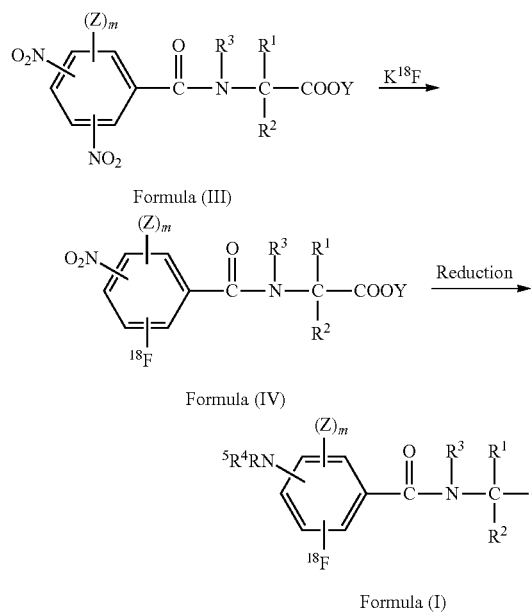

Treatment of formula (III) with cyclotron generated $K^{18}F$ in the presence of a catalyst gave formula (IV), which on reduction with a reducing agent to give formula (I).

In another embodiment, the invention provides a process for preparing $^{18}F$-labeled compounds represented by the formula (I) and is shown below;

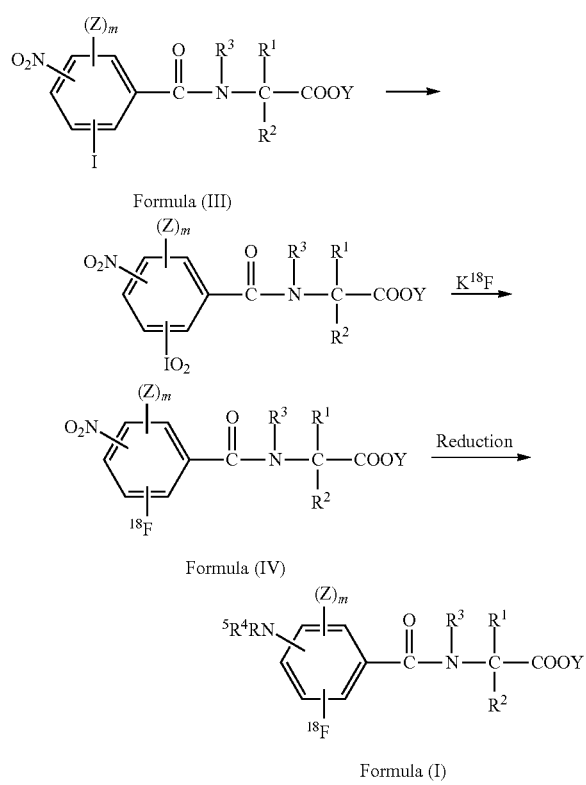

Oxidation of formula (III) with an oxidizing agent gave iodyl ($IO_2$) derivative, which on treatment with cyclotron generated $K^{18}F$ in the presence of a catalyst gave formula (IV); formula (IV) on further reduction with a reducing agent gave formula (I).

Radiochemistry

The synthetic process of some of the compounds of formula (I) is described as shown below.

The radio-labeled compounds of formula (I) are prepared starting with the standard kryptofix-$K_2CO_3$-mediated nucleophilic $^{18}F$ exchange reaction with the precursor compounds represented by chemical formula III (intermediates 1-14). Introduction of the fluorine-18 using a no-carrier-added nucleophilic substitution with $K[^{18}F]FK222$ (K222: Kryptofix [2.2.2]; 4,7,13,16,21,24-hexaoxa-1,10-diazabicyclo[8.8.8]hexacosane) is conducted in dry DMSO at 120-170° C. for 10-30 min. After the fluorination reaction, semi-preparative HPLC purification of the mixture gave $^{18}F$ compound in 44-65±5% (n=2) radiochemical yields based on $[^{18}F]F^-$, corrected for physical decay (Table 1). The identity of $^{18}F$ compounds were confirmed by co-injection with unlabeled compound on analytical HPLC. These compounds are further reduced using reducing agents to obtain range of derivatives of $^{18}F$-labeled compounds of formula (I). The radiochemical purity of the final compounds is more than 95%, as determined by HPLC (FIG. 1).

TABLE 1

Nucleophilic (18)F exchange reactions

| Precursor compound | Radio Chemical Yield (% RCY) | | Further reduction to 18F-compounds of formula (I) |
|---|---|---|---|
| | 120° C. (10 min) | 170° C. (30 min) | |
| Intermediate 2 | 27 | 48 | Compound 1 and 2 |
| Intermediate 3 | 25 | — | Compound 3 |
| Intermediate 5 | 42 | 52 | Compound 3 |
| Intermediate 6 | 45 | 48 | Compound 5 |
| Intermediate 7 | 62 | 65 | Compound 6 |
| Intermediate 8 | 58 | 61 | Compound 6 |
| Intermediate 9 | 46 | 52 | Compound 7 |
| Intermediate 10 | 30 | 47 | Compound 8 and 9 |
| Intermediate 11 | 29 | 48 | Compound 10 |
| Intermediate 12 | 26 | 59 | Compound 11 |
| Intermediate 13 | — | 44 | Compound 12 |
| Intermediate 14 | — | 49 | Compound 13 |

Reaction Conditions
1. Thermal: The introduction of fluorine-18 using a no-carrier-added nucleophilic substitution with $K[^{18}F]$FK222 is conducted in various dry solvents such as DMSO, acetonitrile, DMF etc. at 100-170° C. for 10-30 min.
2. Microwave: The introduction of fluorine-18 using a no-carrier-added nucleophilic substitution with $K[^{18}F]$FK222 is conducted in various dry solvents such as DMSO, acetonitrile, DMF etc. under microwave conditions for 1-5 min.
3. Ultrasonic: The introduction of fluorine-18 using a no-carrier-added nucleophilic substitution with $K[^{18}F]$FK222 is conducted in various dry solvents such as DMSO, acetonitrile, DMF etc. under ultrasonic conditions for 5-10 min.

Half-life of $^{18}F$ radio isotope is only 110 min and the present inventive compounds of formula (I) should be characterized by their $^{19}F$ compounds of formula (Ia). Furthermore, the identity of $^{18}F$ radio-labeled compounds of formula (I) has to be confirmed unequivocally by co-injection with an unlabeled compounds of formula (I) on analytical HPLC column. Thus the compounds of formula (I) are synthesized with $^{18}F$ radio isotope and their $^{19}F$ stable isotope.

The synthetic process of some of the $^{18}F$ compounds of formula (I) and their corresponding $^{19}F$ compounds is illustrated by way of schematic representation and are shown below. Hence, synthesis of compounds of formula (I), more specifically the synthesis of compound 1 and compound 2 is achieved by the steps shown in scheme B.

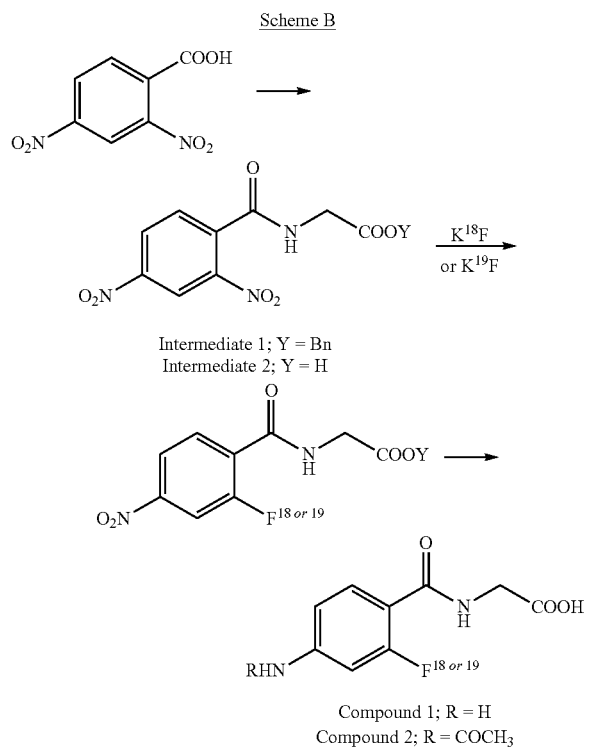

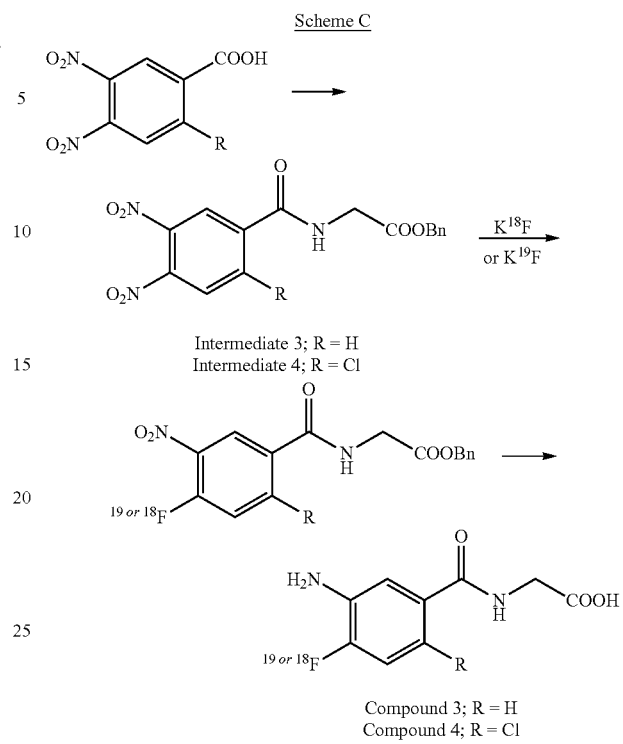

As shown in scheme B, treatment of 2,4-dinitrobenzoic acid with chlorinating agent such as thionyl chloride gave 2,4-dinitrobenzoyl chloride which on further treatment with benzyl glycinate in the presence of triethylamine gave benzyl 2-(2,4-dinitrobenzamido)acetate (intermediate 1). The intermediate 1 is treated either with $K^{18}F$ or $K^{19}F$ in the presence of a catalyst such as kryptofix[2.2.2] or 18-crown-6 to yield benzyl 2-(2-fluoro-4-nitrobenzamido)acetate, which on reduction with hydrogen gas or hydrogen source in the presence of Pd/C gave 2-(4-amino-2-fluorobenzamido)acetic acid (compound 1) in good yield. Alternatively, treatment of 2,4-dinitrobenzoyl chloride with glycine in presence of a mild base such as sodium carbonate gave 2-(2,4-dinitrobenzamido)acetic acid (intermediate 2). Treatment of intermediate 2 either with $K^{18}F$ or $K^{19}F$ gave 2-(2-fluoro-4-nitrobenzamido)acetic acid, which on reduction with zinc dust and ammonium formate or hydrogen gas/hydrogen source in the presence of Pd/C gave compound 1. Treatment of intermediate 2 either with $K^{18}F$ or $K^{19}F$ and further reduction with iron powder in the presence of acetic anhydride-acetic acid gave 2-(4-acetamido-2-fluorobenzamido)acetic acid (compound 2).

Synthesis of compounds of formula (I), more specifically the synthesis of compound 3 and compound 4 is achieved by the steps shown in scheme C.

As shown in scheme C, reaction of 3,4-dinitrobenzoic acid with thionyl chloride gave 3,4-dinitrobenzoyl chloride, which on further treatment with benzyl glycinate in the presence of triethylamine gave benzyl 2-(3,4-dinitrobenzamido)acetate (intermediate 3). The intermediate 3 is treated either with $K^{18}F$ or $K^{19}F$ in the presence of a catalyst such as kryptofix [2.2.2] or 18-crown-6 to yield benzyl 2-(4-fluoro-3-nitrobenzamido)acetate, which on reduction with hydrogen gas or hydrogen source in the presence of Pd/C gave 2-(3-amino-4-fluorobenzamido)acetic acid (compound 3). In an analogous manner, 2-(5-amino-2-chloro-4-fluorobenzamido)acetic acid (compound 4) is synthesized starting from 2-chloro-4,5-dinitrobenzoic acid.

Alternatively, synthesis of compound 3 is achieved by the steps shown in scheme D.

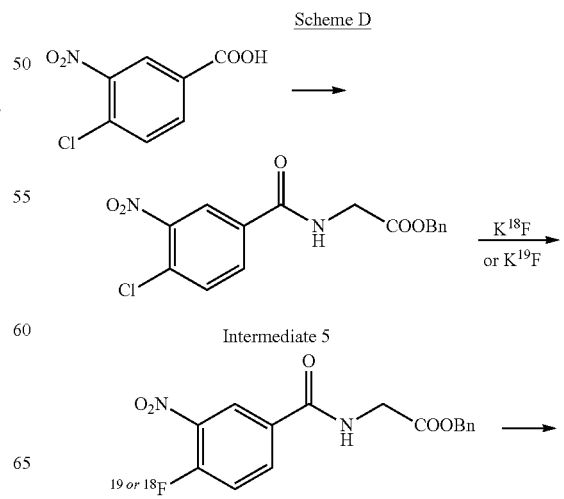

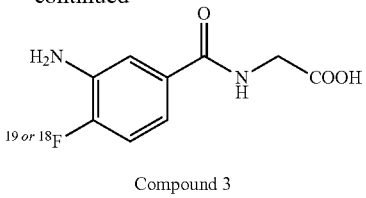

Compound 3

As shown in scheme D, reaction of 4-chloro-3-nitrobenzoic acid with thionyl chloride gave 4-chloro-3-nitrobenzoyl chloride, which on further treatment with benzyl glycinate in presence of triethylamine gave benzyl 2-(4-chloro-3-nitrobenzamido)acetate (intermediate 5). The intermediate 5 is treated either with $K^{18}F$ or $K^{19}F$ in the presence of kryptofix [2.2.2] or 18-crown-6 to yield benzyl 2-(4-fluoro-3-nitrobenzamido)acetate, which on further reduction with hydrogen gas or hydrogen source in the presence of Pd/C gave compound 3.

Synthesis of compounds of formula (I), more specifically the synthesis of compound 5 is achieved by the steps shown in scheme E.

Scheme E

Intermediate 6

Compound 5

As shown in scheme E, reaction of 2-chloro-5-nitrobenzoic acid with thionyl chloride gave 2-chloro-5-nitrobenzoyl chloride, which on further treatment with benzyl glycinate in the presence of triethylamine gave benzyl 2-(2-chloro-5-nitrobenzamido)acetate (intermediate 6). Treatment of intermediate 6 either with $K^{18}F$ or $K^{19}F$ in the presence of kryptofix [2.2.2] or 18-crown-6 to yield benzyl 2-(2-fluoro-5-nitrobenzamido)acetate, which on further reduction with hydrogen gas or hydrogen source in the presence of Pd/C gave 2-(5-amino-2-fluorobenzamido)acetic acid (compound 5).

Synthesis of compounds of formula (I), more specifically the synthesis of compound 6 and compound 7 is achieved by the steps shown in scheme F.

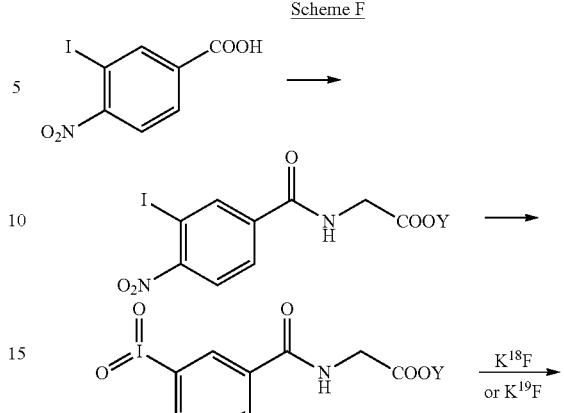

Scheme F

Intermediate 7; Y = Bn
Intermediate 8; Y = $CH_2CCl_3$
Intermediate 9; Y = K

Compound 6; R = H
Compound 7; R = $COCH_3$

As shown in scheme F, condensation of 3-iodo-4-nitrobenzoic acid with benzyl glycinate in presence of DCC and catalytic amount of DMAP gave benzyl 2-(3-iodo-4-nitrobenzamido)acetate, which on oxidation using oxidizing agents such as acetic anhydride-hydrogen peroxide gave benzyl 2-(3-iodyl-4-nitrobenzamido)acetate (intermediate 7). The intermediate 7 is treated either with $K^{18}F$ or $K^{19}F$ in the presence of kryptofix[2.2.2] or 18-crown-6 to yield benzyl 2-(3-fluoro-4-nitrobenzamido)acetate, which on reduction with hydrogen gas or hydrogen source in the presence of Pd/C gave 2-(4-amino-3-fluorobenzamido)acetic acid (compound 6). Reaction of 3-iodo-4-nitrobenzoic acid with thionyl chloride gave 3-iodo-4-nitrobenzoyl chloride, which on further treatment with 2,2,2-trichloroethyl glycinate in the presence of triethylamine gave 2,2,2-trichloroethyl 2-(3-iodo-4-nitrobenzamido)acetate. Oxidation of 2,2,2-trichloroethyl 2-(3-iodo-4-nitrobenzamido)acetate with acetic anhydride-hydrogen peroxide gave 2,2,2-trichloroethyl 2-(3-iodyl-4-nitrobenzamido)acetate (intermediate 8). Reaction of intermediate 8 either with $K^{18}F$ or $K^{19}F$ gave 2,2,2-trichloroethyl 2-(3-fluoro-4-nitrobenzamido)acetate, which on reduction with zinc dust gave compound 6. In an analogous manner, treatment of 3-iodo-4-nitrobenzoyl chloride with glycine in presence of sodium carbonate gave 2-(3-iodo-4-nitrobenzamido)acetic acid, which on oxidation with acetic anhydride-hydrogen peroxide and followed by treatment with KOH gave potassium 2-(3-iodyl-4-nitrobenzamido)acetate (intermediate 9). The intermediate 9 is treated either with $K^{18}F$ or $K^{19}F$ to yield 2-(3-fluoro-4-nitrobenzamido)acetic acid, which on reduction with iron powder in presence of acetic acid gave compound 6. Reduction of 2-(3-fluoro-4-nitrobenzamido) acetic acid with iron powder in the presence of acetic anhydride-acetic acid gave 2-(4-acetamido-3-fluorobenzamido) acetic acid (compound 7).

Synthesis of compounds of formula (I), more specifically the synthesis of compound 8 and compound 9 is achieved by the steps shown in scheme G.

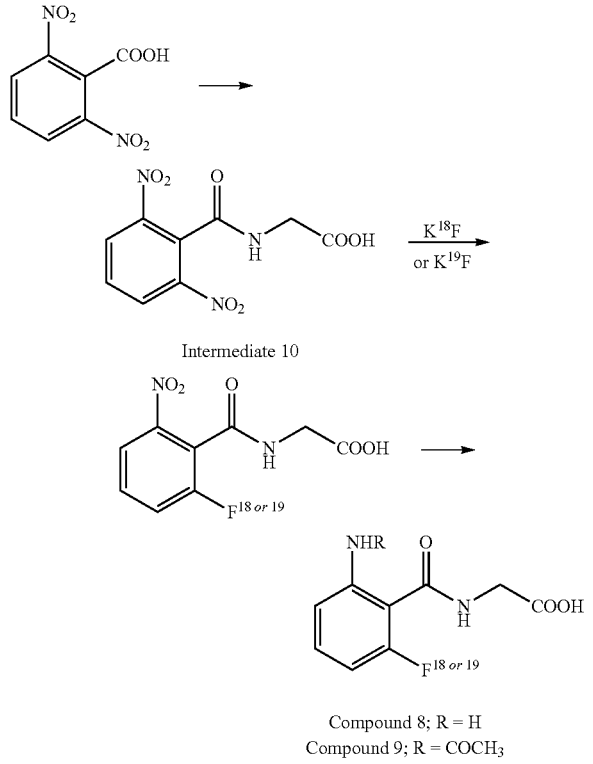

Intermediate 10

Compound 8; R = H
Compound 9; R = COCH₃

As shown in scheme G, 2,6-dinitrobenzoyl chloride prepared from 2,6-dinitrobenzoic acid is treated with glycine in the presence of sodium carbonate to yield 2-(2,6-dinitrobenzamido)acetic acid (intermediate 10). Treatment of intermediate 10 either with K$^{18}$F or K$^{19}$F gave 2-(2-fluoro-6-nitrobenzamido)acetic acid, which on reduction with indium powder in the presence of either acetic acid or acetic anhydride-acetic acid gave the corresponding 2-(2-amino-6-fluorobenzamido)acetic acid (compound 8) or 2-(2-acetamido-6-fluorobenzamido)acetic acid (compound 9) respectively.

Synthesis of compounds of formula (I), more specifically the synthesis of compound 10 and compound 11 is achieved by the steps shown in scheme H.

Scheme H

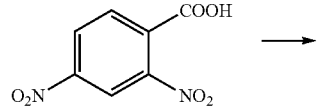

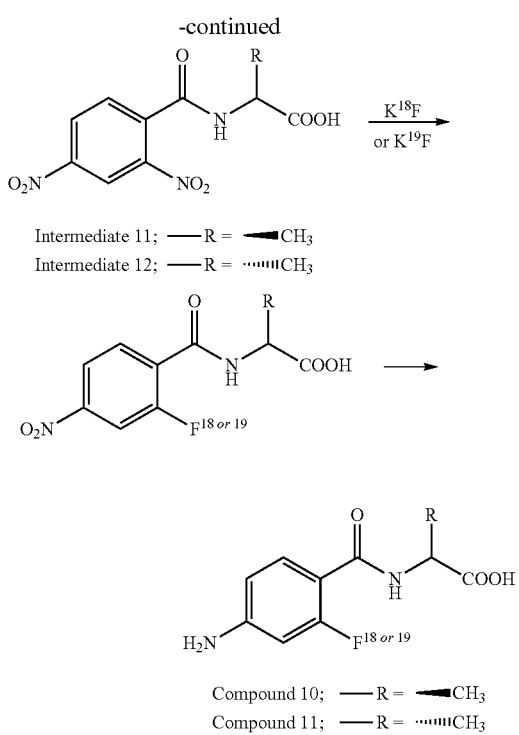

Intermediate 11; ——R = ◢CH₃
Intermediate 12; ——R = ⋯⋯CH₃

Compound 10; ——R = ◢CH₃
Compound 11; ——R = ⋯⋯CH₃

As shown in scheme H, 2,4-dinitrobenzoyl chloride prepared from 2,4-dinitrobenzoic acid is treated with L-alanine in presence of sodium carbonate to yield (S)-2-(2,4-dinitrobenzamido)propanoic acid (intermediate 11). Treatment of intermediate 11 either with K$^{18}$F or K$^{19}$F gave (S)-2-(2-fluoro-4-nitrobenzamido)propanoic acid, which on reduction with iron powder in presence of acetic acid gave (S)-2-(4-amino-2-fluorobenzamido)propanoic acid (compound 10). In an analogous manner, treatment of 2,4-dinitrobenzoyl chloride with D-alanine gave (R)-2-(2,4-dinitrobenzamido) propanoic acid (intermediate 12), which on treatment either with K$^{18}$F or K$^{19}$F and further reduction with iron powder gave (R)-2-(4-amino-2-fluorobenzamido)propanoic acid (compound 11).

Synthesis of compounds of formula (I), more specifically the synthesis of compound 12 and compound 13 is achieved by the steps shown in scheme I.

Scheme I

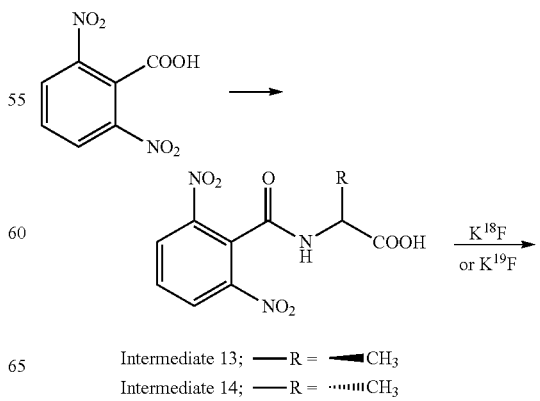

Intermediate 13; ——R = ◢CH₃
Intermediate 14; ——R = ⋯⋯CH₃

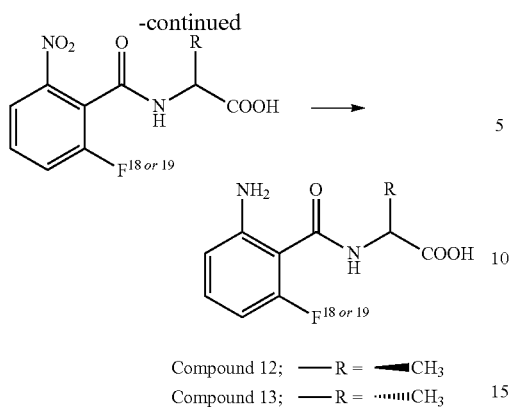

Compound 12; —R = —◀CH₃
Compound 13; —R = ·······‖CH₃

As shown in scheme 1,2,6-dinitrobenzoyl chloride prepared from 2,6-dinitrobenzoic acid is treated with L-alanine in the presence of sodium carbonate to yield (S)-2-(2,6-dinitrobenzamido)propanoic acid (intermediate 13). Treatment of intermediate 13 either with $K^{18}F$ or $K^{19}F$ gave (S)-2-(2-fluoro-6-nitrobenzamido)propanoic acid, which on reduction with iron powder in the presence of acetic acid gave (S)-2-(2-amino-6-fluorobenzamido)propanoic acid (compound 12). In an analogous manner, treatment of 2,6-dinitrobenzoyl chloride with D-alanine gave (R)-2-(2,6-dinitrobenzamido) propanoic acid (intermediate 14), which on treatment either with $K^{18}F$ or $K^{19}F$ and further reduction with iron powder gave (R)-2-(2-amino-6-fluorobenzamido)propanoic acid (compound 13).

Compositions

In another aspect, the invention provides pharmaceutical compositions comprising a compound of formula (I) or a pharmaceutically acceptable salt or solvates or hydrates or stereoisomers thereof in combination with a pharmaceutically acceptable excipient(s) or carrier(s) or diluent(s);

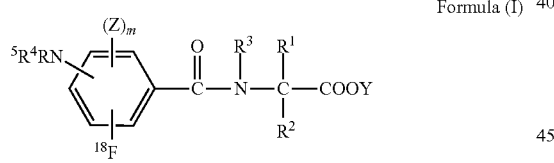

Formula (I)

wherein all the groups are as defined earlier.

The pharmaceutical compositions comprising a compound of formula (I) or a pharmaceutically acceptable salt or solvates or hydrate or stereoisomers thereof in combination with a pharmaceutically acceptable excipient(s) or carrier(s) or diluent(s); and the concentration of said compound of formula (I) is in the range of 0.01% to 99%.

The pharmaceutical compositions comprising a compound of formula (I) or a pharmaceutically acceptable salt or solvates or hydrates or stereoisomers thereof in combination with a pharmaceutically acceptable excipient(s) or carrier(s) or diluent(s); the said carrier or diluent or excipient is selected from the group consisting of glucose, fructose, sucrose, maltose, yellow dextrin, white dextrin, aerosol, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, calcium salts, pigments, flavors and preservatives, distilled water, saline, aqueous glucose solution, alcohol (e.g. ethanol), propylene glycol and polyethylene glycol, various animal and vegetable oils, white soft paraffin, paraffin and wax.

When the compounds of the present invention are administered as diagnostic agents, to humans and animals, they can be given per se or as a pharmaceutical composition containing, for example, 0.01 to 99.5% of a compound of formula (I) in combination with a pharmaceutically acceptable carrier or diluent.

In some methods, while synthesizing the $^{18}F$ compounds of formula (I) with cyclotron generated $^{18}F^-$, in general, the reaction will not give 100% radiochemical purity and small quantities of $^{19}F$ compounds of formula (Ia) will exists. This mixture having $^{18}F$ compounds of formula (I) and the corresponding stable $^{19}F$ compound (Ia) along with their precursor compounds can also be useful for kidney function determination by PET without further purification.

Formula (Ia)

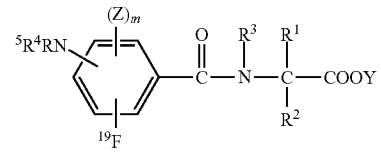

wherein;
Y is independently selected from hydrogen, $C_{1-6}$alkyl, $C_{1-6}$secondaryalkyl, $C_{1-6}$tertiaryalkyl, $C_{2-6}$alkenyl, $C_{2-6}$alkynyl, halo$C_{1-6}$alkyl, hydroxy$C_{1-6}$alkyl, $C_{3-7}$cycloalkyl, $C_{1-6}$alkylamino$C_{1-6}$alkyl, di($C_{1-6}$alkyl)amino$C_{1-6}$alkyl, $C_{1-6}$alkylaryl, $C_{1-6}$alkylheteroaryl, $C_{1-6}$alkylcarboxylic acid, $C_{1-6}$alkylcarboxamide and a aryl, heteroaryl, $C_{1-6}$alkylaryl, $C_{1-6}$alkylheteroaryl and heterocycloalkyl ring; aryl, heteroaryl and heterocycloalkyl ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl; wherein halogen is selected from all isotopes of F, Cl, Br and I;
Z is independently selected from hydrogen, halogen, astatine (At), hydroxy, formyl, carboxylic acid, amino, nitro, cyano, sulfonic acid, thiole, trihalomethyl, sulfonamide, $C_{1-6}$alkyl, $C_{1-6}$secondaryalkyl, $C_{1-6}$tertiaryalkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl, and a aryl, heteroaryl, $C_{1-6}$alkylaryl, $C_{1-6}$alkylheteroaryl and heterocycloalkyl ring; aryl, heteroaryl and heterocycloalkyl ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl; wherein halogen is selected from all isotopes of F, Cl, Br and I;

m is 0, 1, 2 or 3

$R^1$ is independently selected from hydrogen, halogen, astatine (At), $C_{1-6}$alkyl, $C_{1-6}$secondaryalkyl, $C_{1-6}$tertiaryalkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl, mercapto$C_{1-6}$alkyl, $C_{1-6}$alkylmercapto$C_{1-6}$alkyl, $C_{1-6}$alkylaryl, $C_{1-6}$alkylheteroaryl, $C_{1-6}$alkylcarboxylic acid, $C_{1-6}$alkylcarboxamide, $C_{1-6}$alkylguanidine, $C_{1-6}$alkylselenol and a aryl, heteroaryl, $C_{1-6}$alkylaryl, $C_{1-6}$alkylheteroaryl and heterocycloalkyl ring; aryl, heteroaryl and heterocycloalkyl ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl; wherein halogen is selected from all isotopes of F, Cl, Br and I;

$R^2$ is independently selected from hydrogen, halogen, astatine (At), $C_{1-6}$alkyl, $C_{1-6}$secondaryalkyl, $C_{1-6}$tertiaryalkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl, mercapto$C_{1-6}$alkyl, $C_{1-6}$alkylmercapto$C_{1-6}$alkyl, $C_{1-6}$alkylaryl, $C_{1-6}$alkylheteroaryl, $C_{1-6}$alkylcarboxylic acid, $C_{1-6}$alkylcarboxamide, $C_{1-6}$alkylguanidine, $C_{1-6}$alkylselenol and a aryl, heteroaryl, $C_{1-6}$alkylaryl, $C_{1-6}$alkylheteroaryl and heterocycloalkyl ring; aryl, heteroaryl and heterocycloalkyl ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl; wherein halogen is selected from all isotopes of F, Cl, Br and I;

$R^3$ is independently selected from hydrogen, $C_{1-6}$alkyl, halo$C_{1-6}$alkyl, halo$C_{1-6}$alkoxy, $C_{3-7}$cycloalkyl;

$R^1$ and $R^3$ optionally $R^1$ and $R^3$ are joined, and taken together with the atoms to which they are attached, form a 5- to 7-membered heterocycloalkyl ring; the heteroatom is N;

$R^4$ and $R^5$ is independently selected from hydrogen, oxygen, formyl, amino, $C_{1-6}$alkyl, $C_{1-6}$secondaryalkyl, $C_{1-6}$tertiaryalkyl, $C_{2-6}$alkenyl, $C_{2-6}$alkynyl, $C_{1-4}$alkylcarbonyl, aminocarbonyl, $C_{1-6}$ alkylaminocarbonyl, di($C_{1-6}$alkyl)aminocarbonyl, halo$C_{1-6}$alkyl, hydroxy$C_{1-6}$alkyl, $C_{3-7}$cycloalkyl, $C_{1-6}$alkylamino, di($C_{1-6}$alkyl)amino, amino$C_{1-6}$alkyl, $C_{1-6}$alkylamino$C_{1-6}$alkyl, di($C_{1-6}$alkyl)amino$C_{1-6}$alkyl, and a aryl, heteroaryl and heterocycloalkyl ring; aryl, heteroaryl, $C_{1-6}$alkylaryl, $C_{1-6}$alkylheteroaryl and heterocycloalkyl ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl; wherein halogen is selected from all isotopes of F, Cl, Br and I;

Thus, the invention also provides compositions comprising at least one $^{18}$F-compound of formula (I) or their pharmaceutically acceptable salt or solvates or hydrates or stereo-isomers thereof and at least one $^{19}$F-compound of formula (Ia) or their pharmaceutically acceptable salt or solvates or hydrates or stereo-isomers thereof and in combination with a pharmaceutically acceptable excipient(s) or carrier(s) or diluent(s).

Methods of Use

The compounds of the present invention may be used to diagnose kidney function or monitoring kidney function. Therefore, the compounds of formula (I) are expected to be valuable as diagnostic agents. Accordingly, the present invention provides a method of diagnosing kidney function in a warm blooded animal in need thereof, wherein said method comprises administering to the said warm blooded animal a diagnostic amount of at least one compound of formula (I) or its pharmaceutical salt or isomers or hydrates or solvates thereof;

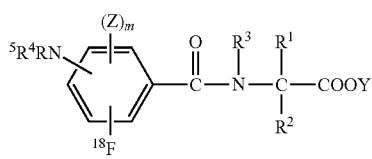

Formula (I)

wherein all the groups are as defined above.

The invention also provides the method of diagnostic imaging or monitoring kidney function comprising the steps of (i) administering at least one compound of formula (I) in a diagnostic amount, and (ii) performing diagnostic imaging using PET by detecting a signal from said at least one compound.

The said warm blooded animal is selected from mammals and birds.

The inventive compounds of formula (I) are useful as an imaging agent for diagnosing or monitoring kidney function in a warm blooded animal.

The invention also provides the method of diagnostic imaging or monitoring kidney function comprising the steps of (i) administering a composition comprising at least one $^{18}$F compound of formula (I), pharmaceutically acceptable salt or solvates or hydrates or stereoisomers thereof in combination with a pharmaceutically acceptable excipient(s) or carrier(s) or diluent(s) in a diagnostic amount, and (ii) performing diagnostic imaging using PET by detecting a signal from said $^{18}$F compound of formula (I).

The invention also provides the method of diagnostic imaging or monitoring kidney function comprising the steps of (i) administering a composition comprising at least one compound of formula (I), pharmaceutically acceptable salt or solvates or hydrates or stereoisomers thereof in combination with a pharmaceutically acceptable excipient(s) or carrier(s) or diluent(s) and $^{19}$F compound of formula (Ia) in a diagnostic amount, and (ii) performing diagnostic imaging using PET by detecting a signal from said $^{18}$F compound of formula (I).

The method of diagnosing kidney function using positron emission tomography (PET) comprises recording multiple consecutive and dynamic images during the passage of 18F compound of formula (I) through the kidney (s).

In a preferred embodiment, the method includes assessing the kidney function either in the normal state or diseased state.

In another preferred embodiment, the method includes assessing the kidney function on transplanted organ for its rejection or acceptance by the host.

In yet another preferred embodiment, the method includes assessing the kidney function in a normal, diseased and transplanted state of children for pediatric usage.

In yet another preferred embodiment, the method includes assessing the kidney function in a normal, diseased and transplanted state of adults.

In yet another preferred embodiment, the method includes assessing the kidney function in a normal, diseased and transplanted state of older adults for geriatric usage.

In yet another embodiment, the invention provides use of the compounds of formula (I) for diagnostic imaging or monitoring kidney function comprising the steps of (i) administering at least one compound of formula (I) in a diagnostic amount, and (ii) performing diagnostic imaging using PET by detecting a signal from said at least one compound.

In yet another embodiment, the invention also provides use of a composition comprising at least one $^{18}$F compound of formula (I), pharmaceutically acceptable salt or solvates or hydrates or stereoisomers thereof in combination with a pharmaceutically acceptable excipient(s) or carrier(s) or diluent(s) in a diagnostic amount, and performing diagnostic imaging using PET by detecting a signal from said $^{18}$F compound of formula (I).

In yet another embodiment, the invention also provides use of a composition comprising at least one $^{18}$F compound of formula (I), pharmaceutically acceptable salt or solvates or hydrates or stereoisomers thereof in combination with a pharmaceutically acceptable excipient(s) or carrier(s) or diluent(s) and $^{19}$F compound of formula (Ia) in a diagnostic amount, and performing diagnostic imaging using PET by detecting a signal from said $^{18}$F compound of formula (I).

In a preferred embodiment, the use includes assessing the kidney function either in the normal state or diseased state; assessing the kidney function on transplanted organ for its rejection or acceptance by the host; and assessing the kidney function in a normal, diseased and transplanted state of children for pediatric usage.

The present invention is provided by the examples given below, which are provided by the way of illustration only, and should not be considered to limit the scope of the invention. Variation and changes, which are obvious to one skilled in the art, are intended to be within the scope and nature of the invention, which are defined in the appended claims.

EXAMPLES

Abbreviations and Acronyms

AcOH=acetic acid; Ac$_2$O=acetic anhydride; anhyd=anhydrous; Bn=benzyl; Boc=tert-butyloxycarbonyl; br s=broad singlet; d=doublet; dd=double doublet; DMSO=dimethylsulfoxide; DCC=dicyclohexylcarbodiimide; DMAP=4-(dimethylamino)-pyridine; DCM=dichloromethane; EtOAc=ethyl acetate; g=gram(s); h=hour(s); HCl=hydrochloric acid; H$_2$SO$_4$=sulfuric acid; HMPA=hexamethylphosphoramide; J=coupling constant; KF=potassium fluoride; K$_2$Cr$_2$O$_7$=potassium dichromate; LC-MS=liquid chromatography-coupled mass spectroscopy; MHz=mega hertz; mmol=millimoles; mL=milliliter(s); mp=melting point; m=multiplet; Na$_2$SO$_4$=sodium sulfate; Na$_2$CO$_3$=sodium carbonate; NMP=N-methyl-2-pyrrolidone; PTS=p-toluenesulfonate; PET=positron emission tomography; PMB=4-methoxybenzyl; Pd/C=palladium on carbon; PEG=polyethylene glycol; rt=room temperature; s=singlet; SOCl$_2$=thionyl chloride; t=triplet; THF=tetrahydrofuran; δ=chemical shift in ppm with reference to tetramethylsilane.

Radiolabeling Protocol

Fluorine-18 fluoride ion was produced by a customary proton irradiation of 0-18 water and subsequently captured on a small ion exchange resin column (strongly basic ion exchange resin, 10-12 mg, 100-200 mesh, hydroxide form). Resin captured activity was eluted with 0.1M aqueous potassium carbonate (99.995%, 0.20 mL, 20 micromol) onto Kryptofix cryptand[2.2.2] (15.1 mg, 40 micromol) in a open glass test tube (3 mL). Activity was rendered anhydrous by customary azeotropic distillations with acetonitrile (MeCN, 3×1 mL) at 90° C., under a rapid stream of argon. The oily residue was solubilized in dry DMSO (0.50 mL) with brief heating (2 min) at 90° C. The solution (94% of total eluted from the resin column) was equally split to label the precursor compounds of formula (I).

Low volume (0.8 mL) glass V-vials, with teflon septa and caps, were used for labeling. Separate vials, containing DMSO solutions (0.25 mL) of compounds of formula (III) (10 micromol), were charged with equal portions of DMSO solubilized radioactivity (0.25 mL; 20 micromol Kryptofix; 10 micromol K$_2$CO$_3$), then sealed and thermostated at 120° C. for 10 min or at 170° C. for 30 min. For each vial, the crude reaction mixture was next diluted with dry MeCN. The solution was sucked through a neutral alumina SepPak (Waters Corp), followed by vial rinses (MeCN: 2 mL), via cannula, into a plastic Leurlok syringe. The SepPak was disconnected and water (1.5 mL) was also pulled into the syringe. The mixture was (<4.5 mL) was loaded into a injector (5 mL loop) and purified on a semi-preparative C18 column (250×10 mm (id)), eluted with 50% MeCN: 50% 15 mM aqueous H$_3$PO$_4$ (pH 2), with gamma detection. The selected product eluate fraction (10-15 mL) was diluted with water (30 mL) and the solution was extracted with a single C18 SepPak (Millipore).

Subsequently, the SepPak was washed with water (3 mL) and flushed with air, followed by elution of trapped activity with methanol (MeOH, 0.5 mL).

Eluted activity was transferred, by syringe, into an argon purged, septum sealed V-vial (0.8 mL), charged with 10% Pd on charcoal (2.5 mg), methanol (0.2 mL) and aqueous 1 N HCl (20 microliters). Argon was used to purge the vial for 1 min using septum piercing needles for inlet and outlets. Hydrogenation was initiated and continued at room temperature by switching the gas to a bubbling stream of hydrogen, sufficient to suspend the catalyst. After 10 minutes, the vial contents were transferred and filtered over a low volume, steel syringe frit, which was subsequently rinsed with methanol. Labeled product identity and radiochemical purity was performed with a calibrated HPLC system equipped with serial gamma and UV detectors.

Synthesis of Intermediates or Precursor Compounds

Intermediate 1: Benzyl 2-(2,4-dinitrobenzamido)acetate

To a solution of benzyl glycinate.PTS salt (1.589 g, 4.716 mmol) in chloroform (20 mL) was added triethylamine (1.95 mL, 14. 148 mmol) at ice cold temperature. A solution of 2,4-dinitrobenzoyl chloride (prepared from 2,4-dinitrobenzoic acid, 1.0 g and $SOCl_2$, 10 mL, refluxed for 2 h and evaporated the solvents) in chloroform (5 mL) was added to the above solution for 10 min and stirred for 1 h. After completion of the reaction, it was diluted with chloroform (100 mL). The chloroform layer was washed with water (2×50 mL), brine (50 mL) and dried over anhyd $Na_2SO_4$. The solution was filtered and evaporated the solvent. The residue was chromatographed over silica gel column using chloroform:methanol (98:02) as eluents to give the product as an off-white color solid (1.55 g, 92%), mp 116-118° C. $^1$H NMR (400 MHz, $CDCl_3$): δ 8.91 (1H, d, J=2.0 Hz), 8.52 (1H, dd, J=8.2, 2.2 Hz), 7.77 (1H, d, J=8.4 Hz), 7.38 (5H, s), 6.52-6.55 (1H, m), 5.24 (2H, s), 4.31 (2H, d, J=5.2 Hz); LC-MS (negative ion mode): m/z 358 (M−H)$^-$.

Intermediate 2: 2-(2,4-dinitrobenzamido)acetic acid

To an ice cold suspension of glycine (1.01 g, 13.56 mmol) in water (20 mL) was added $Na_2CO_3$ (1.437 g, 13.56 mmol) and stirred for 10 min. A solution of 2,4-dinitrobenzoyl chloride (prepared from 2,4-dinitrobenzoic acid, 2.3 g with $SOCl_2$, 20 mL) in dioxane (20 mL) was added to the above solution and stirred at rt for 4 h. The reaction mixture was diluted with ice cold water and acidified with cold dil. HCl (pH: 6.0). The solution was extracted with EtOAc (5×100 mL) and the combined organic layer was dried over anhyd $Na_2SO_4$ and filtered. The solution was evaporated and the residue was chromatographed over silica gel column using chloroform:methanol (95:5) as eluents to give the product as a white color solid (2.5 g, 85%), mp 188-190° C. $^1$H NMR (400 MHz, DMSO-$d_6$): δ 12.79 (1H, br s), 9.29 (1H, t, J=5.4 Hz), 8.77 (1H, d, J=2.0 Hz), 8.64 (1H, dd, J=8.4, 2.0 Hz), 7.89 (1H, d, J=8.4 Hz), 3.99 (2H, d, J=6.0 Hz); LC-MS (negative ion mode): m/z 268 (M−H)$^-$.

Intermediate 3: Benzyl 2-(3,4-dinitrobenzamido)acetate

The reaction of 3,4-dinitrobenzoyl chloride (prepared from 3,4-dinitrobenzoic acid, 500 mg and $SOCl_2$, 10 mL) with benzyl glycinate.PTS salt (794 mg, 2.358 mmol) in the presence of triethylamine (1.0 mL, 7.07 mmol) as described in intermediate 1 gave the title compound as an yellow color solid (780 mg, 92%), mp 150-152° C. $^1$H NMR (400 MHz, $CDCl_3$): δ 8.37 (1H, br s), 8.17 (1H, d, J=8.0 Hz), 8.00 (1H, d, J=7.6 Hz), 7.39 (5H, s), 6.79 (1H, br s), 5.26 (2H, s), 4.31 (2H, d, J=4.0 Hz); LC-MS (negative ion mode): m/z 358 (M−H)$^-$.

Intermediate 4: Benzyl 2-(2-chloro-4,5-dinitrobenzamido)acetate

A mixture of benzyl N-Bocglycinate (3 g, 11.3 mmol) and HCl in dioxane (20 mL) was stirred at rt for 2 h. Solvents were evaporated under reduced pressure and was diluted with dioxane (20 mL) and triethylamine (2.24 mL, 16.24 mmol). Then 2-chloro-4,5-dinitrobenzoic acid (2 g, 8.1 mmol) was added and cooled to 5° C. A solution of DCC (5.8 g, 28.1 mmol) in dioxane (20 mL) was added followed by catalytic amount of DMAP. The reaction mixture was stirred at rt for 5 h. Few drops of water was added to the reaction mixture and again stirred for 15 min. Reaction mixture was cooled to 0° C. and filtered. The solid was washed with ether (50 mL) and EtOAc (50 mL). The filtrate was poured into water and the organic layer was separated. The aqueous layer was extracted with EtOAc (3×100 mL) and the combined organic layer was washed with brine and dried over anhyd $Na_2SO_4$. The solution was filtered and evaporated the solvent. The residue was chromatographed over silica gel column using chloroform:acetone (90:10) as eluents to give the product as a pale yellow color solid (2.5 g, 75%), mp 122-124° C. $^1$H NMR (400 MHz, $CDCl_3$): δ 8.30 (1H, s), 7.96 (1H, s), 7.39 (5H, s), 6.94 (1H, br s), 5.25 (2H, s), 4.32 (2H, d, J=4.8 Hz); LC-MS (negative ion mode): m/z 392 (M−H)$^-$.

Intermediate 5: Benzyl 2-(4-chloro-3-nitrobenzamido)acetate

The reaction of 4-chloro-3-nitrobenzoyl chloride (prepared from 4-chloro-3-nitrobenzoic acid, 1.0 g and $SOCl_2$, 10 mL) with benzyl glycinate.PTS salt (2.0 g, 5.9 mmol) in the presence of triethylamine (2.0 mL, 14.88 mmol) as described in intermediate 1 gave the title compound as a pale green color solid (1.38 g, 80%), mp 84-86° C. $^1$H NMR (400 MHz, $CDCl_3$): δ 8.31 (1H, d, J=2.0 Hz), 7.95 (1H, dd, J=8.4, 2.0 Hz), 7.65 (1H, d, J=8.4 Hz), 7.38 (5H, br s), 6.73 (1H, br s), 5.24 (2H, s), 4.29 (2H, d, J=4.8 Hz); LC-MS (negative ion mode): m/z 347 (M−H)$^-$.

Intermediate 6: Benzyl 2-(2-chloro-5-nitrobenzamido)acetate

The reaction of 2-chloro-5-nitrobenzoyl chloride (prepared from 2-chloro-5-nitrobenzoic acid, 1.0 g and $SOCl_2$, 10 mL) with benzyl glycinate.PTS salt (1.9 g, 5.9 mmol) in the presence of triethylamine (2.0 mL, 14.88 mmol) as described in intermediate 1 gave the title compound as a colorless solid (1.42 g, 82%), mp 116-118° C. $^1$H NMR (400 MHz, $CDCl_3$): δ 8.54 (1H, d, J=2.8 Hz), 8.23 (1H, dd, J=8.6, 2.6 Hz), 7.61 (1H, d, J=8.8 Hz), 7.38 (5H, br s), 6.88 (1H, br s), 5.24 (2H, s), 4.32 (2H, d, J=4.8 Hz); LC-MS (positive ion mode): m/z 349, 351 (M+H)$^+$.

Intermediate 7: Benzyl 2-(3-iodyl-4-nitrobenzamido)acetate

Step 1:

Benzyl 2-(3-iodo-4-nitrobenzamido)acetate: To a solution of benzyl N-Boc glycinate (678 mg, 2.55 mmol) in dioxane (20 mL) was added HCl in dioxane (2N, 5 mL) at rt and stirred for 2 h. Solvents were evaporated under reduced pressure. The residue was dissolved in dioxane (20 mL) and triethylamine (0.47 ml, 3.4 mmol) was added. 3-Iodo-4-nitrobenzoic acid (500 mg, 1.70 mmol) and a solution of DCC (703 mg, 3.4 mmol) in dioxane (20 mL) followed by catalytic amount of DMAP were added successively to the reaction mixture at ice cold temperature. The mixture was stirred at rt for 5 h and worked-up as described in intermediate 4 to give the product as a cream color solid (590 mg, 79%), mp 98-100° C. $^1$H NMR (400 MHz, CDCl$_3$): δ 8.43 (1H, s), 7.87 (2H, br s), 7.38 (5H, br s), 6.84 (1H, br s), 5.24 (2H, s), 4.28 (2H, d, J=4.8 Hz); LC-MS (negative ion mode): m/z 439 (M−H)$^−$.

Step 2:

Benzyl 2-(3-iodyl-4-nitrobenzamido)acetate: A mixture of Ac$_2$O (4 mL) and H$_2$O$_2$ (1 mL, 50%) was heated at 40° C. for 4 h. Benzyl 2-(3-iodo-4-nitrobenzamido)acetate (1 g) was added to the reaction mixture at the same temperature and stirred for 20 h. After completion of reaction, it was poured into ice-cold water and stirred for 15 min. The precipitated solid was filtered, washed with cold water and dried to give the product as a yellow color solid (920 mg, 86%), mp 196-198° C. $^1$H NMR (400 MHz, DMSO-d$_6$): δ 9.56 (1H, t, J=5.4 Hz), 8.72 (1H, br s), 8.49 (1H, d, J=8.4 Hz), 8.26 (1H, d, J=8.0 Hz), 7.32-7.40 (5H, m), 5.19 (2H, s), 4.16 (2H, d, J=5.6 Hz); LC-MS (positive ion mode): m/z 495 (M+Na)$^+$.

Intermediate 8: 2,2,2-Trichloroethyl 2-(3-iodyl-4-nitrobenzamido)acetate

Step 1:

2,2,2-Trichloroethyl 2-(3-iodo-4-nitrobenzamido)acetate: To a stirred solution 2,2,2-trichloroethyl N-Boc glycinate (1.25 g, 4.08 mmol) in DCM (10 mL) was added HCl in dioxane (2N, 10 mL) and stirred at rt for 2 h. Solvents were removed under reduced pressure, and was dissolved in DCM (10 mL) and added triethylamine (1.48 mL, 10.23 mmol) at 0° C. A solution of 3-iodo-4-nitrobenzoyl chloride (prepared from 3-iodo-4-nitrobenzoic acid, 1 g and SOCl$_2$, 10 mL) in DCM (10 mL) was added to the above reaction mixture at 0° C. Then the reaction mixture was stirred at rt for 3 h and worked-up as described in intermediate 1 to obtain the product as a cream color solid (1.28 g, 78%), mp 98-100° C. $^1$H NMR (400 MHz, CDCl$_3$): δ 8.46 (1H, s), 7.90 (2H, s), 6.67 (1H, br s), 4.86 (2H, s), 4.23 (2H, d, J=5.2 Hz); LC-MS (negative ion mode): m/z 479 (M−H)$^−$.

Step 2:

2,2,2-Trichloroethyl 2-(3-iodyl-4-nitrobenzamido)acetate: A mixture of Ac$_2$O (7 mL) and H$_2$O$_2$ (2 mL, 50%) was heated at 40° C. for 4 h. 2,2,2-Trichloroethyl 2-(3-iodo-4-nitrobenzamido)acetate (1 g) was added at 40° C. to the above mixture and worked-up as described in intermediate 7 to give the product as a pale yellow color solid (900 mg, 85%), mp 128-130° C. $^1$H NMR (400 MHz, DMSO-d$_6$): δ 9.69 (1H, t, J=5.4 Hz), 8.71 (1H, br s), 8.50 (1H, d, J=8.4 Hz), 8.26 (1H, d, J=8.4 Hz), 4.98 (2H, s), 4.26 (2H, d, J=5.2 Hz); LC-MS (positive ion mode): m/z 513 (M+H)$^+$.

Intermediate 9: Potassium 2-(3-iodyl-4-nitrobenzamido)acetate

Step 1:

2-(3-Iodo-4-nitrobenzamido)acetic acid: The reaction of 3-iodo-4-nitrobenzoyl chloride (prepared from 3-iodo-4-nitrobenzoic acid, 1.2 g and SOCl$_2$, 10 mL) with glycine (0.38 g, 5.12 mmol) in the presence of Na$_2$CO$_3$ (0.54 g, 5.12 mmol) as described in intermediate 2 gave the title compound as a pale yellow color solid (1.3 g, 91%), mp 140-142° C. $^1$H NMR (400 MHz, DMSO-d$_6$): δ 12.69 (1H, br s), 9.19 (1H, t, J=5.6 Hz), 8.52 (1H, br s), 8.05 (2H, br s), 3.96 (2H, d, J=6.0 Hz); LC-MS (negative ion mode): m/z 349 (M−H)$^−$.

Step 2:

Potassium 2-(3-iodyl-4-nitrobenzamido)acetate: A mixture of Ac$_2$O (3 mL) and H$_2$O$_2$ (0.8 mL, 50%) was heated at 40° C. for 4 h. 2-(3-Iodo-4-nitrobenzamido)acetic acid (170 mg) was added at 40° C. to the above mixture and worked-up as described in intermediate 7 to give the product as a cream color solid (142 mg, 77%), mp 186-188° C. (decomposed). $^1$H NMR (400 MHz, DMSO-d$_6$): δ 12.71 (1H, br s), 9.44 (1H, br s), 8.70 (1H, br s), 8.49 (1H, d, J=7.2 Hz), 8.25 (1H, d, J=7.4 Hz), 3.99 (2H, br s); LC-MS (negative ion mode): m/z 381 (M−H)$^−$. A mixture of the above compound, KOH (20 mg, 0.37 mmol) and dry methanol (10 mL) was stirred at 60-65° C. under nitrogen atmosphere for 30 min. The reaction mixture was cooled and the precipitated solid was filtered, washed with dry methanol and dried to give the product as a cream color solid (125 mg, 80%), mp 205-207° C. (decomposed). $^1$H NMR (400 MHz, D$_2$O): δ 8.67 (1H, br s), 8.59 (1H, d, J=9.2 Hz), 8.33 (1H, d, J=8.4 Hz), 3.98 (2H, s); LC-MS (positive ion mode): m/z 421 (M+H)$^+$.

Intermediate 10: 2-(2,6-Dinitrobenzamido)acetic acid

Step 1:

2,6-Dinitrobenzoic acid: To an ice cold (0° C.) solution of H$_2$SO$_4$ (7 mL, 98%) was added 2,6-dinitrotoluene (1.0 g, 5.49 mmol) followed by slow addition of K$_2$Cr$_2$O$_7$ (1.72 g, 5.835 mmol) below 30° C. for 1 h. The reaction mixture was stirred at rt for 20 h. The mixture was poured into ice cooled water (200 mL) and stirred for 5 min. The solution was extracted with EtOAc (3×50 mL). The combined solution was dried over anhyd Na$_2$SO$_4$. The solution was filtered and evaporated the solvents. The residue was chromatographed over silica gel column using chloroform:methanol (80:20) as eluents to give the product as a pale yellow color solid (690 mg, 60%), mp 200-202° C. $^1$H NMR (400 MHz, DMSO-d$_6$): δ 8.52 (2H, d, J=8.4 Hz), 7.98 (1H, t, J=8.2 Hz); LC-MS (negative ion mode): m/z 211 (M−H)$^−$.

Step 2:

2-(2,6-Dinitrobenzamido)acetic acid: The reaction of 2,6-dinitrobenzoyl chloride (prepared from 2,6-dinitrobenzoic acid, 1.2 g and SOCl$_2$, 20 mL) with glycine (530 mg, 7.075 mmol) in the presence of Na$_2$CO$_3$ (749 mg, 7.075 mmol) as described in intermediate 2 gave the title compound as an off-white color solid (1.2 g, 80%), mp 210-212° C. $^1$H NMR (400 MHz, DMSO-d$_6$): δ 12.76 (1H, s), 9.22 (1H, t, J=5.0 Hz), 8.45 (2H, d, J=8.4 Hz), 7.93 (1H, t, J=8.4 Hz), 3.98 (2H, d, J=5.2 Hz); LC-MS (negative ion mode): m/z 268 (M−H)$^−$.

Intermediate 11: (S)-2-(2,4-Dinitrobenzamido)propanoic acid

The reaction of 2,4-dinitrobenzoyl chloride (prepared from 2,4-dinitrobenzoic acid, 2 g and SOCl$_2$, 20 mL) with L-alanine (1.04 g, 11.79 mmol) in the presence of Na$_2$CO$_3$ (1.24 g, 11.79 mmol) as described in intermediate 2 gave the title compound as an off-white color solid (2.08 g, 78%), mp 194-196° C. $^1$H NMR (400 MHz, DMSO-d$_6$): δ 12.77 (1H, s), 9.25 (1H, d, J=7.6 Hz), 8.77 (1H, d, J=2.0 Hz), 8.63 (1H, dd, J=8.4, 2.0 Hz), 7.87 (1H, d, J=8.4 Hz), 4.44 (1H, pentet, J=7.3 Hz), 1.38 (3H, d, J=7.2 Hz); LC-MS (negative ion mode): m/z 282 (M−H)$^−$.

Intermediate 12:
(R)-2-(2,4-Dinitrobenzamido)propanoic acid

The reaction of 2,4-dinitrobenzoyl chloride (prepared from 2,4-dinitrobenzoic acid, 2 g and $SOCl_2$, 20 mL) with D-alanine (1.04 g, 11.79 mmol) in the presence of $Na_2CO_3$ (1.24 g, 11.79 mmol) as described in intermediate 2 gave the title compound as an off-white color solid (2.18 g, 82%), mp 192-194° C. $^1$H NMR (400 MHz, DMSO-$d_6$): δ 12.92 (1H, br s), 9.32 (1H, d, J=7.2 Hz), 8.83 (1H, d, J=1.6 Hz), 8.69 (1H, dd, J=8.2, 1.4 Hz), 7.93 (1H, d, J=8.4 Hz), 4.49 (1H, pentet, J=7.2 Hz), 1.44 (3H, d, J=7.2 Hz); LC-MS (negative ion mode): m/z 282 (M–H)$^-$.

Intermediate 13:
(S)-2-(2,6-Dinitrobenzamido)propanoic acid

The reaction of 2,6-dinitrobenzoyl chloride (prepared from 2,6-dinitrobenzoic acid, 1 g and $SOCl_2$, 10 mL) with L-alanine (0.52 g, 5.895 mmol) in the presence of $Na_2CO_3$ (0.625 g, 5.895 mmol) as described in intermediate 2 gave the title compound as a pale brown color solid (1.06 g, 80%), mp 222-224° C. $^1$H NMR (400 MHz, DMSO-$d_6$): δ 12.81 (1H, br s), 9.23 (1H, d, J=7.6 Hz), 8.45 (2H, d, J=8.4 Hz), 7.92 (1H, t, J=8.2 Hz), 4.47 (1H, pentet, J=7.2 Hz), 1.33 (3H, d, J=7.2 Hz); LC-MS (negative ion mode): m/z 282 (M–H)$^-$.

Intermediate 14:
(R)-2-(2,6-Dinitrobenzamido)propanoic acid

The reaction of 2,6-dinitrobenzoyl chloride (prepared from 2,6-dinitrobenzoic acid, 1.4 g and $SOCl_2$, 15 mL) with D-alanine (0.7 g, 7.92 mmol) in the presence of $Na_2CO_3$ (0.83 g, 7.92 mmol) as described in intermediate 2 gave the title compound as a pale brown color solid (1.58 g, 85%), mp 202-204° C. $^1$H NMR (400 MHz, DMSO-$d_6$): δ 12.79 (1H, br s), 9.24 (1H, d, J=7.6 Hz), 8.45 (2H, d, J=8.4 Hz), 7.93 (1H, t, J=8.4 Hz), 4.48 (1H, pentet, J=7.3 Hz), 1.33 (3H, d, J=7.2 Hz); LC-MS (negative ion mode): m/z 282 (M–H)$^-$.

Preparation Examples

Example 1

2-(4-amino-2-(18)fluorobenzamido)acetic acid (compound 1)

Method A ($K^{19}F/H_2$—Pd—C)

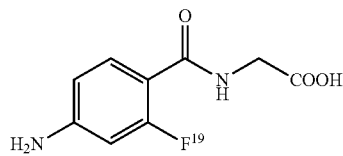

Step 1:
Benzyl 2-(2-fluoro-4-nitrobenzamido)acetate: A mixture of spray-dried KF (200 mg, 3.48 mmol), intermediate 1 (250 mg, 0.696 mmol) and catalytic amount of 18-crown-6 in dry DMSO (5 mL) was stirred at 140-150° C. for 30 min. After completion (TLC), the reaction mixture was poured into ice cooled water (100 mL) and stirred for 5 min. The solution was extracted with EtOAc (3×50 mL). The combined solution was dried over anhyd $Na_2SO_4$. The solution was filtered and evaporated the solvents. The residue was chromatographed over silica gel column using hexane:acetone (80:20) as eluents to give the product as a pale yellow color solid (106 mg, 46%), mp 104-106° C. $^1$H NMR (400 MHz, CDCl$_3$): δ 8.30 (1H, t, J=8.0 Hz), 8.13 (1H, dd, J=8.6, 1.4 Hz), 8.04 (1H, dd, J=11.0, 1.8 Hz), 7.38 (5H, s), 5.25 (2H, s), 4.33 (2H, d, J=4.8 Hz); LC-MS (negative ion mode): m/z 331 (M–H)$^-$.

Step 2:
2-(4-Amino-2-fluorobenzamido)acetic acid: To a solution of benzyl 2-(2-fluoro-4-nitrobenzamido)acetate (100 mg) in EtOAc (10 mL) was added Pd/C (10%, 100 mg) at rt and stirred under the atmosphere of $H_2$ gas for 30 min. The reaction mixture was filtered and washed with EtOAc (2×5 mL). The residue obtained after evaporation of the solvents was recrystallized from EtOAc to give the product as a white color solid (50 mg, 79%), mp 194-196° C. $^1$H NMR (400 MHz, DMSO-$d_6$): δ 12.53 (1H, br s), 7.74-7.78 1H, m), 7.52 (1H, t, J=8.8 Hz), 6.42 (1H, dd, J=8.4, 1.6 Hz), 6.31 (1H, d, J=14.4 Hz), 5.99 (2H, s), 3.90 (2H, d, J=5.6 Hz); $^{13}$C NMR (100 MHz, DMSO-$d_6$): δ 171.3, 163.4 (d, J=3.0 Hz), 161.7 (d, J=244 Hz), 153.8 (d, J=13.0 Hz), 131.9 (d, J=5.0 Hz), 109.6, 107.8 (d, J=12.0 Hz), 99.1 (d, J=26.0 Hz), 41.3; LC-MS (negative ion mode): m/z 211 (M–H)$^-$.

Method B ($K^{19}F$/Zn-ammonium formate)

Step 1:
2-(2-Fluoro-4-nitrobenzamido)acetic acid: A mixture of spray-dried KF (431 mg, 7.434 mmol), intermediate 2 (200 mg, 0.7434 mmol) and catalytic amount of 18-crown-6 in dry DMSO (6 mL) was stirred at 170-180° C. for 30 min. After completion (TLC), the reaction mixture was poured into ice cooled water (100 mL) and acidified with dil HCl. The solution was extracted with EtOAc (3×50 mL). The combined solution was washed with brine and dried over anhyd $Na_2SO_4$. The solution was filtered and evaporated the solvents. The residue was chromatographed over silica gel column using chloroform:methanol (95:5) as eluents to give the product as an off-white color solid (110 mg, 61%), mp 156-158° C. $^1$H NMR (400 MHz, DMSO-$d_6$): δ 12.73 (1H, br s, exchangeable with $D_2O$), 8.94 (1H, s, exchangeable with $D_2O$), 8.23 (1H, d, J=9.2 Hz), 8.16 (1H, d, J=8.0 Hz), 7.88 (1H, t, J=7.4 Hz), 3.97 (2H, d, J=4.8 Hz); $^{13}$C NMR (100 MHz, DMSO-$d_6$): δ 170.5, 162.5, 158.6 (d, J=253 Hz), 149.3 (d, J=8 Hz), 131.4 (d, J=3 Hz), 129.4 (d, J=15 Hz), 119.6 (d, J=4 Hz), 112.1 (d, J=28 Hz), 41.3; LC-MS (negative ion mode): m/z 241 (M–H)$^-$.

Step 2:
2-(4-Amino-2-fluorobenzamido)acetic acid: To a solution of 2-(2-fluoro-4-nitrobenzamido)acetic acid (100 mg, 0.413 mmol) in methanol (15 mL) was added successively zinc dust (270 mg, 4.132 mmol) and ammonium formate (260 mg, 4.132 mmol) at rt. The reaction mixture was stirred at rt for 15 min. The reaction mixture was filtered and washed with methanol (2×5 mL). The residue obtained after evaporation of the solvents was diluted with water (5 mL) and acidified with AcOH (3 mL). The solution was extracted with EtOAc (3×50 mL) and the combined organic layer was dried over anhyd $Na_2SO_4$. The solution was filtered and evaporated the solvent. The residue was chromatographed over silica gel column using chloroform:methanol (70:30) as eluents to give the product as a white color solid (59 mg, 67%), mp 190-194° C.

Method C ($K^{19}F$/Microwave Irradiation)

A mixture of spray-dried KF (80 mg, 1.392 mmol), intermediate 1 (100 mg, 0.2785 mmol) and catalytic amount of 18-crown-6 in dry DMSO (2 mL) was irradiated using house hold microwave oven for 1.5 min. Work-up of the reaction mixture as described in example 1 (method A) gave benzyl 2-(2-fluoro-4-nitrobenzamido)acetate as a pale yellow color solid (106 mg, 46%), mp 104-106° C. Which was further reduced as described in example 1 gave compound 1.

Method D (K$^{18}$F/Pd—C/1,4-Cyclohexadiene)

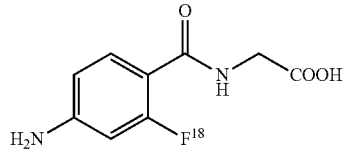

A solution of intermediate-2 in dry DMSO was added to the dry $^{18}$F-fluoride-cryptate complex and heated for 10 min at 120° C. After cooling, water was added and the mixture was passed through reversed phase column (Sep-Pak-C-18 column, waters). The column was washed three times with water and dried 2 min by a stream of nitrogen. The $^{18}$F-labeled compound was eluted with acetonitrile into another sealed reaction vessel and evaporated the solvent. The radiochemical yield of the product is 27% which was reduced as described above with Pd—C/1,4-cyclohexadiene and purification through HPLC. The identity of the compound was determined on an analytical HPLC by co-injection with the corresponding $^{19}$F compound on an analytical HPLC.

Example 2

2-(4-Acetamido-2-(18)fluorobenzamido)acetic acid (compound 2)

Method A (K$^{19}$F/Fe—Ac$_2$O—AcOH)

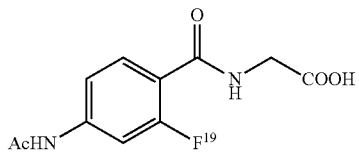

A mixture of spray-dried KF (1.07 g, 18.58 mmol), intermediate 2 (500 mg, 1.858 mmol) and catalytic amount of 18-crown-6 in dry DMSO (8 mL) was stirred at 170-180° C. for 30 min. Work-up of the reaction mixture as described in example 1 gave the residue. This residue was dissolved in a mixture of AcOH and Ac$_2$O (12 mL, 1:1) and added iron powder (2.08 g, 37.17 mmol) at rt. The mixture was stirred at 60-70° C. for 30 min and diluted with EtOAc (25 mL). Filtered the solution to remove iron powder and washed with few mL of EtOAc. Ethyl acetate was removed under reduced pressure. The residue was chromatographed over silica gel column using chloroform:methanol (70:30) as eluents to give the product as a white color solid (160 mg, 34%), mp 240-242° C. $^1$H NMR (400 MHz, DMSO-d$_6$): δ 10.51 (1H, s, exchangeable with D$_2$O), 7.82 (1H, br s, exchangeable with D$_2$O), 7.76 (1H, t, J=8.6 Hz), 7.70 (1H, d, J=14.0 Hz), 7.34 (1H, d, J=8.4 Hz), 3.71 (2H, s), 2.08 (3H, s); LC-MS (negative ion mode): m/z 253 (M−H)$^-$.

Method B (K$^{18}$F/Fe—Ac$_2$O—AcOH)

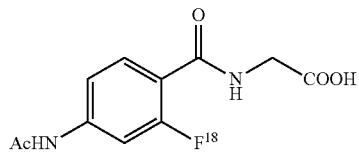

A solution of intermediate-2 in dry DMSO was added to the dry $^{18}$F-fluoride-cryptate complex and heated for 10 min at 120° C. After cooling, water was added and the mixture was passed through reversed phase column (Sep-Pak-C-18 column, waters). The column was washed three times with water and dried 2 min by a stream of nitrogen. The $^{18}$F-labeled compound was eluted with acetonitrile into another sealed reaction vessel and evaporated the solvent. The radiochemical yield of the product is 27% which was reduced with iron powder and acetic anhydride-acetic acid and purification through HPLC. The identity of the compound was determined on an analytical HPLC by co-injection with the corresponding $^{19}$F compound on an analytical HPLC.

Example 3

2-(3-Amino-4-(18)fluorobenzamido)acetic acid (compound 3)

Method A (K$^{19}$F/H$_2$—Pd—C)

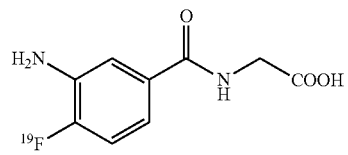

Step 1:
Benzyl 2-(4-fluoro-3-nitrobenzamido)acetate: A mixture of spray-dried KF (80 mg, 1.39 mmol), intermediate 3 (100 mg, 0.27 mmol) and catalytic amount of 18-crown-6 in dry DMSO (4 mL) was stirred at 110-120° C. for 10 min. Work-up of the reaction mixture as described in example 1 gave the product as a pale yellow color solid (51 mg, 55%), mp 84-86° C. $^1$H NMR (400 MHz, CDCl$_3$): δ 8.50 (1H, dd, J=6.8, 1.6 Hz), 8.10-8.13 (1H, m), 7.34-7.39 (6H, m), 6.90 (1H, br s), 5.23 (2H, s), 4.28 (2H, d, J=5.2 Hz); LC-MS (negative ion mode): m/z 331 (M−H)$^-$.
Step 2:
2-(3-Amino-4-fluorobenzamido)acetic acid: To a solution of benzyl 2-(4-fluoro-3-nitrobenzamido)acetate (85 mg) in EtOAc (10 mL) was added Pd/C (10%, 100 mg) at rt and stirred under the atmosphere of H$_2$ gas for 25 min. Work-up of the reaction mixture as described in example 1 gave the product as a white color solid (38 mg, 70%), mp 150-152° C. $^1$H NMR (400 MHz, CDCl$_3$+DMSO-d$_6$): δ 7.74 (1H, br s), 7.37 (1H, dd, J=8.6, 1.8 Hz), 7.12-7.16 (1H, m), 6.97 (1H, dd, J=10.6, 8.6 Hz), 4.07 (2H, d, J=5.6 Hz); $^{13}$C NMR (100 MHz, CDCl$_3$+DMSO-d$_6$): δ 170.6, 165.9, 151. 9 (d, J=242 Hz), 134.5 (d, J=13 Hz), 129.6 (d, J=3 Hz), 115.4 (d, J=8 Hz), 115.1 (d, J=6 Hz), 113.6 (d, J=19 Hz), 40.5; LC-MS (negative ion mode): m/z 211 (M−H)⁻.

Method B (K$^{19}$F/H$_2$—Pd—C)

A mixture of spray-dried KF (261 mg, 4.52 mmol), intermediate 5 (315 mg, 0.90 mmol) and catalytic amount of 18-crown-6 in dry DMSO (10 mL) was stirred at 170-175° C. for 15 min. Work-up of the reaction mixture as described in example 1 gave the product (175 mg, 58%). Which was dissolved in EtOAc (10 mL) and Pd/C (20 mg) was added. Reaction mixture was stirred under the atmosphere of H$_2$ gas at rt for 30 min. Work-up of the reaction mixture as described in example 1 gave the product as a pale brown color solid (72 mg, 64%), mp 192-196° C.

Method C (K$^{18}$F/Pd—C/1,4-cyclohexadiene)

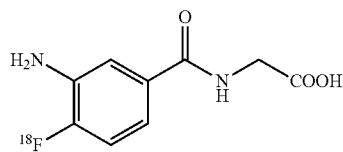 [SMILES: Nc1cc(C(=O)NCC(=O)O)ccc1[19F]]

A solution of intermediate-3 in dry DMSO was added to the dry $^{18}$F-fluoride-cryptate complex and heated for 10 min at 120° C. After cooling, water was added and the mixture was passed through reversed phase column (Sep-Pak-C-18 column, waters). The column was washed three times with water and dried 2 min by a stream of nitrogen. The $^{18}$F-labeled protected compound was eluted with acetonitrile into another sealed reaction vessel and evaporated the solvent. The radiochemical yield of the product is 25% which was reduced with Pd/C and 1,4-cyclohexadiene and purification through HPLC. The identity of the compound was determined on an analytical HPLC by co-injection with the corresponding $^{19}$F compound on an analytical HPLC.

Method D (K$^{18}$F/Pd—C/1,4-cyclohexadiene)

A solution of intermediate-5 in dry DMSO was added to the dry $^{18}$F-fluoride-cryptate complex and heated for 10 min at 120° C. After cooling, water was added and the mixture was passed through reversed phase column (Sep-Pak-C-18 column, waters). The column was washed three times with water and dried 2 min by a stream of nitrogen. The $^{18}$F-labeled protected compound was eluted with acetonitrile into another sealed reaction vessel and evaporated the solvent. The radiochemical yield of the product is 42% which was reduced with Pd/C and 1,4-cyclohexadiene and purification through HPLC. The identity of the compound was determined on an analytical HPLC by co-injection with the corresponding $^{19}$F compound on an analytical HPLC.

Example 4

2-(5-Amino-2-chloro-4-(18)fluorobenzamido)acetic acid (compound 4)

Method A (K$^{19}$F/H$_2$—Pd—C)

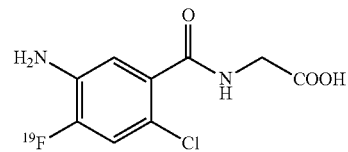 [SMILES: Nc1cc(C(=O)NCC(=O)O)c(Cl)cc1[19F]]

Step 1:

Benzyl 2-(2-chloro-4-fluoro-5-nitrobenzamido)acetate: A mixture of spray-dried KF (736 mg, 12.7 mmol), intermediate 4 (1 g, 2.5 mmol) and catalytic amount of 18-crown-6 in dry acetonitrile (20 mL) was refluxed for 4 h. Work-up of the reaction mixture as described in example 1 gave the product as a pale yellow color solid (580 mg, 62%), mp 108-110° C. $^1$H NMR (400 MHz, CDCl$_3$): δ 8.50 (1H, d, J=8.0 Hz), 7.42 (1H, d, J=10.0 Hz), 7.38 (5H, s), 6.87 (1H, br s), 5.25 (2H, s), 4.31 (2H, d, J=5.2 Hz); LC-MS (negative ion mode): m/z 365 (M−H)⁻.

Step 2:

2-(5-Amino-2-chloro-4-fluorobenzamido)acetic acid: To a solution of benzyl 2-(2-chloro-4-fluoro-5-nitrobenzamido) acetate (190 mg) in EtOAc (10 mL) was added Pd/C (200 mg) and stirred under the atmosphere of H$_2$ gas at 60° C. for 20 min. Work-up of the reaction mixture as described in example 1 gave the product as an off-white solid (86 mg, 67%), mp 225-227° C. (decomposed). $^1$H NMR (400 MHz, DMSO-d$_6$): δ 8.52 (1H, br s), 7.19 (1H, d, J=10.8 Hz), 6.89 (1H, d, J=9.2 Hz), 5.48 (2H, br s), 3.86 (2H, d, J=3.6 Hz); LC-MS (negative ion mode): m/z 245, 247 (M−H)⁻.

Method B (K$^{18}$F/Pd—C/1,4-cyclohexadiene)

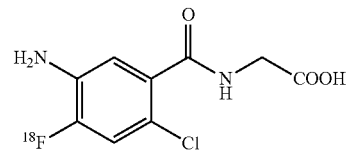

A solution of intermediate-4 in dry DMSO was added to the dry $^{18}$F-fluoride-cryptate complex and heated for 10 min at 120° C. After cooling, water was added and the mixture was passed through reversed phase column (Sep-Pak-C-18 column, waters). The column was washed three times with water and dried 2 min by a stream of nitrogen. The $^{18}$F-labeled protected compound was eluted with acetonitrile into another sealed reaction vessel and evaporated the solvent. The radiochemical yield of the product is 15% which was reduced with Pd/C and 1,4-cyclohexadiene and purification through HPLC. The identity of the compound was determined on an analytical HPLC by co-injection with the corresponding $^{19}$F compound on an analytical HPLC.

Example 5

2-(5-Amino-2-(18)fluorobenzamido)acetic acid (compound 5)

Method A (K$^{19}$F/H$_2$—Pd—C)

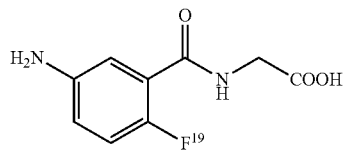

Step 1:

Benzyl 2-(2-fluoro-5-nitrobenzamido)acetate: A mixture of spray dried KF (208 mg, 3.58 mmol), intermediate 6 (250 mg, 0.71 mmol) and catalytic amount of 18-crown-6 in dry DMSO (5 mL) was stirred at 100-110° C. for 45 min. Work-up of the reaction mixture as described in example 1 gave the product as a brown color solid (150 mg, 63%), mp 56-58° C. $^1$H NMR (400 MHz, CDCl$_3$): δ 9.00 (1H, dd, J=6.0, 2.8 Hz), 8.36-8.40 (1H, m), 7.31-7.38 (7H, m), 5.25 (2H, s), 4.34 (2H, d, J=4.4 Hz); LC-MS (negative ion mode): m/z 331 (M−H)$^−$.

Step 2:

2-(5-Amino-2-fluorobenzamido)acetic acid: To a stirred solution of benzyl 2-(2-fluoro-5-nitrobenzamido)acetate (120 mg) in methanol (10 mL) was added Pd/C (100 mg) at rt and stirred under the atmosphere of H$_2$ gas at rt for 30 min. Work-up of the reaction mixture as described in example 1 gave the product as a pale brown color solid (50 mg, 65%), mp 252-254° C. $^1$H NMR (400 MHz, DMSO-d$_6$): δ 7.71-7.73 (1H, m), 7.00-7.02 (1H, m), 6.94 (1H, t, J=10.0 Hz), 6.65-6.67 (1H, m), 5.15 (2H, br s), 3.64 (2H, br s); LC-MS (negative ion mode): m/z 211 (M−H)$^−$.

Method B (K$^{18}$F/Pd—C/1,4-cyclohexadiene)

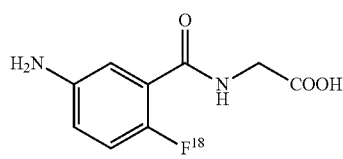

A solution of intermediate-6 in dry DMSO was added to the dry $^{18}$F-fluoride-cryptate complex and heated for 10 min at 120° C. After cooling, water was added and the mixture was passed through reversed phase column (Sep-Pak-C-18 column, waters). The column was washed three times with water and dried 2 min by a stream of nitrogen. The $^{18}$F-labeled protected compound was eluted with acetonitrile into another sealed reaction vessel and evaporated the solvent. The radiochemical yield of the product is 45% which was reduced with Pd/C and 1,4-cyclohexadiene and purification through HPLC. The identity of the compound was determined on an analytical HPLC by co-injection with the corresponding $^{19}$F compound on an analytical HPLC.

Example 6

2-(4-Amino-3-(18)fluorobenzamido)acetic acid (compound 6)

Method A (K$^{19}$F/H$_2$—Pd—C)

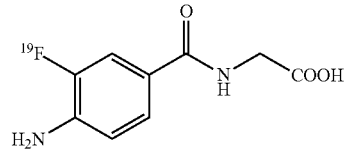 [SMILES: Nc1ccc(C(=O)NCC(=O)O)cc1[19F]]

Step 1:

Benzyl 2-(3-fluoro-4-nitrobenzamido)acetate: A mixture of spray-dried KF (614 mg, 10.59 mmol), intermediate 7 (1 g, 2.12 mmol), 18-crown-6 (40 mg) and dry acetonitrile (20 mL) was refluxed for 40 min. After completion of reaction (TLC), the mixture was diluted with EtOAc (75 mL). The solution was successively washed with water (50 mL) and brine (50 mL) and dried over anhyd Na$_2$SO$_4$. The solution was filtered and evaporated the solvent. The residue was chromatographed over silica gel column using chloroform:hexane (75:25) as eluents to give the product as a colorless solid (430 mg, 61%), mp 118-120° C. $^1$H NMR (400 MHz, CDCl$_3$): δ 8.13 (1H, t, J=7.8 Hz), 7.75 (1H, d, J=10.8 Hz), 7.68 (1H, d, J=8.0 Hz), 7.38 (5H, br s), 6.68 (1H, br s), 5.25 (2H, s), 4.29 (2H, d, J=4.8 Hz); LC-MS negative ion mode): m/z 331 (M−H)$^−$.

Step 2:

2-(4-Amino-3-fluorobenzamido)acetic acid: To a solution of benzyl 2-(3-fluoro-4-nitrobenzamido)acetate (200 mg) in EtOAc (10 mL) was added Pd/C (10%, 200 mg) at rt and stirred under the atmosphere of H$_2$ gas for 20 min. Work-up of the reaction mixture as described in example 1 gave product as an off-brown color solid (100 mg, 79%), mp 198-200° C. $^1$H NMR (400 MHz, DMSO-d$_6$): δ 12.52 (1H, br s), 8.45 (1H, br s), 7.52 (1H, d, J=13.2 Hz), 7.47 (1H, d, J=8.0 Hz), 6.77 (1H, t, J=8.4 Hz), 5.71 (2H, s), 3.87 (2H, d, J=5.2 Hz); $^{13}$C NMR (100 MHz, DMSO-d$_6$): δ 171.5, 165.5, 149.5 (d, J=235 Hz), 139.7 (d, J=13.0 Hz), 124.3 (d, J=2.0 Hz), 121.1 (d, J=6.0 Hz), 114.8 (d, J=4.0 Hz), 114.0 (d, J=20.0 Hz), 41.2; LC-MS (negative ion mode): m/z 211 (M−H)$^−$.

Method B: Ultrasound Conditions (Sonication)

Benzyl 2-(3-fluoro-4-nitrobenzamido)acetate: A mixture of spray-dried KF (122 mg, 2.1 mmol), intermediate 7 (100 mg, 0.21 mmol), 18-crown-6 (20 mg) and dry DMSO (4 mL) was exposed to ultrasound irradiation (sonication) for 10 min. Work-up of the reaction mixture as described above gave the product as a pale yellow color solid (42 mg, 60%). Which was further reduced as described in example 6 gave compound 6.

Method C (K$^{19}$F/Zn—AcOH)

Step 1:

2,2,2-Trichloroethyl 2-(3-fluoro-4-nitrobenzamido)acetate: A mixture of spray-dried KF (135 mg, 2.3 mmol), intermediate 8 (120 mg, 0.23 mmol) and catalytic amount of 18-crown-6 in DMSO (5 mL) was stirred at 95-100° C. for 15 min. Work-up of the reaction mixture as described in example 1 gave the product as a yellow color solid (57 mg, 65%), mp 142-144° C. $^1$H NMR (400 MHz, CDCl$_3$): δ 8.15 (1H, t, J=7.8 Hz), 7.78 (1H, dd, J=10.8, 1.6 Hz), 7.71 (1H, d, J=8.4 Hz), 6.70 (1H, br s), 4.86 (2H, s), 4.44 (2H, d, J=5.2 Hz); LC-MS (negative ion mode): m/z 371, 373 (M–H)$^-$.

Step 2:

2-(4-Amino-3-fluorobenzamido)acetic acid: A mixture of 2,2,2-trichloroethyl 2-(3-fluoro-4-nitrobenzamido)acetate (40 mg, 0.1 mmol), zinc dust (105 mg, 1.61 mmol) and AcOH (3 mL) was stirred at 85-90° C. for 15 min. The reaction mixture was attained to rt and diluted with EtOAc (30 mL). The solution was filtered through super cell and washed with EtOAc (2×5 mL). The residue obtained after evaporation of the solvent was chromatographed using chloroform:methanol (60:40) as eluents to give the product as an off-white color solid (17 mg, 75%), mp 198-200° C.

Method D (K$^{19}$F/Fe/AcOH)

Step 1:

2-(3-Fluoro-4-nitrobenzamido)acetic acid: A mixture of spray-dried KF (138 mg, 2.3 mmol), intermediate 9 (100 mg, 0.23 mmol), catalytic amount of 18-crown-6 in dry DMSO (4 mL) was stirred at 100-110° C. for 15 min. Work-up of the reaction mixture as described in example 1 gave the product as a colorless solid (40 mg, 69%), mp 136-138° C. $^1$H NMR (400 MHz, DMSO-d$_6$): δ 8.76 (1H, br s), 8.25 (1H, t, J=7.8 Hz), 8.00 (1H, d, J=12.0 Hz), 7.90 (1H, d, J=8.4 Hz), 3.75 (2H, d, J=4.4 Hz).

Step 2:

2-(4-Amino-3-fluorobenzamido)acetic acid: To a suspension of iron powder (231 mg, 4.13 mmol) in AcOH (2 mL) was added 2-(3-fluoro-4-nitrobenzamido)acetic acid (100 mg, 0.413 mmol) at rt and stirred at 85-90° C. for 15 min. The reaction mixture was attained to rt and diluted with EtOAc (20 mL). The solution was stirred for 5 min and filtered through celite. The celite bed was washed with EtOAc (10 mL) and the combined organic layer was evaporated under reduced pressure. The residue was chromatographed over silica gel column using chloroform:methanol (70:30) as eluents to give the product as an off-white color solid (62 mg, 71%), 198-200° C.

Method E (K$^{18}$F/Pd—C/1,4-cyclohexadiene)

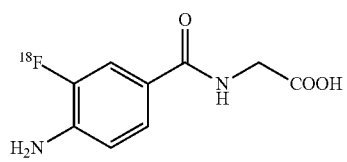

A solution of intermediate-7 in dry DMSO was added to the dry $^{18}$F-fluoride-cryptate complex and heated for 10 min at 120° C. After cooling, water was added and the mixture was passed through reversed phase column (Sep-Pak-C-18 column, waters). The column was washed three times with water and dried 2 min by a stream of nitrogen. The $^{18}$F-labeled protected compound was eluted with acetonitrile into another sealed reaction vessel and evaporated the solvent. The radiochemical yield of the product is 62% which was reduced with Pd/C and 1,4-cyclohexadiene and purification through HPLC. The identity of the compound was determined on an analytical HPLC by co-injection with the corresponding $^{19}$F compound on an analytical HPLC.

Method F (K$^{18}$F/Zn—AcOH)

A solution of intermediate-8 in dry DMSO was added to the dry $^{18}$F-fluoride-cryptate complex and heated for 10 min at 120° C. After cooling, water was added and the mixture was passed through reversed phase column (Sep-Pak-C-18 column, waters). The column was washed three times with water and dried 2 min by a stream of nitrogen. The $^{18}$F-labeled protected compound was eluted with acetonitrile into another sealed reaction vessel and evaporated the solvent. The radiochemical yield of the product is 58% which was reduced with zinc and acetic acid and purification through HPLC. The identity of the compound was determined on an analytical HPLC by co-injection with the corresponding $^{19}$F compound on an analytical HPLC.

Example 7

2-(4-Acetamido-3-(18)fluorobenzamido)acetic acid (compound 7)

Method A (K$^{19}$F/Fe—Ac$_2$O—AcOH)

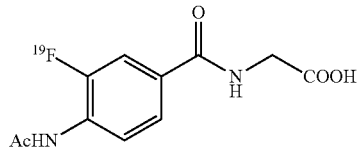

A mixture of spray-dried KF (138 mg, 2.3 mmol), intermediate 9 (100 mg, 0.23 mmol) and catalytic amount of 18-crown-6 (20 mg) in dry DMSO (4 mL) was stirred at 100-110° C. for 15 min. Work-up of the reaction mixture as described in example 1 gave the residue. This residue was dissolved in a mixture of AcOH and Ac$_2$O (5 mL, 1:1) and added iron powder (193 mg, 3.44 mmol) at rt. The mixture was stirred at 85-90° C. for 15 min and work-up of the reaction mixture as described in example 2 gave the product as an off-white color solid (39 mg, 65%), mp 236-238° C.; $^1$H NMR (400 MHz, DMSO-d$_6$): δ 12.53 (1H, br s), 9.92 (1H, br s), 8.84 (1H, t, J=6 Hz), 8.11 (1H, t, J=7.6 Hz), 7.67-7.73 (2H, m), 3.92 (2H, d, J=5.2 Hz), 2.13 (3H, s); LC-MS (negative ion mode): m/z 253 (M–H)$^-$.

Method B (K$^{18}$F/Fe—Ac$_2$O—AcOH)

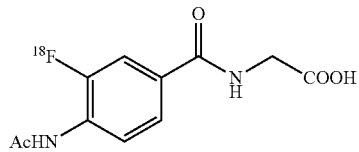 [SMILES: CC(=O)Nc1ccc(C(=O)NCC(=O)O)cc1[19F]]

A solution of intermediate-9 in dry DMSO was added to the dry $^{18}$F-fluoride-cryptate complex and heated for 10 min at 120° C. After cooling, water was added and the mixture was passed through reversed phase column (Sep-Pak-C-18 column, waters). The column was washed three times with water and dried 2 min by a stream of nitrogen. The $^{18}$F-labeled protected compound was eluted with acetonitrile into another sealed reaction vessel and evaporated the solvent. The radiochemical yield of the product is 58% which was reduced with iron powder and acetic anhydride-acetic acid and purification through HPLC. The identity of the compound was determined on an analytical HPLC by co-injection with the corresponding $^{19}$F compound on an analytical HPLC.

Example 8

2-(2-Amino-6-(18)fluorobenzamido)acetic acid (compound 8)

Method A (K$^{19}$F/Indium-AcOH)

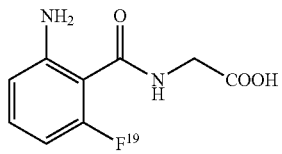

Step 1:
2-(2-Fluoro-6-nitrobenzamido)acetic acid: A mixture of spray-dried KF (215 mg, 3.71 mmol), intermediate 10 (100 mg, 0.371 mmol) and catalytic amount of 18-crown-6 in dry DMSO (4 mL) was stirred at 170-180° C. for 40 min. Work-up of the reaction mixture as described in example 1 gave the product as a pale yellow color solid (54 mg, 60%), mp 148-150° C. $^1$H NMR (400 MHz, DMSO-d$_6$): δ 9.05 (1H, br s), 8.00 (1H, d, J=7.2 Hz), 7.71-7.79 (2H, m), 3.96 (2H, d, J=5.2 Hz); LC-MS (negative ion mode): m/z 241 (M−H)$^-$.
Step 2:
2-(2-Amino-6-fluorobenzamido)acetic acid: To a suspension of indium powder (237 mg, 2.07 mmol) in AcOH (2 mL) was added 2-(2-fluoro-6-nitrobenzamido)acetic acid (50 mg, 0.21 mmol) at rt and stirred at 60° C. for 30 min. The reaction mixture was attained to rt and diluted with EtOAc (20 mL). The solution was stirred for 5 min and filtered through celite. The celite bed was washed with EtOAc (10 mL) and the combined organic layer was evaporated under reduced pressure. The residue was chromatographed over silica gel column using chloroform:methanol (70:30) as eluents to give the product as a pale brown color solid (32 mg, 73%), mp 188-192° C. $^1$H NMR (400 MHz, CDCl$_3$+DMSO-d$_6$): δ 7.80 (2H, br s), 7.04 (1H, dd, J=15.0, 7.8 Hz), 6.50 (1H, d, J=8.4 Hz), 6.27 (1H, t, J=9.4 Hz), 6.26 (1H, br s, exchangeable with D$_2$O), 3.74 (2H, d, J=3.6 Hz); $^{13}$C NMR (100 MHz, CDCl$_3$+DMSO-d$_6$): δ 172.7, 164.3, 160.7 (d, J=242 Hz), 150.1 (d, J=6 Hz), 130.9 (d, J=12 Hz), 111.5, 106.4 (d, J=18 Hz), 101.2 (d, J=24 Hz), 43.0; LC-MS (negative ion mode): m/z 211 (M−H)$^-$.

Method B (K$^{18}$F/Indium-AcOH)

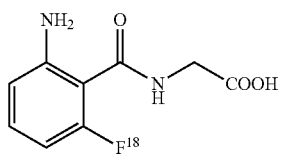

A solution of intermediate-10 in dry DMSO was added to the dry $^{18}$F-fluoride-cryptate complex and heated for 10 min at 120° C. After cooling, water was added and the mixture was passed through reversed phase column (Sep-Pak-C-18 column, waters). The column was washed three times with water and dried 2 min by a stream of nitrogen. The $^{18}$F-labeled protected compound was eluted with acetonitrile into another sealed reaction vessel and evaporated the solvent. The radiochemical yield of the product is 30% which was reduced with indium powder and acetic acid and purification through HPLC. The identity of the compound was determined on an analytical HPLC by co-injection with the corresponding $^{19}$F compound on an analytical HPLC.

Example 9

2-(2-Acetamido-6-(18)fluorobenzamido)acetic acid (compound 9)

Method A (K$^{19}$F/Indium-Ac$_2$O—AcOH)

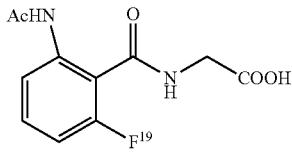

A mixture of spray-dried KF (539 mg, 9.29 mmol), intermediate 10 (250 mg, 0.929 mmol) and catalytic amount of 18-crown-6 in dry DMSO (8 mL) was stirred at 170-180° C. for 40 min. Work-up of the reaction mixture as described in example 1 gave the residue. This residue was dissolved in a mixture of AcOH and Ac$_2$O (1:1, 10 mL) and was added indium powder (1.06 g, 9.29 mmol) at rt. The reaction mixture was stirred at 60° C. for 30 min. The reaction mixture was attained to rt and diluted with EtOAc (50 mL). The solution was stirred for 5 min and filtered through celite. The celite bed was washed with EtOAc (2×10 mL) and the combined organic layer was evaporated under reduced pressure. The residue was chromatographed over silica gel column using chloroform:methanol (90:10) as eluents to give the product as a pale brown color solid (83 mg, 35%), mp 238-242° C. $^1$H NMR (400 MHz, DMSO-d$_6$): δ 11.00 (1H, br s, exchangeable with D$_2$O), 8.72 (1H, br s, exchangeable with D$_2$O), 8.21 (1H, d, J=8.4 Hz), 7.34 (1H, dd, J=15.4, 8.2 Hz), 6.90 (1H, t, J=8.8 Hz), 3.63 (2H, d, J=6.0 Hz), 2.17 (3H, s); $^{13}$C NMR (100 MHz, DMSO-d$_6$): δ 172.5, 169.7, 163.0, 158.3 (d, J=242 Hz), 138.2 (d, J=7 Hz), 130.0 (d, J=9 Hz), 116.5 (d, J=22 Hz), 116.2 (d, J=2 Hz), 109.3 (d, J=21 Hz), 43.8, 24.2; LC-MS (positive ion mode): m/z 255 (M+H)$^+$.

Method B (K$^{18}$F/Indium-Ac$_2$O—AcOH)

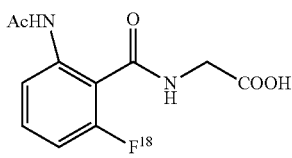

A solution of intermediate-10 in dry DMSO was added to the dry $^{18}$F-fluoride-cryptate complex and heated for 10 min at 120° C. After cooling, water was added and the mixture was passed through reversed phase column (Sep-Pak-C-18 column, waters). The column was washed three times with water and dried 2 min by a stream of nitrogen. The $^{18}$F-labeled protected compound was eluted with acetonitrile into another sealed reaction vessel and evaporated the solvent. The radiochemical yield of the product is 30% which was reduced with indium powder and acetic anhydride-acetic acid and purification through HPLC. The identity of the compound was determined on an analytical HPLC by co-injection with the corresponding $^{19}$F compound on an analytical HPLC.

Example 10

(S)-2-(4-Amino-2-(18)fluorobenzamido)propanoic acid (compound 10)

Method A ($K_{19}$F/Fe—AcOH)

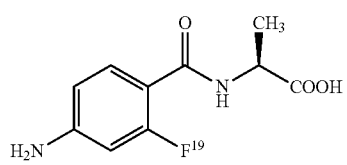

Step 1:
(S)-2-(2-Fluoro-4-nitrobenzamido)propanoic acid: A mixture of spray-dried KF (410 mg, 7.06 mmol), intermediate 11 (200 mg, 0.706 mmol) and catalytic amount of 18-crown-6 in dry DMSO (5 mL) was stirred at 170-180° C. for 30 min. Work-up of the reaction mixture as described in example 1 gave the product as a pale brown color solid (117 mg, 65%), mp 136-138° C. $^1$H NMR (400 MHz, DMSO-$d_6$): 812.74 (1H, br s), 8.96 (1H, d, J=7.2 Hz), 8.21 (1H, d, J=9.6 Hz), 8.16 (1H, d, J=8.4 Hz), 7.82 (1H, t, J=7.6 Hz), 4.42 (1H, pentet, J=7.0 Hz), 1.38 (3H, d, J=7.2 Hz); LC-MS (negative ion mode): m/z 255 (M−H)$^-$.

Step 2:
(S)-2-(4-Amino-2-fluorobenzamido)propanoic acid: To a suspension of iron powder (175 mg, 3.12 mmol) in AcOH (2 mL) was added (S)-2-(2-fluoro-4-nitrobenzamido)propanoic acid (80 mg, 0.31 mmol) at rt and stirred at 60-70° C. for 20 min. Work-up of the reaction mixture as described in example 6 gave the product as a pale brown color solid (53 mg, 75%), mp 244-248° C. $^1$H NMR (400 MHz, DMSO-$d_6$): δ 7.69 (1H, br s), 7.55 (1H, t, J=8.8 Hz), 6.41 (1H, d, J=8.4 Hz), 6.30 (1H, d, J=14.8 Hz), 5.97 (2H, br s), 4.15 (1H, br s), 1.31 (3H, d, J=6.8 Hz); LC-MS (positive ion mode): m/z 227 (M+H)$^+$.

Method B ($K^{18}$F/Fe—AcOH)

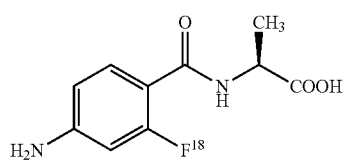

A solution of intermediate-11 in dry DMSO was added to the dry $^{18}$F-fluoride-cryptate complex and heated for 10 min at 120° C. After cooling, water was added and the mixture was passed through reversed phase column (Sep-Pak-C-18 column, waters). The column was washed three times with water and dried 2 min by a stream of nitrogen. The $^{18}$F-labeled protected compound was eluted with acetonitrile into another sealed reaction vessel and evaporated the solvent. The radiochemical yield of the product is 29% which was reduced with iron powder and acetic acid and purification through HPLC. The identity of the compound was determined on an analytical HPLC by co-injection with the corresponding $^{19}$F compound on an analytical HPLC.

Example 11

(R)-2-(4-Amino-2-(18)fluorobenzamido)propanoic acid (compound 11)

Method A ($K^{19}$F/Fe—AcOH)

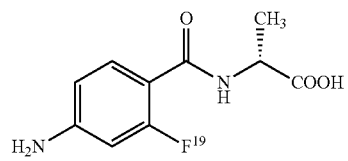

Step 1:
(R)-2-(2-Fluoro-4-nitrobenzamido)propanoic acid: A mixture of spray-dried KF (307 mg, 5.3 mmol), intermediate 12 (150 mg, 0.53 mmol) and catalytic amount of 18-crown-6 in dry DMSO (4 mL) was stirred at 170-180° C. for 30 min. Work-up of the reaction mixture as described in example 1 gave the product as a pale brown color solid (92 mg, 68%), mp 146-150° C. $^1$H NMR (400 MHz, DMSO-$d_6$): δ 8.90 (1H, d, J=4.0 Hz), 8.21 (1H, d, J=9.6 Hz), 8.15 (1H, d, J=8.0 Hz), 7.84 (1H, t, J=6.8 Hz), 4.36-4.40 (1H, m), 1.38 (3H, d, J=6.4 Hz); LC-MS (negative ion mode): m/z 255 (M−H)$^-$.

Step 2:
(R)-2-(4-Amino-2-fluorobenzamido)propanoic acid: To a suspension of iron powder (656 mg, 11.71 mmol) in AcOH (6 mL) was added (R)-2-(2-fluoro-4-nitrobenzamido)propanoic acid (300 mg, 1.17 mmol) at rt and stirred at 60-70° C. for 20 min. Work-up of the reaction mixture as described in example 6 gave the product as a white color solid (190 mg, 72%). $^1$H NMR (400 MHz, DMSO-$d_6$): δ 7.68 (1H, br s, exchangeable with $D_2$O), 7.56 (1H, t, J=9.0 Hz), 6.41 (1H, d, J=8.8 Hz), 6.31 (1H, d, J=15.2 Hz), 5.99 (2H, br s, exchangeable with $D_2$O), 4.15 (1H, br s), 1.30 (3H, d, J=6.8 Hz); LC-MS (negative ion mode): m/z 225 (M−H)$^-$.

Method B ($K^{18}$F/Fe—AcOH)

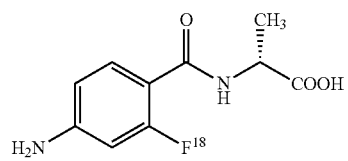

A solution of intermediate-12 in dry DMSO was added to the dry $^{18}$F-fluoride-cryptate complex and heated for 10 min at 120° C. After cooling, water was added and the mixture was passed through reversed phase column (Sep-Pak-C-18 column, waters). The column was washed three times with water and dried 2 min by a stream of nitrogen. The $^{18}$F-labeled protected compound was eluted with acetonitrile into another sealed reaction vessel and evaporated the solvent. The radiochemical yield of the product is 26% which was reduced with iron powder and acetic acid and purification through HPLC. The identity of the compound was determined on an analytical HPLC by co-injection with the corresponding $^{19}$F compound on an analytical HPLC.

Example 12

(S)-2-(2-Amino-6-(18)fluorobenzamido)propanoic acid (compound 12)

Method A (K$^{19}$F/Fe—AcOH)

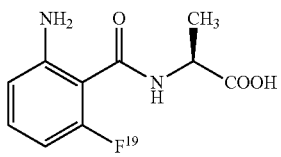

Step 1:
(S)-2-(2-Fluoro-6-nitrobenzamido)propanoic acid: A mixture of spray-dried KF (1.02 g, 17.6 mmol), intermediate 13 (500 mg, 1.76 mmol) and catalytic amount of 18-crown-6 in dry DMSO (10 mL) was stirred at 170-180° C. for 45 min. Work-up of the reaction mixture as described in example 1 gave the product as a pale brown color solid (284 mg, 63%), mp 142-144° C. $^1$H NMR (400 MHz, DMSO-d$_6$): δ 9.05 (1H, d, J=7.2 Hz), 8.01 (1H, dd, J=6.6, 1.8 Hz), 7.72-7.78 (2H, m), 4.44 (1H, pentet, J=7.2 Hz), 1.34 (3H, d, J=7.2 Hz); LC-MS (positive ion mode): m/z 279 (M+Na)$^+$.

Step 2:
(S)-2-(2-Amino-6-fluorobenzamido)propanoic acid: To a suspension of iron powder (437 mg, 7.81 mmol) in AcOH (5 mL) was added (S)-2-(2-fluoro-6-nitrobenzamido)propanoic acid (200 mg, 0.78 mmol) at rt and stirred at 60-70° C. for 30 min. Work-up of the reaction mixture as described in example 6 gave the product as an off-white color solid (132 mg, 75%), mp 194-198° C. $^1$H NMR (400 MHz, DMSO-d$_6$): δ 7.97 (1H, br s), 7.05 (1H, dd, J=15.2, 8.0 Hz), 6.49 (1H, d, J=8.4 Hz), 6.37 (2H, br s), 6.28 (1H, dd, J=11.2, 8.4 Hz), 4.14 (1H, br s), 1.30 (3H, d, J=7.2 Hz); $^{13}$C NMR (100 MHz, DMSO-d$_6$): δ 176.6, 163.7, 160.7 (d, J=241 Hz), 150.2 (d, J=6 Hz), 131.0 (d, J=12 Hz), 111.5, 106.6 (d, J=19 Hz), 101.2 (d, J=23 Hz), 49.4, 18.1; LC-MS (positive ion mode): m/z 227 (M+H)$^+$.

Method B (K$^{18}$F/Fe—AcOH)

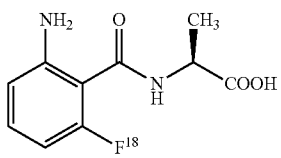

A solution of intermediate-13 in dry DMSO was added to the dry $^{18}$F-fluoride-cryptate complex and heated for 30 min at 170° C. After cooling, water was added and the mixture was passed through reversed phase column (Sep-Pak-C-18 column, waters). The column was washed three times with water and dried 2 min by a stream of nitrogen. The $^{18}$F-labeled protected compound was eluted with acetonitrile into another sealed reaction vessel and evaporated the solvent. The radio-chemical yield of the product is 44% which was reduced with iron powder and acetic acid and purification through HPLC. The identity of the compound was determined on an analytical HPLC by co-injection with the corresponding $^{19}$F compound on an analytical HPLC.

Example 13

(R)-2-(2-Amino-6-(18)fluorobenzamido)propanoic acid (compound 13)

Method A (K$^{19}$F/Fe—AcOH)

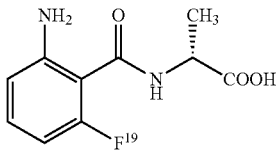

Step 1:
(R)-2-(2-Fluoro-6-nitrobenzamido)propanoic acid: A mixture of spray-dried KF (1.02 g, 17.6 mmol), intermediate 14 (500 mg, 1.76 mmol) and catalytic amount of 18-crown-6 in dry DMSO (10 mL) was stirred at 170-180° C. for 45 min. Work-up of the reaction mixture as described in example 1 gave the product as a pale brown color solid (290 mg, 64%), mp 158-160° C. $^1$H NMR (400 MHz, DMSO-d$_6$): δ 12.72 (1H, br s), 9.10 (1H, d, J=7.2 Hz), 8.01 (1H, d, J=7.2 Hz), 7.70-7.78 (2H, m), 4.46 (1H, pentet, J=7.0 Hz), 1.34 (3H, d, J=7.2 Hz); LC-MS (positive ion mode): m/z 279 (M+Na)$^+$.

Step 2:
(R)-2-(2-Amino-6-fluorobenzamido)propanoic acid: To a suspension of iron powder (1.3 g, 23.42 mmol) in AcOH (12 mL) was added (R)-2-(2-fluoro-6-nitrobenzamido)-propanoic acid (600 mg, 2.34 mmol) at rt and stirred at 60-70° C. for 30 min. Work-up of the reaction mixture as described in example 6 gave the product as an off-white color solid (380 mg, 72%), mp 220-224° C. $^1$H NMR (400 MHz, DMSO-d$_6$): δ 12.67 (1H, br s), 8.46 (1H, d, J=5.2 Hz), 7.08 (1H, dd, J=14.8, 7.2 Hz), 6.50 (1H, d, J=8.0 Hz), 6.31 (1H, t, J=9.2 Hz), 5.89 (2H, br s), 4.37 (1H, pentet, J=7.2 Hz), 1.35 (3H, d, J=7.2 Hz); LC-MS (positive ion mode): m/z 227 (M+H)$^+$.

Method B (K$^{18}$F/Fe—AcOH)

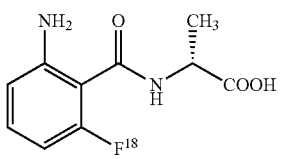

A solution of intermediate-14 in dry DMSO was added to the dry $^{18}$F-fluoride-cryptate complex and heated for 30 min at 170° C. After cooling, water was added and the mixture was passed through reversed phase column (Sep-Pak-C-18 column, waters). The column was washed three times with water and dried 2 min by a stream of nitrogen. The $^{18}$F-labeled protected compound was eluted with acetonitrile into another sealed reaction vessel and evaporated the solvent. The radiochemical yield of the product is 49% which was reduced with iron powder and acetic acid and purification through HPLC.

The identity of the compound was determined on an analytical HPLC by co-injection with the corresponding $^{19}$F compound on an analytical HPLC.

Biology

Example 14

Plasma Clearance

The plasma clearance will provide an accurate measurement of renal function, a renal agent must be exclusively excreted via the renal-urinary pathway to be used in humans. The plasma clearance of the compounds of formula (I) were determined using a single injection clearance method (Blaufox M. D. et al., Am. J. Physiol., 1967, 212, 629-632).

The experiment was carried out in accordance with the guidelines of Institutional Animal Ethics Committee (IAEC). The experiment for each compound was performed in isoflurane-anesthetized male SD rats (body weight 180-260 gm; n=3). Solution formulation of each compound was prepared in sterile water for injection with strength of 1 mg/mL. All solution formulations were prepared freshly prior to dosing. The dose volume for i.v bolus injection was 2 mL/kg. Three rats for each compound were administered intravenously (i.v.) bolus injection in tail vein at 2 mg/kg body weight. Blood samples were obtained at pre-dose (0 hr), 0.08, 0.17, 0.25, 0.5, 0.75, 1 and 2 hr post dosing. The blood samples (~120 µL) were taken from the retro-orbital plexus into labelled micro centrifuge tubes, containing 10 µL of 2% w/v $K_2EDTA$ solution, as an anticoagulant. Plasma was harvested from the blood by centrifugation at 1470 g for 10 min at 4±2° C. and stored below −80° C. until bioanalysis. Bioanalysis of rat plasma samples were analysed with developed method for each analyte using LC-MS/MS (Waters, Xevo TQ-S). The pharmacokinetic parameters such as area under the curve (AUC), elimination half-life ($T_{1/2}$), volume of distribution ($V_{ss}$) and clearance (CL) were estimated using a noncompartmental model in Phoenix WinNonlin software, version 6.3. The results were shown in Table 2.

TABLE 2

Plasma clearance of compounds of formula (I) in rats

| Compd. No. | Clearance (mL/min/100 g) |
|---|---|
| Compound 1 | 5.86 ± 0.50 |
| Compound 2 | 2.23 ± 0.10 |
| Compound 3 | 2.78 ± 0.19 |
| Compound 6 | 3.48 ± 0.63 |
| Compound 8 | 1.55 ± 0.10 |
| Compound 10 | 3.25 ± 0.13 |
| Compound 11 | 3.36 ± 0.41 |

Example 15

Bio-Distribution

Female Swiss Albino mice were randomized (4 animals per time-point) according to body weight on the day prior to the experimental date. Some of the selected compounds of formula (I) are evaluated for a limited bio-distribution study involving five selected organs of interest such as Blood, Liver, Small Intestines, Kidneys and Urine. Each compound was dissolved in a vehicle comprising of 10% N-methyl-2-pyrrolidone in sterile water to achieve a final strength of 1 mg/mL. The mixture was sonicated for 2 min to yield a clear solution. Compound was administered to mice via tail vein at a dose volume of 2 mL/kg in order to obtain a final dose of 2 mg/kg. Mice were euthanized at 15 minutes following dose administration. Blood was collected from the retro-orbital plexus in K2-EDTA containing tubes, centrifuged, plasma harvested and stored at −80° C. until further analysis. Liver, kidneys (right and left), and small intestine were harvested, weighted, and stored at −80° C. The small intestine was flushed with normal saline prior to storage. Urine was collected directly from the bladder and stored at −80° C.

Liver, kidneys, and small intestine were homogenized in water at 20% w/v. The respective homogenates were mixed thoroughly and stored at −80° C. until further processing. An aliquot of 100 µL of plasma/tissue homogenate was transferred to a 1.5 mL micro centrifuge tube. Twenty five microliters of compound (5 µg/mL), hundred microliters of 1% formic acid and 750 µL of tert-butyl methyl ether were added and sample was vortexed for 3 min. After centrifugation of the sample at 12,000 rpm at 4° C. for 5 min, supernatant was removed and evaporated under nitrogen stream at 40° C. for an additional 10 min (nitrogen evaporator, Caliper Instruments USA). The residue was reconstituted with 125 µL of solution (acetonitrile:water 1:1) and 10 µL was injected into the chromatographic system. On similar lines, an aliquot of 50 µL of urine was transferred to a 1.5 mL micro centrifuge tube. One hundred and fifty microliters of compound (5 µg/mL), was added and sample was vortexed for 3 min. After centrifugation of the sample at 12,000 rpm at 4° C. for 5 min, supernatant was removed and 10 µL was subjected to LC-MS/MS (Thermo Quantum Ultra) for the analysis.

Analyte concentrations were determined by evaluating the peak area ratio of drug to internal standard against a standard curve. The standard curve was prepared by plotting the relationship between peak area ratio of analyte to internal standard against concentration of standard CC samples by using linear regression y=ax+b and putting the $1/x^2$ as weighting factor.

Data were expressed as ng/g for liver, kidneys, and small intestine. Percent compound in tissues was calculated based on the absolute dose administered (mg/kg). Plasma concentrations as a percent of administered dose were extrapolated assuming a total blood volume of 6% body weight and a 60% yield (plasma from blood). Compound concentrations in urine were expressed as µg per total volume collected. The bio-distribution data of these inventive compounds were shown in Table-3 as percent injected dose (% ID) at 15 minute time after injection, indicating the efficiency of novel agents.

TABLE 3

Bio-distribution of compounds of formula (I) in mice at 15 min after injection

| Compd. No. | Blood (% ID) | Liver (% ID) | Small Intestine (% ID) | Kidney (% ID) | Urine (% ID) |
|---|---|---|---|---|---|
| Compound 1 | 1.07 ± 0.56 | 0.10 ± 0.22 | 0.07 ± 0.08 | 0.51 ± 0.45 | 87.76 ± 6.03 |
| Compound 2 | 0.60 ± 0.10 | 0.78 ± 0.25 | 0.09 ± 0.04 | 1.19 ± 0.53 | 84.42 ± 3.44 |
| Compound 3 | 0.83 ± 0.02 | 0.08 ± 0.04 | 0.04 ± 0.02 | 0.13 ± 0.01 | 72.73 ± 1.91 |
| Compound 6 | 0.68 ± 0.38 | 0.08 ± 0.02 | 0.11 ± 0.08 | 0.47 ± 0.20 | 78.21 ± 4.79 |
| Compound 8 | 1.08 ± 0.58 | 0.36 ± 0.26 | 0.10 ± 0.09 | 0.91 ± 0.40 | 87.51 ± 4.14 |
| Compound 10 | 0.50 ± 0.27 | 0.21 ± 0.05 | 0.01 ± 0.01 | 0.09 ± 0.04 | 83.59 ± 8.82 |
| Compound 11 | 0.94 ± 0.53 | 0.02 ± 0.03 | 0.09 ± 0.05 | 0.06 ± 0.02 | 82.31 ± 9.60 |

Data are mean SD (n = 4)

From these results (Table 3) it is evident that these compounds showed rapid clearance from the blood exclusively through renal-urinary pathway, with minimal retention in the kidneys or liver or small intestine at 15 min after injection, showing their efficiency.

TABLE 4

Bio-distribution of compounds of formula (I) in mice at 60 min after injection

| Compd. No. | Blood (% ID) | Liver (% ID) | Small Intestine (% ID) | Kidney (% ID) |
|---|---|---|---|---|
| Compound 1 | 0.35 ± 0.04 | 0.00 ± 0.00 | 0.00 ± 0.00 | 0.00 ± 0.00 |
| Compound 2 | 0.00 ± 0.00 | 0.19 ± 0.33 | 0.02 ± 0.02 | 0.05 ± 0.09 |
| Compound 3 | 0.02 ± 0.02 | 0.00 ± 0.00 | 0.00 ± 0.00 | 0.00 ± 0.00 |
| Compound 6 | 0.02 ± 0.01 | 0.02 ± 0.02 | 0.01 ± 0.01 | 0.01 ± 0.01 |
| Compound 8 | 0.02 ± 0.01 | 0.05 ± 0.02 | 0.01 ± 0.01 | 0.02 ± 0.03 |
| Compound 10 | 0.01 ± 0.00 | 0.05 ± 0.07 | 0.00 ± 0.00 | 0.00 ± 0.00 |
| Compound 11 | 0.12 ± 0.17 | 0.00 ± 0.00 | 0.00 ± 0.00 | 0.01 ± 0.02 |

Data are mean SD (n = 4)

From the bio-distribution study results (Table 4), it is evident that these compounds showed no retention in the liver, small intestine and kidneys at 60 min after injection, this shows higher specificity of the compounds through renal excretion without heptatobiliary.

We claim:

1. A $^{18}$F labeled compound of formula (I), pharmaceutically acceptable salt or isomers or solvates or hydrates thereof;

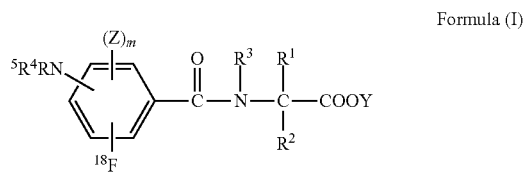

Formula (I)

wherein Y, Z $R^1$, $R^2$, $R^3$, $R^4$ and $R^5$ are each H; m is 3; and wherein at least one of $^{18}$F and $NR^4R^5$ is meta or para to $C(O)NR^3$—$C(R^1)(R^2)$—COOY.

2. A $^{18}$F labeled compound of formula (I), pharmaceutically acceptable salt or isomers or solvates or hydrates thereof;

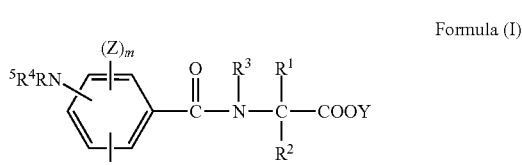

Formula (I)

wherein:
Y, Z, $R^1$, $R^2$, and $R^3$ are each H; and
one of $R^4$ or $R^5$ is H and the other of $R^4$ or $R^5$ is $COCH_3$.

3. A $^{18}$F labeled compound of formula (I), pharmaceutically acceptable salt or isomers or solvates or hydrates thereof;

Formula (I)

wherein;
Y is hydrogen;
Z is hydrogen;
m is 3;
$R^1$ and $R^2$ are independently selected from the group consisting of hydrogen and $CH_3$;
$R^3$ is hydrogen;
$R^4$ and $R^5$ are independently selected from the group consisting of hydrogen and acetyl;
wherein no more than one of $^{18}$F and $NR^4R^5$ is ortho to $C(O)NR^3$—$C(R^1)(R^2)$—COOY.

4. A process for the preparation of $^{18}$F-labeled compound according to claim 3, comprising;
a) reacting $M^{18}F$, wherein M is an alkali metal, alkaline earth metal, or ammonium compounds, with a compound of formula (III), wherein X is Cl, Br, I, F, $NO_2$, in the presence of a phase transfer catalyst and a solvent to give formula (IV); and
b) reacting the compound of formula (IV) with a reducing agent to produce the $^{18}$F labeled compound;
said reaction of step (b) being optionally performed in the presence of acid, organic acid anhydride, or a mixture thereof;

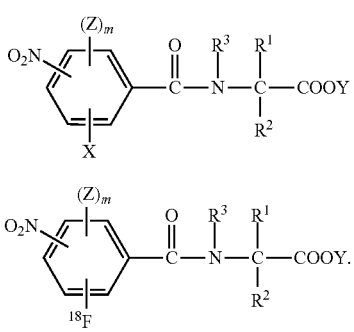

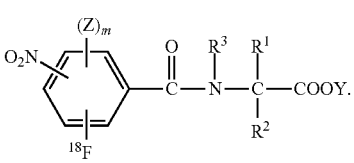

5. A process for the preparation of $^{18}$F-labeled compound according to claim 3, comprising;
   a) reacting an oxidizing agent with a compound of formula (III), wherein X is I, to produce an oxidized compound of formula (III), wherein X is $IO_2$;
   b) reacting the oxidized compound of formula (III) with $M^{18}F$, wherein M is an alkali metal, alkaline earth metal, or ammonium compounds, in the presence of a phase transfer catalyst and a solvent to give a compound of formula (IV); and
   c) reacting the compound of formula (IV) with a reducing agent to produce the $^{18}$F labeled compound;
   said reaction of step (c) being optionally performed in the presence of acid, organic acid anhydride, or a mixture thereof;

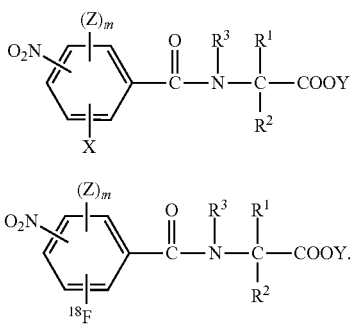

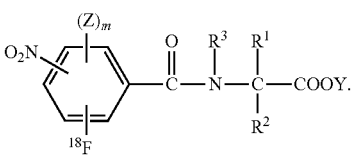

6. The process for the preparation of compound of formula (I) as claimed in claim 4, wherein the chemical reactions are conducted at ambient temperature under thermal or microwave or ultrasonic conditions.

7. The process for the preparation of compound of formula (I) as claimed in claim 5, wherein the chemical reactions are conducted at ambient temperature under thermal or microwave or ultrasonic conditions.

8. The process for the preparation of $^{18}$F-labeled compound of formula (I) as claimed in claim 4, wherein said phase transfer catalyst is selected from 18-crown-6,15-crown-5, kryptofix-222, tetraphenylphosphonium bromide, tetrabutylammonium halides or polyethylene glycol (PEG); preferably kryptofix-222.

9. The process for the preparation of $^{18}$F-labeled compound of formula (I) as claimed in claim 4, wherein said solvent is selected from the group consisting of acetonitrile, dimethylsulfoxide, dimethylformamide, sulfolane, methylsulfone, tetraethyleneglycol dimethylether, tetrahydrofuran, ethylene glycol, hexamethylphosphoramide or N-methyl-2-pyrrolidone.

10. The process for the preparation of $^{18}$F-labeled compound of formula (I) as claimed in claim 4, wherein said reducing agent is selected from the group consisting of iron, tin, zinc, indium, stannous chloride, nickel chloride, sodium sulfide, sodium dithionite, palladium-carbon in the presence of hydrogen gas or hydrogen source; or Raney-nickel in the presence of hydrogen gas or hydrogen source; hydrogen source is selected from 1,4-cyclohexadiene, cyclohexene, ammonium formate or formic acid.

11. The process for the preparation of $^{18}$F-labeled compound of formula (I) as claimed in claim 5, wherein said reducing agent is selected from the group consisting of iron, tin, zinc, indium, stannous chloride, nickel chloride, sodium sulfide, sodium dithionite, palladium-carbon in the presence of hydrogen gas or hydrogen source; or Raney-nickel in the presence of hydrogen gas or hydrogen source; hydrogen source is selected from 1,4-cyclohexadiene, cyclohexene, ammonium formate or formic acid.

12. The process for the preparation of $^{18}$F-labeled compound of formula (I) as claimed in claim 4, wherein said acid is selected from the group consisting of hydrochloric acid, nitric acid, sulfuric acid, phosphoric acid, methanesulfonic acid, acetic acid, formic acid or propionic acid; organic acid anhydride is selected from formic anhydride, acetic anhydride, propionic anhydride or mixtures thereof.

13. The process for the preparation of $^{18}$F-labeled compound of formula (I) as claimed in claim 5, wherein said oxidizing agent is selected from the group consisting of hydrogen peroxide-acetic anhydride, peracetic acid, perbenzoic acid, sodium hypochlorite, dimethyldioxirane, chromium trioxide, potassium permanganate, sodium periodate or potassium bromate.

14. A pharmaceutical composition comprising at least one compound of formula (I) as claimed in claim 3 or a pharmaceutically acceptable salt or solvates or hydrates or stereoisomers thereof and at least one selected from pharmaceutically acceptable excipient, pharmaceutically acceptable diluents, and pharmaceutically acceptable carrier.

15. The pharmaceutical composition as claimed in claim 14, wherein the excipient, diluent, and carrier is selected from the group consisting of; glucose, fructose, sucrose, maltose, yellow dextrin, white dextrin, aerosol, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, calcium salts, pigments, flavors, preservatives, distilled water, saline, aqueous glucose solution, alcohol (e.g. ethanol), propylene glycol, polyethylene glycol, various animal and vegetable oils, white soft paraffin, paraffin and wax.

16. A pharmaceutical composition comprising at least one compound of formula (I) as claimed in claim 3 or a pharmaceutically acceptable salt or solvates or hydrates or stereoisomers thereof and at least one selected from pharmaceutically acceptable excipient, pharmaceutically acceptable diluents, and pharmaceutically acceptable carrier and further comprising at least one $^{19}$F compound of formula (Ia) or their pharmaceutically acceptable salt or solvates or hydrates or stereo-isomers thereof;

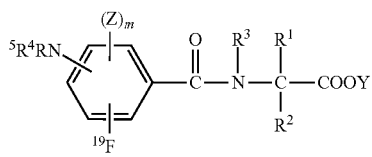

Formula (Ia)

wherein;
hydrogen, Z is hydrogen; m is 3; $R^1$ and $R^2$ are independently selected from the group consisting of hydrogen and $CH_3$; $R^3$ is hydrogen; $R^4$ and $R^5$ are independently selected from the group consisting of hydrogen and acetyl; wherein no more than one of $^{18}F$ and $NR^4R^5$ is ortho to $C(O)NR^3$—$C(R^1)(R^2)$—COOY—independently selected from hydrogen, $C_{1-6}$alkyl, $C_{1-6}$secondaryalkyl, $C_{1-6}$tertiaryalkyl, $C_{2-6}$alkenyl, $C_{2-6}$alkynyl, halo$C_{1-6}$alkyl, hydroxy$C_{1-6}$alkyl, $C_{3-7}$cycloalkyl, $C_{1-6}$alkylamino$C_{1-6}$alkyl, di($C_{1-6}$alkyl)amino$C_{1-6}$alkyl, $C_{1-6}$alkylaryl, $C_{1-6}$alkylheteroaryl, $C_{1-6}$alkylcarboxylic acid, $C_{1-6}$alkylcarboxamide and a aryl, heteroaryl, $C_{1-6}$alkylaryl, $C_{1-6}$alkylheteroaryl and heterocycloalkyl ring; aryl, heteroaryl and heterocycloalkyl ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl; wherein halogen is selected from all isotopes of F, Cl, Br and I;

Z is independently selected from hydrogen, halogen, astatine (At), hydroxy, formyl, carboxylic acid, amino, nitro, cyano, sulfonic acid, thiole, trihalomethyl, sulfonamide, $C_{1-6}$alkyl, $C_{1-6}$secondaryalkyl, $C_{1-6}$tertiaryalkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl, and a aryl, heteroaryl, $C_{1-6}$alkylaryl, $C_{1-6}$alkylheteroaryl and heterocycloalkyl ring; aryl, heteroaryl and heterocycloalkyl ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl; wherein halogen is selected from all isotopes of F, Cl, Br and I;

m is 0, 1, 2 or 3

$R^1$ is independently selected from hydrogen, halogen, astatine (At), $C_{1-6}$alkyl, $C_{1-6}$secondaryalkyl, $C_{1-6}$tertiaryalkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl, mercapto$C_{1-6}$alkyl, $C_{1-6}$alkylmercapto$C_{1-6}$alkyl, $C_{1-6}$alkylaryl, $C_{1-6}$alkylheteroaryl, $C_{1-6}$alkylcarboxylic acid, $C_{1-6}$alkylcarboxamide, $C_{1-6}$alkylguanidine, $C_{1-6}$alkylselenol and a aryl, heteroaryl, $C_{1-6}$alkylaryl, $C_{1-6}$alkylheteroaryl and heterocycloalkyl ring; aryl, heteroaryl and heterocycloalkyl ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl; wherein halogen is selected from all isotopes of F, Cl, Br and I;

$R^2$ is independently selected from hydrogen, halogen, astatine (At), $C_{1-6}$alkyl, $C_{1-6}$secondaryalkyl, $C_{1-6}$tertiaryalkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$lkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl, mercapto$C_{1-6}$alkyl, $C_{1-6}$alkylmercapto$C_{1-6}$alkyl, $C_{1-6}$alkylaryl, $C_{1-6}$alkylheteroaryl, $C_{1-6}$alkylcarboxylic acid, $C_{1-6}$alkylcarboxamide, $C_{1-6}$alkylguanidine, $C_{1-6}$alkylselenol and a aryl, heteroaryl, $C_{1-6}$alkylaryl, $C_{1-6}$alkylheteroaryl and heterocycloalkyl ring; aryl, heteroaryl and heterocycloalkyl ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl; wherein halogen is selected from all isotopes of F, Cl, Br and I;

$R^3$ is independently selected from hydrogen, $C_{1-6}$alkyl, halo$C_{1-6}$alkyl, halo$C_{1-6}$alkoxy, $C_{3-7}$cycloalkyl;

$R^1$ and $R^3$ optionally $R^1$ and $R^3$ are joined, and taken together with the atoms to which they are attached, form a 5- to 7-membered heterocycloalkyl ring; the heteroatom is N;

$R^4$ and $R^5$ is independently selected from hydrogen, oxygen, formyl, amino, $C_{1-6}$alkyl, $C_{1-6}$secondaryalkyl, $C_{1-6}$tertiaryalkyl, $C_{2-6}$alkenyl, $C_{2-6}$alkynyl, $C_{1-4}$alkylcarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{3-7}$cycloalkyl, $C_{1-6}$alkylamino, di($C_{1-6}$alkyl)amino, amino$C_{1-6}$ alkyl, $C_{1-6}$alkylamino$C_{1-6}$alkyl, di($C_{1-6}$alkyl)amino$C_{1-6}$alkyl, and a aryl, heteroaryl and heterocycloalkyl ring; aryl, heteroaryl, $C_{1-6}$alkylaryl, $C_{1-6}$alkylheteroaryl and heterocycloalkyl ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl; wherein halogen is selected from all isotopes of F, Cl, Br and I.

17. A method of diagnosing kidney function in a warm blooded animal in need thereof, wherein said method comprises administering to the said warm blooded animal a diagnostic amount of at least one $^{18}$F compound of formula (I) as claimed in claim 3; or a pharmaceutically acceptable salt, isomer, hydrate or solvate thereof.

18. A method of diagnosing kidney function in a warm blooded animal in need thereof, wherein said method comprises administering to the said warm blooded animal a diagnostic amount of at least one $^{18}$F compound of formula (I) as claimed in claim 3 and performing diagnostic imaging using PET by detecting a signal from said at least one $^{18}$F compound.

19. A method of diagnosing kidney function in a warm blooded animal in need thereof as claimed in claim 17, wherein said method comprises administering to the said warm blooded animal a diagnostic amount of composition comprising at least one $^{18}$F compound of formula (I), pharmaceutically acceptable salt or solvates or hydrates or stereoisomers thereof in combination with a pharmaceutically acceptable excipient(s) or carrier(s) or diluent(s); and performing diagnostic imaging using PET by detecting a signal from said $^{18}$F compound of formula (I).

20. A method of diagnosing kidney function in a warm blooded animal in need thereof, wherein said method comprises administering to the said warm blooded animal a diagnostic amount of the pharmaceutical composition of claim 16, and performing diagnostic imaging using PET by detecting a signal from said $^{18}$F compound of formula (I).

21. The method of diagnosing kidney function as claimed in claim 18, wherein the positron emission tomography (PET) comprises recording multiple consecutive and dynamic images during the passage of $^{18}$F compound of formula (I) through the kidney (s).

22. The method as claimed in claim 18, wherein the said method is used to assess the kidney function on transplanted organ for its rejection or acceptance by the host.

23. The method as claimed in claim 18, wherein the said method is used to assess the kidney function in a normal, diseased and transplanted state of children for pediatric usage.

24. A $^{18}$F labeled compound of formula (I), pharmaceutically acceptable salt or isomers or solvates or hydrates thereof;

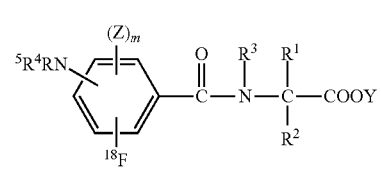

Formula (I)

wherein:
Y, Z, and $R^3$ are each H;
$R^1$ and $R^2$ are selected from the group consisting of H and $CH_3$;
m is 3; and
either:
$R^4$ and $R^5$ are each H; or
one of $R^4$ and $R^5$ is H and the other of $R^4$ and $R^5$ is $COCH_3$;
wherein at least one of $^{18}$F and $NR^4R^5$ is meta or para to $C(O)NR^3$—$C(R^1)(R^2)$—COOY.

25. The $^{18}$F-labeled compound of formula (I) as claimed in claim 24, wherein $R^1$, $R^2$, $R^4$, and $R^5$ are each H.

26. The $^{18}$F-labeled compound of formula (I) as claimed in claim 24, wherein:
one of $R^4$ or $R^5$ is H and the other of $R^4$ or $R^5$ is $COCH_3$.

27. The $^{18}$F-labeled compound of formula (I) as claimed in claim 24, wherein:
one of $R^1$ and $R^2$ is $CH_3$ and the other of $R^1$ and $R^2$ is H.

28. A $^{18}$F labeled compound of formula (I), pharmaceutically acceptable salt or isomers or solvates or hydrates thereof;

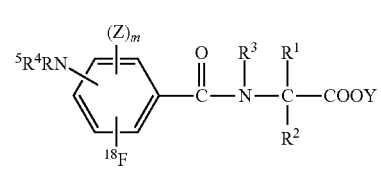

Formula (I)

wherein:
Y, Z, and $R^3$ are each H;
$R^1$ and $R^2$ are selected from the group consisting of H and $CH_3$;
m is 3; and
either:
$R^4$ and $R^5$ are each H; or
one of $R^4$ and $R^5$ is H and the other of $R^4$ and $R^5$ is $COCH_3$;
wherein no more than one of $^{18}$F and $NR^4R^5$ is ortho to $C(O)NR^3$—$C(R^1)(R^2)$—COOY.

29. A compound selected from the group consisting of
2-(4-amino-2-[$^{18}$F]-fluorobenzamido)acetic acid;
2-(4-acetamido-2-[$^{18}$F]-fluorobenzamido)acetic acid;
2-(3-amino-4-[$^{18}$F]-fluorobenzamido)acetic acid;
2-(5-amino-2-chloro-4-[$^{18}$F]-fluorobenzamido)acetic acid;
2-(5-amino-2-[$^{18}$F]-fluorobenzamido)acetic acid;
2-(4-amino-3-[$^{18}$F]-fluorobenzamido)acetic acid;
2-(4-acetamido-3-[$^8$F]-fluorobenzamido)acetic acid;
2-(2-acetamido-6-[$^{18}$F]-fluorobenzamido)acetic acid;
(S)-2-(4-amino-2-[$^{18}$F]-fluorobenzamido)propanoic acid;
(R)-2-(4-amino-2[$^{18}$F]-fluorobenzamido)propanoic acid;
(S)-2-(2-amino-6-[$^{18}$F]-fluorobenzamido)propanoic acid;
(R)-2-(2-amino-6-[$^{18}$F]-fluorobenzamido)propanoic acid.

30. The $^{18}$F-labeled compound of formula (I) as claimed in claim 3, wherein:
Y, Z, and $R^3$ are each H;
one of $R^1$ and $R^2$ is $CH_3$ and the other of $R^1$ and $R^2$ is H;
either:
  $R^4$ and $R^5$ are each H; or
  one of $R^4$ and $R^5$ is H and the other of $R^4$ and $R^5$ is $COCH_3$; and
the compound of formula (I) is
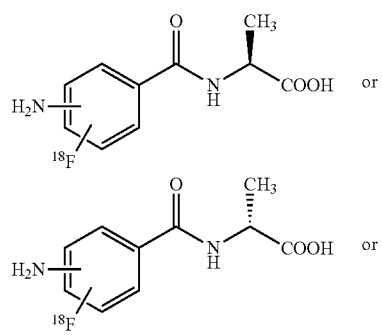 or
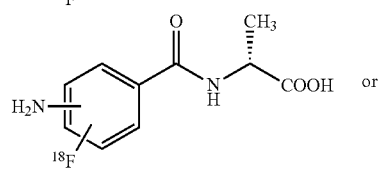 or
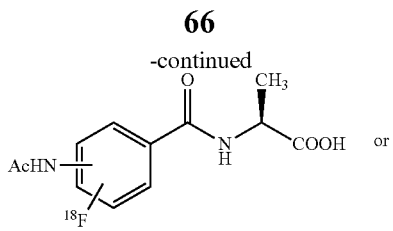 or
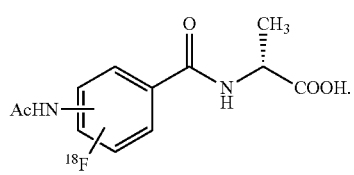.
* * * * *

UNITED STATES PATENT AND TRADEMARK OFFICE
CERTIFICATE OF CORRECTION

PATENT NO. : 8,906,344 B2
APPLICATION NO. : 14/031973
DATED : December 9, 2014
INVENTOR(S) : Sudhakar Kasina et al.

It is certified that error appears in the above-identified patent and that said Letters Patent is hereby corrected as shown below:

In the Claims,

In Claim 1, Column 57, line 61, replace "wherein Y, Z $R^1$, $R^2$, $R^3$, $R^4$ and $R^5$ are each H;" with --wherein Y, Z, $R^1$, $R^2$, $R^3$, $R^4$ and $R^5$ are each H;--

In Claim 16, insert --Y is-- in Column 61, line 11, prior to "hydrogen, Z is hydrogen."

In Claim 16, delete all text from "independently selected from hydrogen," starting on Column 61, line 16, to "wherein halogen is selected from all isotopes of F, Cl, Br and I" ending on Column 63, line 17, inclusive.

Signed and Sealed this
Twenty-first Day of July, 2015

Michelle K. Lee
*Director of the United States Patent and Trademark Office*